US007544721B2

(12) United States Patent
Gaud et al.

(10) Patent No.: US 7,544,721 B2
(45) Date of Patent: Jun. 9, 2009

(54) PHOTOSENSITIVE ADHESIVE COMPOSITION

(75) Inventors: Vincent Gaud, Vitry sur Seine (FR); Yves Gnanou, Talence (FR); Jean-Pierre Desvergne, Leognan (FR); Francis Dieras, Bordeaux (FR); Alexandrine Roubiere, Bordeaux (FR)

(73) Assignee: Produits Dentaires Pierre Rolland, Merignac (FR)

( * ) Notice: Subject to any disclaimer, the term of this patent is extended or adjusted under 35 U.S.C. 154(b) by 634 days.

(21) Appl. No.: 10/510,112

(22) PCT Filed: Apr. 2, 2003

(86) PCT No.: PCT/FR03/01029

§ 371 (c)(1),
(2), (4) Date: Apr. 11, 2005

(87) PCT Pub. No.: WO03/082218

PCT Pub. Date: Oct. 9, 2003

(65) Prior Publication Data

US 2005/0182148 A1 Aug. 18, 2005

(30) Foreign Application Priority Data

Apr. 3, 2002 (FR) .................................. 02 04179

(51) Int. Cl.
*C08F 2/50* (2006.01)
*C08F 2/46* (2006.01)
*C08J 3/28* (2006.01)

(52) U.S. Cl. ......................... 522/151; 522/150; 522/153; 522/154; 522/152; 522/35; 522/162; 522/167; 522/168; 522/169; 522/170; 522/173; 522/178; 522/181; 522/182; 522/31; 522/38; 522/32

(58) Field of Classification Search ................. 522/904, 522/351, 50, 151, 152, 153, 154, 162, 167, 522/168, 170, 173, 178, 181, 182, 31, 32, 522/38

See application file for complete search history.

(56) References Cited

U.S. PATENT DOCUMENTS

| 4,286,047 | A | | 8/1981 | Bennett et al. |
| 5,872,158 | A | * | 2/1999 | Kuczynski .................... 522/182 |
| 6,008,266 | A | * | 12/1999 | Kuczynski et al. ............ 522/31 |
| 6,515,039 | B1 | * | 2/2003 | Ulbricht et al. ................ 506/3 |
| 6,572,980 | B1 | * | 6/2003 | Klemarczyk et al. ......... 428/620 |
| 6,657,031 | B1 | * | 12/2003 | Crane et al. ................... 526/266 |
| 7,109,061 | B2 | * | 9/2006 | Crane et al. .................. 438/118 |
| 2002/0089067 | A1 | * | 7/2002 | Crane et al. .................. 257/778 |

FOREIGN PATENT DOCUMENTS

| CS | 150885 | 9/1973 |
| EP | 0 635 534 | 1/1995 |
| WO | WO 96/02491 | 2/1996 |
| WO | WO 96/31559 | 10/1996 |

OTHER PUBLICATIONS

Johson et al. Synethesis of Photocleavble linear macromolecules by ATRP and Star Macromonomers by Tandem ATRP—Click Reaction:Precursors to photodegradable model networks. Macromolecules, 40 (10), 3589-3598, 2007.*
Madhaven et al. Synthesis and photocleavage of a new dimeric bis(o-nitrobenzyl) diether tether. Chem. Commun., 2004, 2728-2729.*
Johnson et al. Synthesis of Photocleavable Linear Macromonomers by ATRP and Star Macromonomers by a Tandem ATRP-Click Reaction: Precursors to Photodegradable Model Networks. Macromolecules 2007, 40, 3589-3598.*
Donya, A.P. et al., "Synthesis of triazenes and azo dyes from aminostyrenes", Zhurnal Vsesoyuznogo Khimicheskogo Obshchestva im. D.I. Mendeleeva (1974), 19(5), 584-6*.
Kamogawa, H. et al., "Syntheses and properties of photochromic polymers of the azobenzene and thiazine series", J. Polym. Sci., Part A-1 (1968), 6(11), 2967-91.
Lormann, M. et al., "Hydro-dediazoniation of diazonium salts using trichlorosilane: new cleavage conditions for the $T_1$ traceless linker," Tetrahedon Letters (2000), 41(20), 3813-3816.
Nuyken, O. et al., "Laser ablation of arylazo-containing polymers", Polymer News (1999), 24(8), 257-266.
Nuyken, O. et al. "Synthesis of Polysulfides Containing the Triazeno Group and Their Application as Photoresists in Excimer Laser Polymer Ablation", Chemistry of Materials (1997), 9(2), 485-494.
Wei, J. et al., "Novel Laser Ablation Resists for Excimer Laser Ablation Lithography. Influence of Photochemical Properties on Ablation", Journal of Physical Chemistry B (2001), 105(6), 1267-1275.

* cited by examiner

*Primary Examiner*—Sanza L McClendon
(74) *Attorney, Agent, or Firm*—Young & Thompson

(57) ABSTRACT

A photosensitive adhesive composition of the polymerizable resin type, the hardening of which occurs by polymerization and/or reticulation, includes:—initiators for at least one chain polymerization reaction to guarantee the hardening of the composition and a sufficient quantity of at least one bifunctional monomer, including a photolabile center with at least one photolabile entity and at least two polymerizable units, connected by covalent skeletons to the photolabile center and located away from the cleavage sites of the photolabile center, such that the composition loses the integrity and adhesivity thereof under the influence of a reticulating radiation causing the cleavage of the photolabile sites. The composition is particularly of application in dentistry.

51 Claims, No Drawings

PHOTOSENSITIVE ADHESIVE COMPOSITION

The present invention pertains to a photosensitive adhesive composition. It also concerns a method for preparing certain bifunctional monomers that are constituents of this composition, and some of these special monomers.

In the area of dentistry the use of adhesives is well known, such as acrylic resins, used to ensure the fixing of elements onto teeth. For example, for positioning an orthodontic brace, attachments are fixed to the enamel surface of the teeth called brackets which are intended to hold the retaining wire in place. Once correction is completed, these attachments are removed. Removal is generally achieved by traction/twisting using a gripping device. This is often a long and traumatizing operation for young patients and may cause substantial deterioration of the enamel surface that is sometimes irreversible.

Similarly, mechanical deterioration of the supporting tissue is encountered when removing a crown, facet, post or inlay.

An adhesive has therefore been sought which enables two parts bonded by this same adhesive to be separated without any mechanical damage to the surface of said parts. This adhesive would therefore have the particularity of losing its adhesiveness other than through external mechanical action. Preferably, this loss of adhesiveness should be obtained without having recourse to solvents, but rather to un-crosslinking actinic radiation of said adhesive which would be the most suitable for dental applications.

In this respect, U.S. Pat. No. 4,286,047 is also already known published on 25 Aug. 1981 which discloses a pressure-sensitive adhesive whose adhesiveness can be "released on demand" by exposure to UV radiation. The composition of this adhesive firstly comprises acrylate compounds polymerizable per se, which imparts the pressure-sensitive characteristic to the adhesive, and secondly cationic photoinitiators and monomer compounds incorporating oxirane cycles. The photo-initiators are able to initiate the polymerization of the oxirane cycles after UV radiation. This photoinduced polymerization deteriorates the adhesive structure and greatly reduces adhesion to the substrate on which the adhesive composition was applied. This adhesive is preferably used in adhesive tape or film form which is the most appropriate method of application for pressure-sensitive adhesives.

However, said adhesives have the major disadvantage of being mixed with toxic organic solvents (ethyl acetate and isopropanol) which must be evaporated after applying the adhesive composition to its substrate or to the polymer support of the adhesive strip. This operation is inconceivable for dental patients.

Also, the composition disclosed in this patent is difficult to use as such other than in tape or adhesive film form: the immense majority of adhesive applications require a viscous or paste formulation which is much more practical for coating surfaces. Finally, the adhesive strength of the composition previously disclosed does not ensure sufficiently resistant bonding in all cases of utilization.

The purpose of the present invention is to overcome these disadvanatges by proposing a photosensitive adhesive composition of polymerizable resin type whose hardening is obtained by polymerization and/or crosslinking.

For this purpose, and according to the invention, this adhesive composition is remarkable in that it contains:
- means to initiate at least one chain polymerization reaction, to ensure hardening of said composition, and
- a sufficient quantity of at least one bifunctional monomer including firstly a photocleavable centre comprising at least one photocleavable unit, and secondly at least two polymerizable units bound by covalent skeletons to said photocleavable centre and positioned either side of the cleavage site or sites of said photocleavable centre, so that said hardened composition loses its integrity and adhesiveness under the action of uncrosslinking radiation achieving cleavage of the photocleavable units.

In the remainder of this disclosure, the term monomer shall designate both monomers in the strictest sense and oligomers and prepolymers. Similarly, the term polymerization shall systematically denote "chain" polymerization.

According to an essential characteristic of the adhesive composition of the invention, it contains bifunctional monomers whose minimum structure can be described by the following schema:

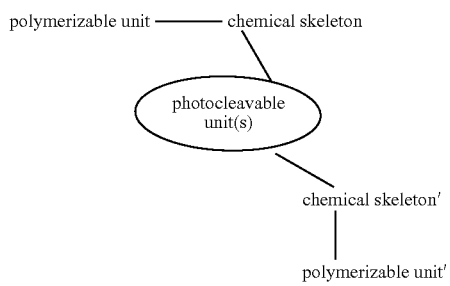

It can be clearly seen that with the adhesive composition of the invention it is possible to obtain a cross-linked polymer containing "padlocks" in its matrix which are the photocleavable centres. Uncrosslinking actinic radiation will open these padlocks by cleaving the photocleavable units leading to loss of crosslinked cohesion and resulting in loss of adhesiveness, since the polymer disintegrates.

According to another characteristic of the composition of the invention, it is in liquid, viscous or paste state at ambient temperature and may also contain chain polymerizable co-monomers which may act as reactive diluent. Therefore, the composition may free from any danger connected with solvent toxicity and is in addition easy to use, its physical properties permitting problem-free coating of the elements to be bonded.

Finally, in a preferred variant of embodiment, the initiation means for the chain polymerization reaction are photoinitiators able to initiate the polymerization mechanism under the action of crosslinking radiation whose wavelength $\lambda 1$ is different to wavelength $\lambda 2$ for uncrosslinking radiation. It will therefore be understood that with a single lamp and adapted filters, the cement can be polymerized very rapidly (a few minutes) and conversely can be uncrosslinked to separate two elements cemented together by the adhesive composition of the invention.

Other advantages and characteristics will be more readily understood from the following description of several embodiments of the photosensitive adhesive composition of the invention; firstly examples will be given of the families of chemical compounds contained in the bifunctional monomers of the invention with examples of synthesis methods for some of these bifunctional monomers. A description will afterwards be given of the possible applicable variants of the type of initiation means for the polymerization reaction. Finally, compositions preferably intended for clinical dental use will be presented as examples.

According to an essential characteristic of the photosensitive adhesive composition of the invention, it contains bifunctional monomers that are polymerizable and photocleavable.

Among all known photocleavable units, consideration will be given to two main families, the aryl-diazos and benzyls.

A first large family of photocleavable units which can be applied is the family of azyl-diazos having the following general structure of formula I:

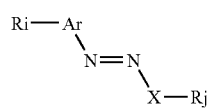

As a general rule, since these compounds are unstable in highly acid or basic media, care is taken that the Ri and Rj substituents do not carry highly acid or basic groups, unless the acidity or baseness is masked by various interactions such as inter- and intramolecular hydrogen bonds for example in the case of acidity or intermolecular bonds existing in the solid state. Also, in the following description of the Ri and Rj substituents, the hydrocarbon groups in particular alkyl, alcoxy, alkylthio, are preferably C1-C6 groups, aryloxy and arylthio are preferably made up of 5 to 14 atoms, preferably 5 to 6 atoms for monomers in their strictest sense, but they may be chains of larger size if oligomers or prepolymers are considered.

These aryl-diazo units are therefore represented by the above formula I, in which:

Ar denotes an aromatic system that is monocyclic or polycyclic, carbocyclic or heterocyclic, including in particular atoms such as S or N, each cycle preferably having 5 or 6 atoms;

X denotes an atom chosen from among: C, N, O, P, S;

Ri is chosen from among the hydrogen, halogen groups, a functional group whether ionic or not (with the exception of halogenated groups able to release strong acids, such as acyl halides), a polymerizable functional group such as those described hereafter. The Ri substituent may also be a radical or a hydrocarbon chain which may be aliphatic, acyclic, saturated or unsaturated, straight or branched, a cyclic aliphatic, unsaturated, aromatic or heteroaromatic radical, all these radicals or chains possibly carrying substituents of Ri type or interrupted by a heteroatom chosen from among B, N, O, Si, P, S, a halogen or a functional group.

The notion of radical is more appropriate for designating a monomer, whilst the notion of chain is better suited for describing a straight, branched or crosslinked polymer in the entire description of the invention.

On the aromatic cycle of the aryl-diazo unit, the Ri substituents may form between themselves a carbocyclic or heterocyclic cycle, whether substituted or not, preferably comprising no more than 6 atoms to form the cycle; the same applies, as a general rule, to substituents, in particular those defined similarly to Ri which may be located on any radical or hydrocarbon chain mentioned in the entire description of the invention.

Ri may, in particular, be one or more groups of the type: alkyl—straight or branched, saturated or unsaturated, optionally substituted, aryl—aromatic or heteroaromatic, substituted or unsubstituted, alcoxy such as methoxy for example or ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group, —OCO$_2$R', —OSO$_2$R', —OPOOR'OR", —R'NHCOOR", —R'OCO$_2$R", —NR'R" (where R' and R" represent an alkyl group, a carbocyclic or heterocyclic group, aliphatic, unsaturated, a (hetero-)aromatic group, all substituted or unsubstituted), imine substituted or unsubstituted, nitro, —N═N—R', -Rp-Si—(ORq)$_3$ group (in which Rp is a hydrocarbon chain, preferably a straight alkyl chain having at least 3 C atoms, and Rq denotes a hydrogen atom, a hydroxy group, an alcoxy C1-C6 chain, or —(Si(ORq)) group), a vinyl group, an acrylic group, an alcoxycarbonyl group or an aryltriazene group, among others.

If the aryl group of an aryl-diazo subunit is monocyclic, the substituent Ri donor groups of the aromatic cycle are preferably at para or ortho of the diazo group and the Ri attractor groups preferably at meta of this group.

Rj designates one or more substituents, according to the valency of the atom designated by X. Generally, the different Rj are the same or different and may designate an alkyl chain straight or branched, aliphatic or unsaturated, acyclic or cyclic, preferably C1-C6, optionally substituted by substituents meeting the definition of Ri for example optionally interrupted by a heteroatom such as N, O, Si, P, B for example, an aromatic or hetoraromatic group including for example in a preferred chain of 5 or 6 atoms at least one nitrogen or sulfur monocyclic or polycyclic atom, an alcoxy chain, aryloxy chain, a benzyl group, the Rj substituents may also form a cycle preferably having 5 to 6 atoms.

In addition, Rj may evidently be the residue of a chain when the bifunctional monomer compound is of polymer or oligomer size. Finally, Rj may advantageously designate a heteroatom such as preferably O, N or P, structurally arranged with X in relation to the possibilities offered by the valency of X.

If X is an atom of carbon C or oxygen O (arylazoalkyl and aryldiazoether compounds respectively), Rj also designates an alkylthio, arylthio chain, a cyclohexyl, naphthyl group, a hydroxyethyl, cyanoethyl, acryloxyethyl group, alkyl (C1-C6)glycidyl ether or alkyl(C1-C6)vinyl ether, a cyclohexyl epoxy, advantageously in the case of aryldiazoalkyls an attractor group such as a cyano, nitro group, carboxylic, sulfonic and phosphoric acid, carboxylic and sulfonic ester, phosphonate, amide, carbonyl.

If X is an atom of phosphorus P, Rj also advantageously jointly designates the groups or atoms such that they create a photosensitive unit of Ar—N═N—PO(OR')(OR")arylazophos-phonate type, in which R' and R" are defined as previously in Ri, in particular R' and R" may independently designate an alkyl chain whether straight or branched, substituted or not, saturated or not, acyclic or cyclic, carbocyclic or heterocyclic, a (hetero)-aromatic radical, more particularly a hydroxyethyl chain, 1,4- or 1,3-dimethylcyclohexyl, 1,4-dimethylparaphenyl, a methyl, ethyl, propyl, isopropyl, hydroxyethyl, cyanoethyl, acryloxyethyl group, an ether of alkyl (C1-C6)glycidyl or alkyl (C1-C6)vinyl, a cyclohexyl epoxy.

Examples of such compounds can be found for example in the article "New arylazophosphonate-containing Polyurethanes and Polyesters for Laser Ablation Structuring", *Macromol. Mater. Eng.*, 2002, 287, 671-683.

If X is an atom of sulfur S, Rj also advantageously and jointly designates the groups or atoms such as to create a photosensitive unit of AR—N═N—SO(OR')(OR")arylazosulfonate type, R' and R" being defined as previously. Rj may also jointly designate the groups or atoms so as to create a photosensitive unit of AR—N=N—SO₂R' arylazosulfone type, or further an Ar—N=N—S—R' arylazosulfide unit.

Finally, if X is an atom of nitrogen N (aryltriazene, arylpentazadiene, arylhexazadiene compounds) consideration is given to the following formula II:

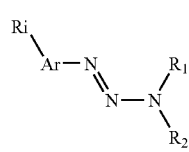

in which Ri is defined as previously and the R1 and R2 substituents correspond to the definition of Rj.

R1 and R2 may advantageously designate, independently from one another, each of the hydroxyethyl, cyanoethyl, aminoethyl, acryloxyethyl or halogenoethyl groups.

R1 and R2 designate the residues of one or two organic compounds, optionally polymers, of which one initially carries at least one primary or secondary amino group at its ends, and independently represent a hydrogen atom (but not the two simultaneously), a functional donor group, an alkyl chain straight or branched, aliphatic, unsaturated, acyclic, cyclic, preferably C1-C6, optionally interrupted by a heteroatom such as N, O, Si, P, B for example, a (hetero)-aromatic group, all these groups or radicals may be substituted by various functional groups such as Ri for example.

The same indications as those given above also apply to the notion of a functional group, with the addition of those concerning the synthesis of the triazene unit. The synthesis schematic of these units is based on (mono/bi)-coupling between a diazonium salt of an aromatic amine and another amine defined by the formulas $NHR_1R_2$ or $NH_2R_1$ and, in the case of monocoupling, is:

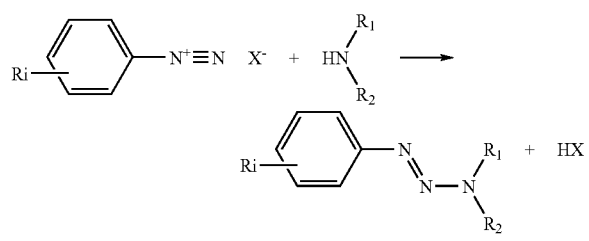

The $R_1$ and $R_2$ substituents are preferably such as the $NHR_1R_2$ or $NH_2R_1$ amine exists in this form or other form in which it is stabilized or made reactive, such as hydrates, ammonium chlorides for example. Preferably $R_1$ and $R_2$ do not designate halogens.

Similar to Ri, $R_1$ and $R_2$ may represent the necessary atoms to complete a cycle. In the composition of the invention use may be made in particylar of aryl-triazene compounds or derivatives in which $R_1$ and $R_2$ are for example a —N=N—R' group, —NR'—N=NR" group, OR group, NR'R" group (R' and R" have the meanings previously given), an alkyl group such as methyl, ethyl, propyl, isopropyl, butyl, tert-butyl, an alcoxy group substituted or unsubstituted, a benzyl group, a (hetero)-aromatic group, all substituted or not by substituents of Ri type, a hydroxyethyl, cyanoethyl, aminoethyl, acryloxyethyl or halogenoethyl group.

Persons skilled in the art will find examples of aryl-triazene compounds applicable to the adhesive composition of the invention in the publications by Oskar Nuyken and/or his team.

Finally, the photocleaving site of the aryl-diazos is generally the —N=N—X— chain of which at least one of the bonds is broken under □2 actinic radiation; in the bifunctional monomers corresponding to the invention, the chemical skeletons binding said unit to the polymerizable units are therefore reasonably arranged either side of the —N=N—X chain.

A second large family of photocleavable units applicable to the adhesive composition of the invention is the benzyl family, having the following general structure of formula III:

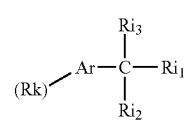

Generally, as for the aryl-diazos, the alkyl, alcoxy, alkylthio substituents are preferably C1-C6, aryloxy and alkylthio preferably have 5 to 14, further preferably 5 to 6 atoms but they may be chains of larger size. Also the Rk, Rl, Rm substituents described below may evidently be the residue of a chain when the bifunctional monomer compound is of oligomer polymer size.

These benzyl units, which have better stability in acid medium than the aryl-diazos, are therefore represented by formula III above, in which:

Ar designates an aromatic or heteroaromatic radical (including an atom such as N or S for example), monocyclic or polycyclic, carrying at least one Rk substituent different to the benzyl substituent explicitly present (nitro for example if nitrobenzyls are considered), Rk is generally one or more substituents of the aromatic cycle, and designates an auxochromic or bathochromic substituent possibly chosen from among the following examples: hydrogen, halogen, alkyl chain, aliphatic, acyclic saturated or unsaturated, straight or branched, a cyclic radical whether aliphatic, unsaturated, aromatic or heteroaromatic (these chains and radicals may be substituted, interrupted or terminated by a heteratom such as B, N, O, Si, P, S or a halogen), a nitro, cyano, alcoxy, aryloxy, alkylthio, arylthio, benzyl, arylalkyl, hydroxy, thiol, alkyloxycarbonyl, aryloxycarbonyl, carbonyl, formyl, amino group, carboxylic and sulfonic ester, carboxylic sulfonic and phosphoric amide, carboxylic sulfonic and phosphoric acid, sulfonate, phosphonate, a —OCONR'R", —OCO₂R', —OSO₂R', —OPOOR'OR", —R'NHCOOR", R'OCO₂R", NR'R" group (R' and R" are an alkyl, aryl group, a carbocyclic or heterocarbocyclic group), imine substituted or unsubstituted, diazo —N=N—R', a -Rp-Si—(ORq)₃ group (Rp and Rq as defined for the aryl-diazos), ether of alkyl(C1-C6)glycidyl or alkyl(C1-C6)vinyl, cyclohexyl epoxy.

$R_{11}/R_{12}/R_{13}$ designate a hydrogen, an alkyl, alcenyl, alcynyl, alkylaryl chain, substituted or unsubstituted, preferably C1-C6, a carbocyclic or heterocyclic chain, saturated or unsaturated, aromatic or heteroaromatic, substituted or not, preferably having 5 to 6 atoms, an alcoxy, aryloxy, alkylthio, arylthio chain, an alkyloxycarbonyl group, —NR'COR" group, —OCOR' group, —OCOOR' group, —OCONR'R" group, NR'COOR" group, —OPOR'R"R'" group, —OSO$_2$R' group, —OPOOR'OR" group, —NR'R" group, —COOR' group, —CONR'R", SOOR', —COR' group (R', R", R'" have the previously indicated denotations), an imine group substituted or not, hydroxy, thiol, a carboxylic acid or derivative, a halogen, nitrile, an alkyl(C1-C6) glycidyl or alkyl(C1-C6)vinyl ether, cyclohexyl epoxy, -Rp-Si(ORq)$_3$ group (Rp and Rq as defined previously).

Persons skilled in the art will for example find examples of compounds meeting the definition of formula III in the publication "Photosensitive protecting groups" Israel J. of Chem., 1974, 12(1-2), pp. 103-113.

Generally, the photocleaving site of benzyls is the benzyl carbon explicitly present in formula III of which at least one of the bonds with one of the $R_{11}/R_{12}/R_{13}$ groups is ruptured under λ2 actinic radiation; in the corresponding bifunctional monomers of the invention, the chemical skeletons binding said unit to the polymerizable units are therefore reasonably arranged either side of the benzyl carbon under consideration.

One category of benzyl units applicable to the invention which is particularly efficient and does not comprise any nitro function explicitly at the ortho position of the benzyl function, are the benzyl units in which Ar is at least bisubstituted at the meta of the benzyl function by an alcoxy or aryloxy chain and in which two of the $R_{11}/R_{12}/R_{13}$ substituents are a hydrogen atom or an alkyl group, preferably C1-C4, preferably at least one of the two substituents being an alkyl group, while the last substituent is a chain starting with a heteroatom such as O or N for example or a functional group of ester or carbamate type.

Also, the best preferred forms of these benzyl units are the 2-nitrobenzyl derivatives, of which some are given in U.S. Pat. Nos. 5,600,035 and 6,100,008, which can be given by the following general formulas:

Formula 1:

$$O_2N-Ar-\underset{Rm_2}{\underset{|}{CH}}-Rm_1$$

in which:
AR is as previously defined;
$R_{m1}/R_{m2}$ are defined as $R_{11}/R_{12}/R_{13}$.

Formula 2:

$$O_2N-Ar-\underset{Rm_4}{\underset{|}{CH}}-O-Rm_3$$

in which:
Ar is defined as previously,
$R_{m4}$ is defined as $R_{11}/R_{12}/R_{13}$,
$R_{m3}$ is defined as a hydrogen, an alkyl, alcenyl, alcynyl, alkylaryl chain, substituted or not, interrupted by a heteroatom such as N, O, P, Si, S, preferably C1-C6, a carbocyclic or heterocyclic chain, (un)saturated, (hetero)-aromatic, substituted or not, preferably 5 to 6, an alkyloxycarbonyl group, POR'R"R'" group, —SO$_2$R' group, —POOR'OR" group, —COOR' group, —CON'R", a COR' group (R', R" and R'" having the denotations given previously for R' and R"), alkyl(C1-C6)glycidyl or alkyl(C1-C6)vinyl ether, cyclohexyl epoxy, (Rp-Si(ORq)$_3$ group (Rp and Rq as previously defined).

Formula 3:

$$O_2N-Ar-\underset{Rm_5}{\underset{|}{CH}}-N\underset{Rm_7}{\overset{Rm_6}{\diagup}}$$

in which:
Ar is defined as previously,
$R_{m5}$ is defined as $R_{11}/R_{12}/R_{13}$,
$R_{m6}/R_{m7}$ are defined as a hydrogen, an alkyl, alcenyl, alcynyl, alkylaryl chain, substituted or not, interrupted by a heteroatom such as N, O, P, Si, S, preferably C1-C6, a carbocyclic or heterocyclic chain, (un)saturated, (hetero)-aromatic, substituted or not, preferably having 5 to 6 atoms, an alkyloxycarbonyl group, —R'COR" group, R'COOR" group, R'R", —COOR' group, —CONR'R", a COR' group (R' and R" having the denotations previously given), a hydroxy group, alkyl(C1-C6)glycidyl ether or alkyl(C1-C6)vinyl ether, cyclohexyl epoxy, -Rp-Si(ORq)$_3$ group (Rp and Rq as defined previously).

Formula 4:

$$O_2N-Ar-\underset{Rm_8}{\underset{|}{CH}}-CH\underset{Rm_{10}}{\overset{Rm_9}{\diagup}}$$

in which:
Ar is defined as previously,
$R_{m8}/R_{m9}/R_{m10}$ are defined as $R_{11}/R_{12}/R_{13}$.

Among all the photocleavable units presented above, particular preference is given to arylazophosphonates, arylazosulfonates, arylazosulfides, aryltriazenes and 2-nitrobenzyls for their proven cleaving efficacy, the involved wavelengths, their stability in the adhesive composition of the invention and more particularly, for the 2-nitrobenzyls, their commercial availability and their better stability in acid medium, which may prove to be essential in some considered applications.

According to an essential characteristic of the invention, the bifunctional monomers used contain units that are polymerizable through chain polymerization reaction. This reaction may be conducted by three processes well known to persons skilled in the art: radical, cationic or anionic.

In a first variant the polymerization process is radical. The polymerizable units selected for radical polymerization are vinyl units. These are described as follows:

$$\underset{R_3}{\overset{}{\diagdown}}C=C\underset{R_4}{\overset{R_5}{\diagup}} \qquad IV$$

in which $R_3$, $R_4$ and $R_5$ are substituents able to activate together the double vinyl bond vis-à-vis radical addition chain reactions. At least one of these substituents is a hydrocarbon chain, optionally interrupted by a functional group such as Ri or a heteroatom such as N, O, Si, P, S substituted or not by groups such as Ri, linked to at least one photocleavable unit so as to meet the structural criteria of the bifunctional monomers of the invention. More generally, $R_3$ or $R_4$ or $R_5$ may represent a hydrogen atom, a halogen atom, a functional group, an alkyl, alcoxy, chain saturated or unsaturated, substituted or not, preferably C1-C6, or an aryl, aryoxy group substituted or not preferably having 5 to 6 atoms, an attractor functional group such as a carbonyl group, a carbonyloxyalkyl or carbonyloxyaryl group, an amide group, cyano group, optionally a sulfonic carboxylic acid group, and their salts, with optional appropriate restrictions or exclusions to preserve compatibility with the photocleavable units, or further an alcoxycarbonyl group.

To obtain good reactivity in respect of radical polymerization, persons skilled in the art may, without limiting the invention, select at least one of the substituents from among the cited attractor groups to create (meth-)acrylic units for example.

As non-restrictive examples, below are given some structures which require structural modification for their linking to a photocleavable unit using one of the methods explained below or using techniques known to persons skilled in the art:

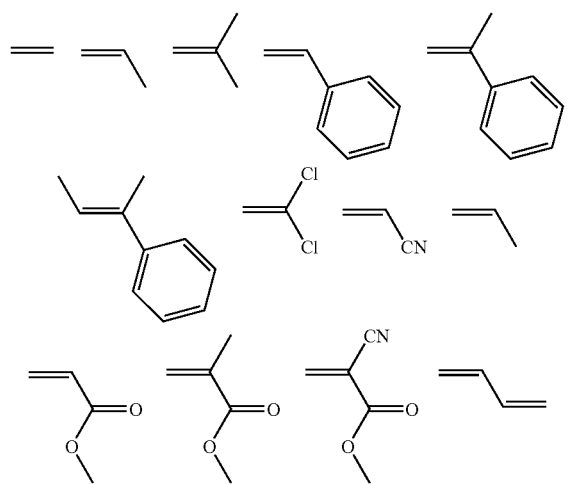

In one alternative embodiment of the composition of the invention, electron acceptor vinyl units may coexist in the composition that are able to create a charge transfer complex with at least one other complementary partner, this other partner itself, in a certain number of cases, possibly being a vinyl unit that will be an electron donor. The charge transfer complex is then able to initiate the radical polymerization reaction under radiation of wavelength λ1. In particular, it is possible to choose an electron donor unit from among the following examples: styrene, cyclohexane oxide, vinyl acetate, vinyl ether, phenyl glycidyl ether, exomethylene dioxolane such as 4-methylene-2-phenyl-1,3-dioxolane, alkyl methacrylate, vinyl pyrrolidone, and an electron acceptor unit among the following examples: maleic anhydride, acrylonitrile, diethyl fumarate, fumaronitrile, maleimides.

In the second variant of polymerizable units applicable to the composition of the invention, the polymerization process is cationic. A cationically polymerizable unit is a unit which polymerizes or crosslinks in the presence of an acid or cation.

Such units may be chosen from among the following families: epoxide (or oxirane), oxetane, oxolane, cyclic acetal, cyclic lactone, thiirane, thietane, vinyl ether, cyclic ether, cyclic thioether, spiroorthoester, spiroorthocarbonate, aziridine, siloxane, styrenes.

With a view to photoinduced polymerization in particular (cf. description of initiating means hereafter), preference is given to oxirane units whose structure is defined by following formula V:

V in which $R_6$, $R_7$, $R_8$, $R_9$ are the same or different, at least one of the substituents $R_6$, $R_7$, $R_8$, $R_9$ being a hydrocarbon chain, and generally represent an atom of hydrogen, halogen, an alkyl, alcoxy, alkylthio chain, straight or branched, saturated or unsaturated, acyclic or cyclic, preferably C1-C6, optionally substituted, optionally interrupted by a heteroatom, an aromatic or heteroaromatic aryl group, an aryloxy or arylthio group preferably having 5 to 6 atoms, a benzyl group, an imine group, NR'R" amino NR'R", SiR'R"R''', alkyl(C1-C6)oxycarbonyl, aryl(C1-C6)oxycarbonyl, amide, carboxylic and sulfonic ester, sulfonate, phosphonate, a carbonyl, cyano group, —OCONR'R" group, —OCO$_2$R', —OSO$_2$R', —OPOOR'OR", —R'NHCOOR", R'OCO$_2$R" in which R, R', R" represent an alkyl group (preferably C1-C6) substituted or not, aryl (preferably with 5 to 6 atoms), a carbocyclic or heterocyclic group, aliphatic, unsaturated or aromatic, substituted or unsubstituted.

Advantageously, for reasons of steric hindrance, two of the substituents R6, R7, R8, R9 are a hydrogen atom.

Typical derivatives are for example the derivatives of diglyceride ether or of 3,4-epoxycyclohexyl.

A further particularly preferred family of units, with a view to photo-induced cationic polymerization, is the family of units of vinyl ether type whose structure is defined by formula VI:

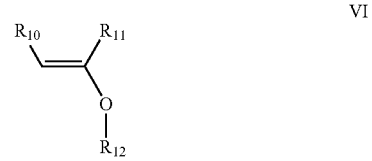

VI in which:
R10 and R11 are the same or different and designate a hydrogen atom or advantageously a straight or branched C1-C6 alkyl chain, substituted or not, saturated or unsaturated, acyclic or cyclic, optionally interrupted by a heteroatom such as O, N, Si, P for example, an aromatic or heteroaromatic aryl group (preferably having 5 to 6 atoms), an alcoxy chain (preferably C1-C6), an akylthio chain (preferably C1-C6), arylthio (preferably having 5 to 6 atoms);

R12 advantageously designates a straight or branched C1-C6 alkyl group, substituted or not, saturated or unsaturated, acyclic or cyclic, optionally interrupted by a heteroatom such as O, N, S, Si, P for example, an aromatic or heteroaromatic aryl group (preferably having 5 to 6 atoms).

Finally, among other examples of ethylene functions that are cationically polymerizable, a choice may be made from among styrene derivatives in particular such as styrene, para-alkoxystyrene derivatives, para-chloromethylstyrene, vinyl toluene, α-methylstyrene.

In a third variant, polymerization is anionic. Among the anionically polymerizable units, units of vinyl type may be chosen (according to formula IV) but which carry electro-attractor substituents such as carboxylic ester in particular (methacrylic derivatives for example), or cyano, or which carry substituents permitting strong positive polarization of the carbon at β of the double bond when approaching the nucleophilic species, such as is the case for example with units of butadiene, styrene, vinylpyridine type.

Heteroaromatic cycles may also be chosen such as those described for cationic chain polymerization, in particular oxirane, thiirane, lactones, lactames.

A method is described below for preparing bifunctional monomers grouping together the minimum structural criteria required for producing a photosensitive adhesive composition of the invention. This method comprises several steps, namely a first step to produce a photocleavable unit or group of units of aryl-triazene or 2-nitrobenzyl type, optionally followed by a structural arrangement step of the skeleton of the photocleavable unit, and a last step during which this photocleavable unit is attached to one or more polymerizable functions via a chemical skeleton.

I—FIRST STEP: SYNTHESIS OF PHOTOCLEAVABLE UNITS

Case 1: Fabrication of an Aryltriazene Unit.

Two principal implementation modes can be considered.

1.—First Implementation Embodiment

1°) Firstly diazotization is conducted of an arylamine (this term encompasses (hetero)-aromatic structures optionally pluri-substituted by —NH$_2$ amino groups without excluding any other substituent of Ri type, such as defined above) in a non-oxidizing aqueous acid medium to form the corresponding diazonium salt. Diazotization is achieved by dissolving the arylamine in an aqueous mineral acid, such as concentrated HCl or H$_2$SO$_4$ for example, and adding thereto, at a temperature of between −10° and 30° C., an aqueous solution of nitrite ions. The solution of diazonium salt obtained is then used either as such, or after modification using known means for the preparation of the diazonium salt of arylamine with a different anion, as is the case if a diazonium chloride is cold precipitated through the addition of an appropriate quantity of tetra-hydroborofluoric acid (HBF$_4$). In similar manner, salts of hexafluorophosphate can be prepared (anion PF6$^-$), of tetra(pentafluorophenyl)-borate (anion B(C$_6$F$_5$)4$^-$), or salts of hexafluoroantimonate (anion SbF$_6^-$).

2°) The diazonium salt, in its initial or "exchanged" form, is then dissolved in an aqueous solution, over the same temperature range as previously, and the pH is adjusted in an alkaline range to achieve diazoic mono- or bi-coupling with at least one of the primary or secondary amino sites of an organic compound.

For this purpose, the compound carrying amino groups is dissolved in an aqueous solution, preferably of pH 7 to 8, or in an organic solvent (alkane, THF, acetonitrile) to which is added a diazonium salt at a temperature of between −10° C. and +30° C.

At the end of the reaction, the triazene compound obtained is isolated using any known technique depending upon chemical structure. In a biphase medium the products may be isolated by simple filtration, otherwise the products may be subsequently purified for example by re-crystallization and column chromatography.

2.—Second Implementation Embodiment

Another preparation method consists of obtaining a diazonium salt from an arylamine able to undergo diazotization in an organic medium such as ethyl ether, THF for example or dry halogenated solvents such as dichloromethane or chloroform. Diazotization is conducted at a temperature of between −50° C. and +30° C. by adding to a solution of arylamine with a Lewis acid such as BF$_3$, PF$_5$, SbF$_5$ for example, a solution of organic nitrite such as tert-butyl nitrite for example. The salt is then extracted using conventional means, in particular by washing and filtering.

Diazoic coupling is then performed by adding to the recovered diazonium salt, dissolved in an inert dispersing solvent, a solution of an organic compound carrying at least one primary or secondary amino group, this reaction being conducted at a temperature of between −50° C. and +50° C. in the presence of a base which is preferably sodium or potassium carbonate. The aryl-triazene unit obtained is isolated using known techniques. It is to be noted that only the diazotization method undergoes change, diazoic coupling also possibly being conducted as indicated under I.1.2°).

Case 2: Fabrication of a 2-nitrobenzyl Unit

The synthesis variants are numerous, two important distinctions exist depending on whether the nitration of an aromatic cycle is necessary or not to arrive at a specific 2-nitrobenzyl structure (this depends upon source commercial products).

1. First Implementation Embodiment: Nitration

1°) A first structure type is created by nitrating benzyl compounds substituted in a form able to promote nitration at least at the ortho position of the benzyl group. Said nitration can be conducted under conditions known to persons skilled in the art, which are the use of dilute or concentrated nitric acid, either alone or combined with concentrated sulfuric acid, acetic anhydride or the use of a nitronium salt (NO$_2$BF$_4$, NO$_2$CF$_3$SO$_3$ for example in aprotic organic solvents), or of nitrites (for example NaNO$_2$ in the presence of trifluoroacetic acid), or esters of nitric acid (ethyl nitrate for example used under alkaline conditions or with a Lewis acid), or N$_2$O$_5$ in CCl$_4$ in the presence of P$_2$O$_5$ in an anhydrous medium under conditions of temperature or time suitable for the reactivity of the aromatic cycle.

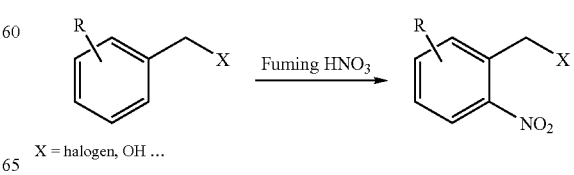

X = halogen, OH ...

2°) A second type of structure is created by nitrating benzene compounds of which at least one nitratable position is adjacent to a precursor function of a substituted methylene. Among these functions, the reducible functions (aldehyde, ketone, amide, carboxylic acid, nitrile, imine, hydrazone, oxime, epoxide . . . ) are preferred functions, the reducing of said function to be conducted under conditions in which an aromatic nitro group is preserved; therefore the concomitant use is excluded of metals and acid (for example Zn and HCl), of catalytic hydrogenation conditions, of $AlH_3$—$AlCl_3$, $TiCl_3$, $LiALH_4$, $NaBH_4$+$NiCl_2$ ($PPh_3$), $NaBH_4$+$CoCl_2$.

2. Second Implementation Embodiment: No Nitration

A third type of structure is created by modifying o-nitrotoluene derivatives. Suitable techniques known to persons skilled in the art are bromation of an o-nitrotoluene for example in the presence of N-bromosuccinimide or the treatment in polar organic solvent (such as DMSO for example) of derivatives of o-nitrotoluene with paraformaldehyde in the presence of strong bases (such as KOH, tertiobutylate potassium, Triton B, DBU, guanidines for example) to arrive at derivatives of 2-(nitrophenyl)ethyl.

II—SECOND STEP: STRUCTURAL ARRANGEMENT

Generally, when the skeleton of the photocleavable unit obtained after the first step has functions capable of directly fixing a polymerizable unit such as defined in the invention, it is not essential to modify the chemical structure of this skeleton, and in this case this step is omitted to pass directly to step three. If not, persons skilled in the art are able to implement the necessary reactions to achieve fixing of this polymerizable unit during the third step of the method.

III—THIRD STEP: ASSOCIATION OF POLYMERIZABLE UNITS WITH PHOTOCLEAVABLE UNITS

Case 1: Polymerizable Units of Vinyl Type

Here consideration will be given to all the vinyl units previously described, namely those that can be radically polymerized (formula IV), cationically polymerized (vinyl ethers of formula VI and styrene derivatives) or anionically polymerized.

Starting with the chemical structure surrounding the photocleavable unit or units, there are two variants for associating vinyl units with photocleavable units. A first variant to elongate the skeleton and include therein one or more vinyl polymerizable functions, is a process during which the vinyl function is created.

The other variant consists of grafting pre-existing vinyl units.

1°) First Variant: Creation of the Vinyl Function

This preferably involves creating a vinyl function of acryloyl type illustrated below in the case of a photocleavable unit of aryl-triazene type.

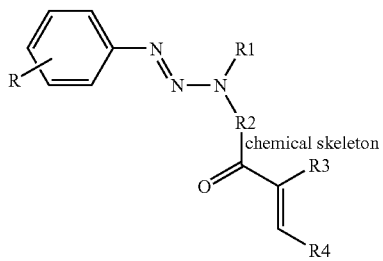

This variant for creating the acryloyl function consists of using a reaction of nucleophilic substitution type on an acryloyl carbon. Different nucleophilic agents can be used, a distinction being made if necessary between possibilities applicable to aryl-diazos, in particular arylazophosphonates and aryltriazenes, and to benzyls in particular 2-nitrobenzyls.

1°)1) The Nucleophilic Agent is an O—R Group as is the Case for:

a) attack by an alcohol or alcoholate on acryloyl halides, preferably conducted in the presence of a base such as pyridine;

b) attack by an alcohol on an acryloyl anhydride, preferably catalyzed by a base such as pyridine of 4-(N,N-dimethylamino)pyridine (DMAP);

c) attack by an alcohol on an acrylic acid.

for aryl-diazos: esterification reactions abound in the literature and persons skilled in the art may refer thereto with the reservation that esterifications are excluded which are conducted under conditions of acid catalysis. The preferred conditions include activations of acid functions into ester functions of 2-pyridinethiol, in the presence of 1-methyl-2-chloropyridinium iodide, in the presence of dehydrating agents particularly chosen from the group: dicyclohexylcarbodiimide (DCC), diisopropylcarbodiimide (DIPC) combined with 4-methylamino-pyridinium tosylate (DPTS), N,N'-carbonyldiimidazole, 1,1'-carbonylbis(3-methylimidazolium), alkylchloroformate and triethylamine, di-2-pyridylcarbonate, di(2-pyridyl)-dithiocarbonate, 1-hydroxybenzotriazole, penta-fluorophenyl diphenylphosphate, diethylazodicarboxylate and triphenyl phosphine, Amberlyst-15, for benzyls: on account of their better stability in acid medium, in addition to the attack methods given above for aryl-diazos, well-known methods may be used such as acid catalysis ($H_2SO_4$, sulfonic para-toluene acid), distillation and/or azeotropic distillation.

d) attack by an alcohol on an acrylate (transesterification reaction):

for aryl-diazos: the embodiments containing acid catalysis are to be excluded: on the other hand, the preferred treatment modes include transesterification reactions in the presence of catalysts such as titanates, tin oxides and esters such as $Bu_2Sn(OMe)_2$, $(Bu_2SnCl)_2O$, dibutyl tin dilaurate, $BuSn(O)OH$, or further $Zn(CH_3COO)_2$. Consideration may also be given to conditions of basic catalysis in the presence of triethylamine or 1,8-diazabicyclo[5.4.]undec-7-ene;

for benzyls: in addition to the reactions set forth above, transesterifications under acid catalysis are possible; as catalyst, special mention is made of sulfonic para-toluene acid, sulfuric acid, boric acid, (pyro)phosphoric acid, phosphonic acid, exchange resins such as DOWEX 50×2-100.

1°)2) The Nucleophilic Agent is an —OCOR Oxycarbonyl Group, as is the Case for:

the attack by salts of carboxylic acids on acryloyl halides in the presence of pyridine or triethylamine or of exchange resins carrying tertiary amino or quaternary ammonium groups, of Lewis acids such as $FeCl_3$, $AlCl_3$ or a combination of these elements.

1°)3) The Nucleophilic Agent is a —S—R Group, According to Embodiments Similar to Embodiments 1°1)a), 1°1)b), 1°1)c) and 1°1)d).

1°)4) The Nucleophilic Agent is a $NR_2$ Group as is the Case for:
  a) attack by an amine according to an embodiment 1°1)a);
  b) attack by an amine according to an embodiment 1°1)b);
  c) attack by an amine according to an embodiment 1°1)c),
in particular the embodiments in the presence of a dehydrating agent such as salts of pyridinium, of $Bu_3N$, or reactions conducted in the presence of $Ti(OBu)_4$;
  for benzyls: consideration may also be given to hot treatment with acrylic acid in the presence of amides of carboxylic or sulfonic acids, treatment in the presence of trialkylaminoborane, in the presence of Lewis acids in particular such as $FeCl_3$, $ZnCl_2$, potassium, sodium or ammonium dihydrogen phosphate, $BF_3\text{-}Et_2O$;
  d) attack by an ammonium salt of a primary amine with an acrylamide optionally in the presence of complexing agents such as $BF_3$;
  e) attack by an amide on an acryloyl halide in the presence of a base such as pyridine.

1°)5) The Nucleophilic Agent is a —NHCOR Group as is the Case for Attack by an Amide on an Acryloyl Halide According to an Embodiment 1°1)a).

2°) Second Variant: Grafting of Vinyl Units

In some embodiments of the invention, the polymerizable vinyl unit is already present in its appropriate form in the molecule which grafts itself onto the photocleavable unit.

For this purpose, depending upon the type of vinyl unit, various methods may be used. However, having regard to the first mode of attachment of the acrylic function described above, the invention comprises a general mode for grafting the vinyl function via all the mechanisms set forth in the first mode of attachment, during which the acrylic function was created. This general mode assumes the reaction between a molecule or an organic macrochain preferably having at one or more of its ends one or more vinyl functions in a form that is the same as the one located within the desired structure of the photosensitive monomer, and having at another end a reactive F1 function and a molecule or pre-synthesized macrochain carrying one or more aryl-diazo or benzyl units linked by various chemical skeletons, and on at least one end a reaction function F2. (F2 is antagonist of F1 according to the first mode of attachment of an acrylic function, i.e. under the conditions described above, F1 and F2 may react to form a covalent F1-F2 bridge).

A molecule including an aryl-triazene unit, linked by a suitable chemical skeleton to a —OH hydroxyl function, can for example be caused to react with a molecule having on its ends a polymerizable olefin function and a carboxylic acid function in the presence of a carboxylic acid function activator (DCC) used to graft the carboxylic acid onto the hydroxyl function.

In addition to all the grafting modes derived from the mechanisms described above under 1°) for the first attachment mode of the acryloyl function, two other types of reactions may be added.

2°)1) Formation of Carbamate Type Links, as is the Case for:
  a) attack by a nucleophil on an isocyanate or isothiocyanate, giving urethane or urea links for example in the case of attack on an isocyanate by an alcohol or an amine respectively. Said reaction may be commonly catalysed by catalysts such as DABCO or metal-containing catalysts such as: $Bu_2Sn(OMe)_2$, dibutyl tin dilaurate, $BuSn(O)OH$ or $Zn(CH_3COO)_2$ for example.
  b) The reaction of phosgene derivatives, such as a ROCOCl chloroformiate on an alcohol or an amine or another nucleophilic group. In this case a carbonate or urethane may be obtained according to a preferred nucleophilic catalysis mode as in 1°1)b).
  c) Reactions of transesterification type conducted between a nucleophilic attacker of alcohol or amine type for example on a carbamate precursor of phenylcarbonate or phenylurethane type for example, said reaction being preferably catalyzed in the presence of a catalyst of the type cited previously under 2°)1)a).

2°)2) Formation of β-hydroxyester Links
such as those obtained in particular by nucleophilic attack by a carboxylate anion on an oxirane; this reaction preferably being conducted under nucleophilic catalysis in the presence of catalysts such as triethylamine, N-methylmorpholine, N-methyl-pyrrolidine, N,N-dimethylbenzylamine, ion exchange resins carrying tertiary amine or quaternary ammonium sites and more particularly referenced as weak and/or strong base anion exchange resins such as Dowex 44, these catalysts being used either alone or in the presence of co-catalysts such as a Lewis acid, for example $FeCl_3$ or $CrCl_3$, or of $Zn(OOC\text{—}C_7H_{15})_2$ or $BF_3O(C_2H_5)_2$ type, however acid catalysts may be considered for o-nitrobenzyls (for example trifluoroacetic acid).

Case 2: Polymerizable Units of Oxirane Type

Here consideration will be given to all the above-described oxirane units, namely those which can be cationically polymerized (formula V) and anionically polymerized.

As for the vinyl units, the two variants for linking an oxirane unit to a photocleavable unit are either the creation of an oxirane unit on the skeleton of the photocleavable unit, or grafting.

1°) First Variant: Creation of an Oxirane Function

One first way of creating an oxirane function consists of treating a halohydrine function according to a nucleophilic substitution method of second order, using a base such as NaOH for example in the presence of water or dimethylsulfoxide for example. The dehydration may also be performed of a 1,2-diol function by treatment with DMF dimethylcetal or diethyl azodicarboxylate in the presence of $PPh_3$.

A second method, preferably applied to units of benzyl type for which it is a method of choice, consists of epoxidation of an olefin in the presence of a peroxydic reagent, among which preference is given to m-chloroperoxybenzoic acid or 3,5-dinitroperoxybenzoic acid. The use of hydrogen peroxide or tert-butyl hydroperoxide in the presence of an alkaline solution or the use of Triton B ($PhCH_2N^+Me3OH^-$) is also a preferred manner for benzyl or aryltriazene substrates, or further the treatment of olefins with an alkyl peroxide and catalyzed by a Vanadium, Titanium or Cobalt complex. For benzyl units having at one end of the chemical skeleton a unit of allylic alcohol type, it is possible to conduct synthesis of an oxirane function in the presence of tert-butyl hydroperoxide, titanium tetraisopropoxide and a dialkyl tartrate under Sharpless conditions, or further with the combination of $Re_3O$/bis(trimethylsilyl) peroxide/$H_2O_2$.

A third manner applicable to benzyl and aryldiazo photocleavable units is the treatment of an alcoholate or phenate, generated at one end of the skeleton linked to the photocleavable unit, with an epihalohydrine or any similar derivative. A derivative method is treatment of a carboxylic acid, or preferably its salt—sodium for example, or any other equivalent function such as sulfonic acids for example, with an epihalohydrine in the presence of quaternary ammonium salts for example such as benzyltrimethylammonium chloride or further in the presence of ion exchange resins referenced as weak base/high base anion exchange resins.

A fourth manner applicable to photocleavable benzyl and aryldiazo units, preferably to aryltriazenes, is treatment of an aldehyde or ketone having at least one end of the skeleton linked to the photocleavable unit by a sulfur ylide such as dimethyloxosulfonium methylide or dimethylsulfonium methylide.

2°) Second Variant: Grafting of Oxirane Units

Several, non-limitative, examples are given below to conduct this grafting.

One first example, set forth above under 1°) but applicable here since it involves destruction of an oxirane function, that is present on a reagent, for its subsequent re-creation during the reaction, is the treatment of an alcoholate or phenate, generated on at least one end of the skeleton linked to the photocleavable unit, with an epihalohydrine. The alcoholate may be generated for example in the presence of sodium hydride or by using solutions, in particular aqueous solutions of NaCH or KOH, in the optional presence of a tertiary amine (for example triethylamine, tributylamine) or an ammonium salt (tetrabutylammonium bromide for example) or an ion exchange resin. A derivative method is the treatment of a carboxylic acid or preferably its salt, sodium for example, or any other equivalent function such as sulfonic acids for example, with an epihalohydrine in the presence of quaternary ammonium salts for example, such as benzyltrimethylammonium chloride, or of ion exchange resins referenced as weak base/strong base anion exchange resins.

A second method consists of treating an alcohol with epichlorhydrine, or any epihalohydrine or any 1,2-epoxy derivative, in the presence of a catalyst of aluminium trialkoxide type, preferably C1-C4, or of aluminium isopropoxide type for example and of an acid co-catalyst such as $H_2SO_4$ for example followed by removal under alkaline conditions.

A third manner is the treatment of an alcohol with an epihalohydrine in the presence of $ZnCl_2/H_2SO_4$ or $ZnCl_2/BF_3,Et_2O$ followed by removal under alkaline conditions. $SnCl_4$ or $BF_3,Et_2O$ are also reagents which can be used under similar conditions.

A fourth manner is the treatment of benzyl halide groups (carried by the skeleton of the photocleavable unit) with glycol or its derivatives in the presence of a hydride, in particular sodium hydride, in a solvent such as THF, acetonitrile or DMF, optionally in the presence of a quaternary ammonium salt such as tetrabutylammonium iodide for example.

Below are given some examples of bifunctional monomers incorporating photocleavable and polymerizable units which meet the above cited definitions and are synthesized according to any of the aforesaid techniques.

| Structure | Name | Ref |
|---|---|---|
| | 1,2-Bis[1-(4″-methacrylatemethyl-)-phenyl-3-methyl]triaz(1)ene-ethane | AT1 |
| | 1,2-Bis[1-(4′-(methacrylate-ethyl)aminocarbonyloxymethyl)phenyl-3-methyl-]-triaz(1)ene-ethane | AT2 |

-continued

| Structure | Name | Ref |
|---|---|---|
| 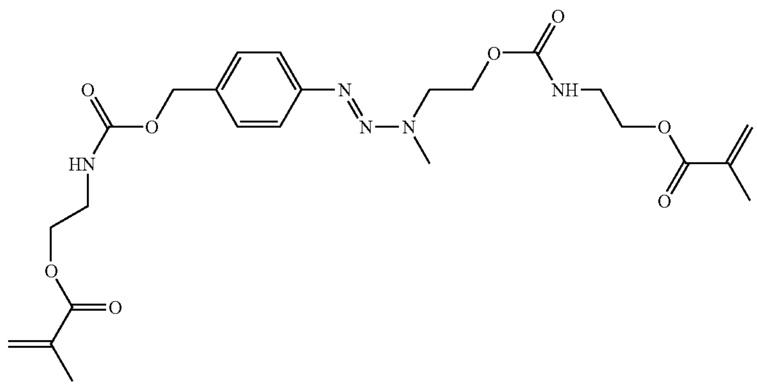 | 1-(4'-(methacrylate-ethyl)aminocarbonyloxy-methyl)phenyl-3-((methacrylate-ethyl)aminocarbonyloxy-ethyl)-3-methyl-triaz(1)ene | AT4 |
| 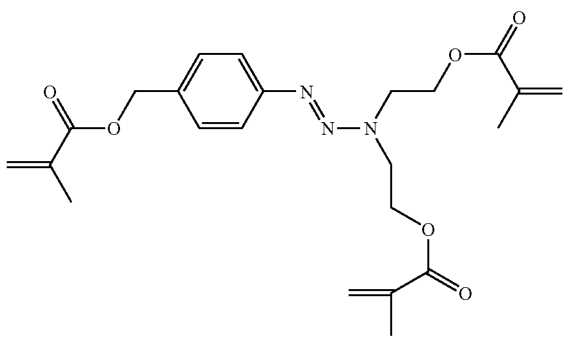 | 1-(4'-methacrylatemethyl-)-phenyl-3,3-di(2''-methacryolylethyl)-triaz(1)ene | AT5 |
| 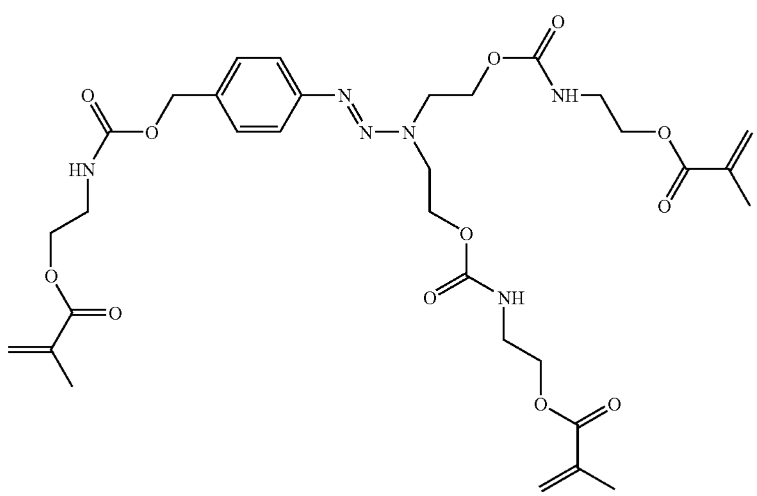 | 1-(4'-(methacrylate-ethyl)aminocarbonyloxy-methyl)phenyl-3,3-di(((methacrylate-ethyl)aminocarbonyloxy-ethyl)-triaz(1)ene | AT6 |
| 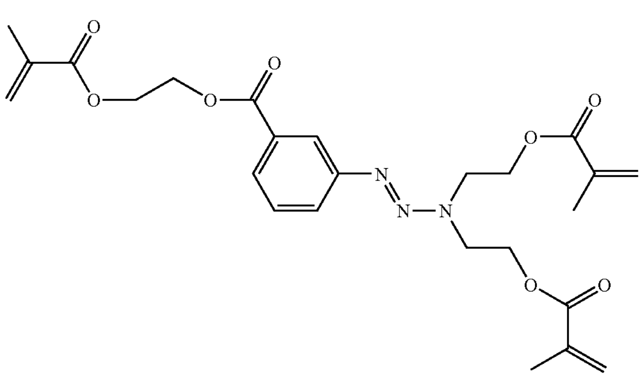 | 1-(3'-(methacrylate-ethyl carboxyphenyl)-3-di(2''-methacrylate-ethyl)triaz(1)ene | AT7 |

-continued

| Structure | Name | Ref |
|---|---|---|
| 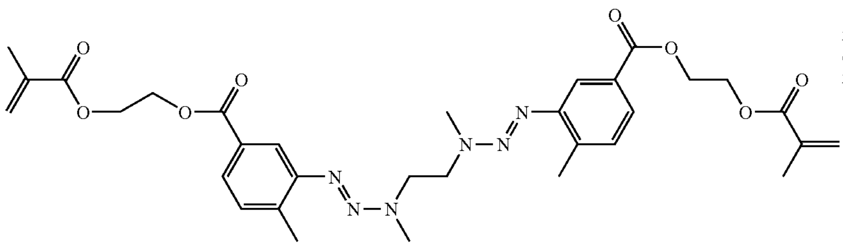 | 1,2-Bis[1-(3''-methacrylate-ethylcarboxyphenyl)-3-methyl]triaz(1)ene-ethane | AT8 |
| 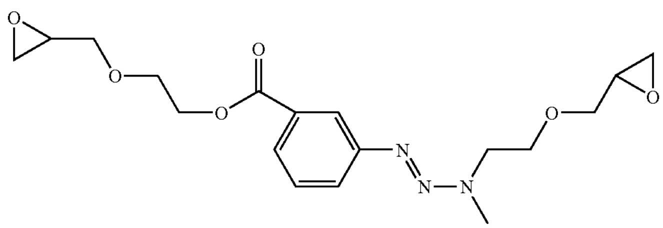 | 1-(3'-ethyl glycidyl ether carboxyphenyl)-3-(ethyl glycidyl ether)-3-methyl-triaz(1)ene | AT9 |
| 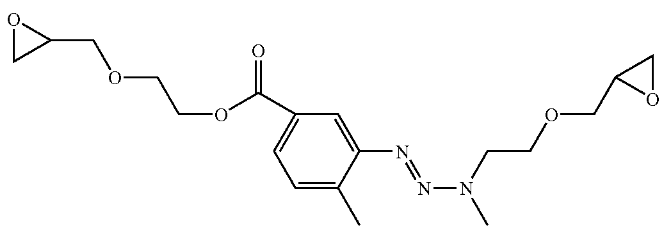 | 1-(3'-ethyl glycidyl ether carboxy-6'-methylphenyl)-3-(ethyl glycidyl ether)-3-methyl-triaz(1)ene | AT10 |
| 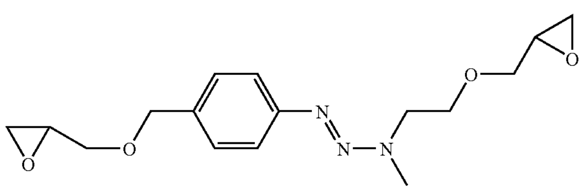 | 1-(4'-methyl glycidyl ether)-3-(ethyl glycidyl ether)-3-methyl-triaz(1)ene | AT11 |
| 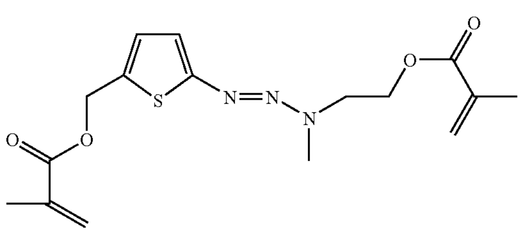 | 2-methacrylatemethyl-5-(3-(2''methacrylate-ethyl)-3'-methyl)triaz(1)ene-thiophene | AT12 |
| 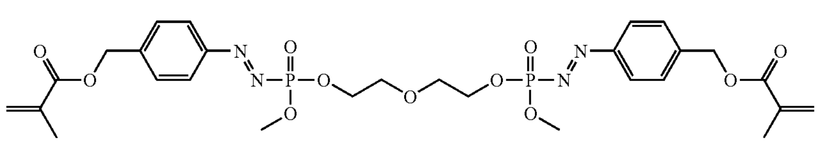 | 1,5-bis[4'-(methacrylatemethyl)phenyl-azomethyl-phosphonate]-diethylene glycol | AAP1 |
| 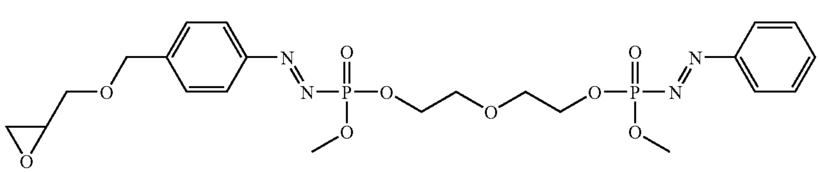 | 1,5-bis[4'-(methyl glycidyl ether)phenylazomethyl-phosphonate]-diethylene glycol | AAP2 |

-continued

| Structure | Name | Ref |
|---|---|---|
| 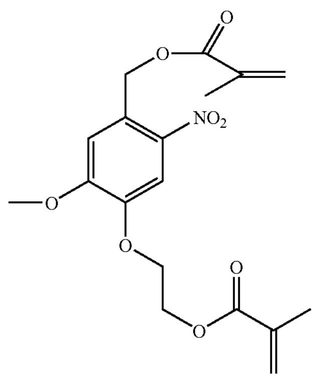 | 2-Methyl-acrylic acid 5-methoxy-4-[2-(2-methyl-acryloyloxy)-ethoxy]-2-nitro-benzyl ester | NT1 |
| 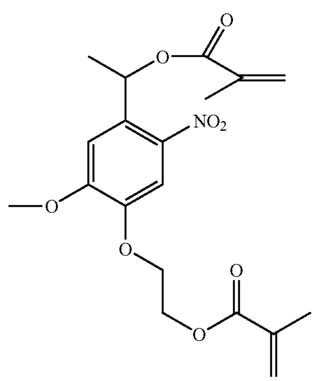 | 2-Methyl-acrylic acid 1-{5-methoxy-4-[2-(2-methyl-acryloyloxy)-ethoxy]-2-nitro-phenyl}-ethyl ester | NT2 |
| 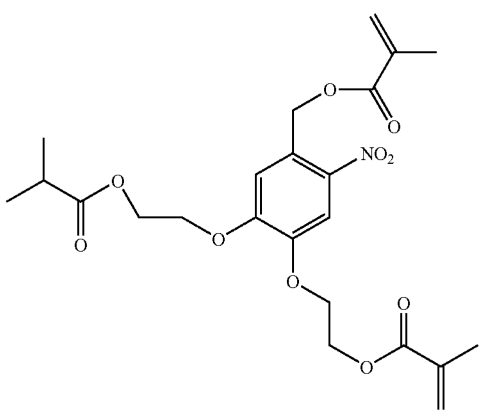 | 2-Methyl-acrylic acid 4,5-bis-[2-(2-methyl-acryloyloxy)-ethoxy]-2-nitro-benzyl ester | NT3 |
| 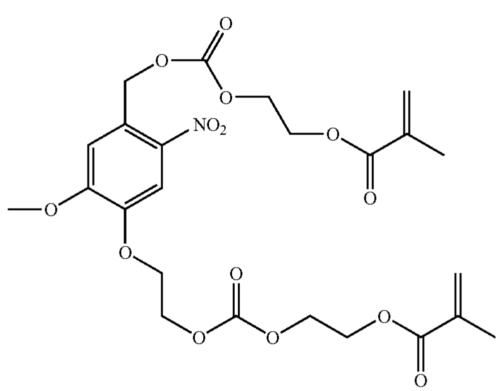 | 2-Methyl-acrylic acid 2-(5-methoxy-4-{2-[2-(2-methyl-acryloyloxy)-ethoxycarbonyloxy]-ethoxy}-2-nitro-benzyloxycarbonyloxy)-ethyl ester | NT4 |

-continued

| Structure | Name | Ref |
|---|---|---|
| 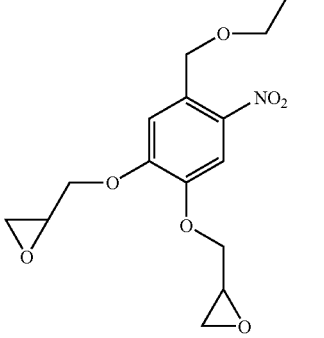 | 2-[2'-nitro-4',5'-di(oxymethyloxirane)]benzyl-oxymethyloxirane | NT5 |
| 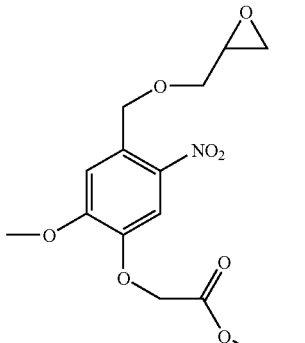 | (2-Methoxy-5-nitro-4-oxiranylmethoxymethyl-phenoxy)-acetic acid oxiranylmethyl ester | NT6 |

In a particularly advantageous variant of the invention, the bifunctional monomer is of oligomer or prepolymer size, optionally has more than two polymerizable units, and has a defined so-called "controlled" complex structure, i.e. the conditions and parameters of synthesis of these particular compounds enable the desired structure to be obtained.

The use of said bifunctional monomers in the adhesive composition of the invention offers advantages in respect of control over the viscosity of the composition and can reduce the well-known phenomenon of polymerization shrinkage and its disadvantages.

Two aspects are presented more particularly below which are found in the examples of bifunctional compounds and adhesive compositions of the invention.

A—According to a first aspect of this advantageous variant, the bifunctional monomer is a linear polymer having a branched comb structure in which the photocleavable units and the polymerizable units are preferably arranged on the comb branches of the principal linear chain of the polymer. Said bifunctional monomer may schematically be described as follows:

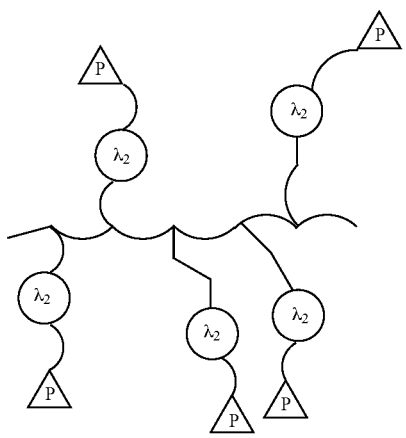

where is a photocleavable unit chosen from among the above-described photocleavable units or any other photocleavable unit photosensitive to a wavelength of λ2 and

is a polymerizable unit chosen from those described above.

In a first preferred alternative, the principal linear polymer chain is a chain whose structure may be chosen from among a large variety of possible structures, such as poly(ether), poly(ester), poly(acrylate), poly(amide), poly(acrylamide), poly(imide), poly(styrene), poly(urethane), poly(carbonate), poly(siloxane), poly(epoxide), poly-(phtalamide), poly(ethersulfonate), poly(alcene), poly-(aryltriazene), poly(arylasophosphonate), poly(o-nitrobenzyl) and any other conventional skeleton in polymerization techniques that is compatible with optional structural modification to allow grafting of the chain or the substituents contained in the chemical skeletons to link at least one photocleavable unit to at least one polymerizable unit, the bond between the photocleavable unit or units and the polymerizable unit or units being achieved in a way that conforms to definitions of bifunctional monomers of the invention, capable under radiation of wavelength □2 to photo-disrupt the principal branches of the linear chain of the polymer which therefore frees itself of the crosslinked polymer network obtained after polymerization of the adhesive composition.

In a second alternative, the branches comprising one or more photocleavable units and one or more polymerizable units may be synthesized in two or three steps, similarly to the general synthesis schema for bifunctional monomers set forth above, for example synthesis of the photocleavable unit directly on the pluri-substituted or poly-branched polymer chain followed by structural modification and/or followed by attachment of the polymerizable units, or grafting of the pre-synthesized photocleavable unit and attachment of the polymerizable units for example, or grafting of the "photocleavable unit-polymerizable unit" entity.

Advantageously, in a preferred embodiment of the two preceding alternatives, the principal linear chain can have substituents or can be modified so as to be provided with substituents able to set up a covalent bond with a chain whose chemical skeleton is made up of at least one photocleavable unit linked to at least one polymerizable unit, the achievement of this covalent bond being made using the synthesis modes described above for grafting vinyl polymerizable units.

A-a) In a particular embodiment, the branches have polymerizable functions of vinyl type at their ends.

One preferred manner to conduct grafting is "in one pot" synthesis in which the attachment of the vinyl unit is immediately followed by grafting of the "photocleavable unit(s)—vinyl unit(s)" branch, the two successive steps being based on the grafting reactions described previously for vinyl units. More precisely, the skeleton of the photocleavable unit terminates in two antagonist functions, for example one of these functions is typically —OR, —OCOR, $NR_2$ whilst the other function is essentially an acid or carboxylic ester.

The method for preparing said monomer consists of initially conducting the synthesis or grafting of a vinyl function through a nucleophilic substitution reaction on an acyl carbon. For an acid function, the reaction is preferably conducted in the presence of dehydrating agents such as 2-pyridinethiol, 1-methyl-2-chloropyridinium iodide, dicyclo-hexylcarbodiimide, N,N'-diisopropylcarbodiimide, N,N'-carbonyldiimidazole, 1,1'carbonylbis(3-methylimidazolium)triflate, di-2-pyridyl carbonate, 1-hydroxybenzotriazole, an acylation agent of Pyridine/Tosyl Chloride type or $SOCl_2/DMF$, preferably 1-methyl-2-chloropyridinium iodide, 2-pyridinethiol, dicyclohexylcarbodiimide, N,N'-diisopropyl-carbodiimide. For an ester function, the reaction is a transesterification that is preferably conducted in the presence of catalysts such as titanates, organic tin oxides and esters such as those cited above, using a basic catalysis method in the presence of non-ionic bases providing soft operating conditions such as amines (for example triethylamine, 1,2,2,6,6-pentamethyl-piperidine, 4-dimethyl-aminopyridine), amidines (e.g. 1,8-diazabicyclo[5.4.0]undec-7-ene), guanidines (e.g. 1,5,7-triazabicyclo[4.4.0]dec-5-ene, 1,1,3,3-tetramethyl-guanidine, 1,3-diphenylguanidine), triamino(imino)-phosphoranes; in preferred manner in the presence of guanidine derivatives, bisguanidines in particular as described in *Tetrahedron Letters* 39 (1998), 2743-2746), soluble polyguanidines or supported on a silica or polystyrene support described in *Reactive & Functional Polymers* 48 (2001), 65-74.

In a second step, the entity consisting of the photocleavable unit/vinyl unit obtained after the first step is grafted to a substituent of the principal linear polymer chain, said substituent ending in a function antagonist to an end function of the photocleavable unit/vinyl unit entity. The operating conditions are similar to those for the first step of the method.

A-b) In a further particular embodiment, the branches have polymerizable functions on their ends of vinyl or oxirane type.

A preferred method of grafting is three-step synthesis: the first step consists of grafting the skeleton of the photocleavable unit onto the substituents of the principal chain, the second is the structural modification of the grafted chemical skeleton (or graft), the third is the attachment of the polymerizable unit through creation or grafting. According to this embodiment, the grafting of the first step is the creation of a covalent bond using the same synthesis modes as set forth previously for the grafting of vinyl units. The structural modification of the second step is a conversion causing an "antagonist" function to appear on the end of the graft (such as previously designated F1 and F2) enabling the creation or grafting during the third step of polymerizable units according to the general synthesis modes described above for vinyl and oxirane units, or according to the more particular modes given under A-a) in the first particular embodiment of this first aspect of this advantageous variant of the invention.

The preferred conversions of the second step are the general reducing methods of carbon-heteroatom unsaturated derivatives (O or N) by carbon or heteroatom attack making it possible to create "antagonist" functions provided that they are compatible with the chemical skeletons (polymer chain, photocleavable unit, etc.). Reagents of choice are $LiAlH_4$, $NaBH_4$, $AlH_3NaBH_4$ for example in isopropanol, sodium triacetoxyborohydride, $Li(Et_3CO)_3AlH$, $ZnBH_4$ in THF, or $NaBH_4$ in aqueous ethanol in the presence of $CeCl_3$. Depending upon the type of polymer chain, aluminium isopropoxide in isopropanol is a method applicable to ketone reduction. The reagents derived from boranes such as $BH_3$-THF, $BH_3$-triethylamine, $BH_3$-$Me_2S$, 9-BBN are generally adapted in most cases to the reduction of carbonyl compounds to obtain alcohol functions in the presence of photocleavable units such as aryltriazene or 2-nitrobenzyl.

The previously cited reagents, and more generally the derivatives of metallic hydrides, properly selected, may therefore be used to create alcohol or amine functions, from imine functions, Schiff bases, nitrile, epoxide, carboxylic acid derivatives with the exclusion of the nitro groups if a 2-nitrobenzyl function is present (therefore LiAlH$_4$ cannot be used in this instance).

Other conversions are possible for the second step:

the generation of "antagonist" functions may also be made, depending upon the type of all the chemical skeletons present, using organometallic compounds added onto functions such as carbonyl, unsaturated α, β carbonyl, imine, acid and derivatives, or oxirane. The preferred reagents are: Grignard reagents optionally in the presence of LiOCl$_4$, Bu$_4$N$^+$Br$^-$, toluene, benzene, CeCl$_3$, TiCl$_4$, (RO)$_3$TiCl, (RO)$_3$ZrCl, (R$_2$N)TiX, in particular when special functions are present; alkyl- or aryllithiums, alkylzincs, tin allyltrialkyls, in the presence of BF$_3$, Et$_2$O, allyltrialkysilanes in the presence of a Lewis acid, allyl boranes; the conditions of the Reformatsky reaction (ketone or aldehyde, □-halo ester) in the presence of zinc.

hydroboration of olefins is a particularly preferred conversion, preferably on the ends of the skeletons of the photosensitive grafts, which enables soft generation of alcohol functions after hydrolysis in the presence of NaOH and hydroperoxide. Suitable reagents are BH$_3$-THF, BH$_3$-Me2S or NaBH$_4$ combined with BF$_3$, Et$_2$O, 9-BBN, mono/dialkylboranes.

one applicable conversion depending upon the type of chemical skeletons, is hydrolysis of imines, Schiff bases or isocyanates, optionally with acid or basic catalysis, to generate an amine function at the end of the photocleavable grafts.

one particularly preferred conversion to obtain a primary or secondary amine function consists of converting a halide derivative of 2-nitrobenzyl into aminomethyl-2-nitrobenzene for example by treatment with potassium phtalimide followed by hydrazinolysis, or into N-substituted aminomethyl-2-nitrobenzene by substitution in the presence of the corresponding N-substituted amine.

Examples of such bifunctional prepolymer compounds, of polysubstituted linear polymer type, are:

Poly((14-(2'-aminoacylethyl)-6-(hydroxymethyl)-1,4,8,11-tetraoxa-12-oxo-13-aza-tetradecane)-co-(7-(2'4'-aminoacylethyl)-1,4-dioxa-5-oxo-6-aza-heptane)], Poly[(14-(4'-aminoacylethexyl)-6-(hydroxymethyl)-1,4,8,11-tetraoxa-12-oxo-13-aza-tetradecane)-co-(7-(4'-aminoacylhexyl)-1,4-dioxa-5-oxo-6-aza-heptane)], Poly[(14-(4'-'(4"-aminocylphenyl)methylphenyl)-6-(hydroxymethyl)-1,4,8,11-tetraoxa-12-oxo-13-aza-tetradecane)-co-(7-(4'-(4"-aminoacylphenyl)methylphenyl)-1,4-dioxa-5-oxo-6-aza-heptane)], Poly((14-'4'-(4"-aminoacylcyclohexyl)methylcyclohexyl)-6-(hydroxymethyl)-1,4,8,11-tetraoxa-12-oxo-13-aza-tetradecane)-co-(7-(4'-(4"-aminoacylcyclohexyl)methylcyclohexyl)-1,4-dioxa-5-oxo-6aza-heptane)]

in which all these polymers are esterified on the hydroxy group at position 6 of the copolymer chain by groups of type:

-oxycarbonyl-3-[3'-(2"-(methacrylate)ethyl)]-3'-methyltriazene) phenyl oxycarbonyl-ethyloxy-(1-methoxy-3-(methacrylatemethyl)-4-nitro)phenyl.

Preferred compounds of polysubstituted linear polymer type are:

Poly[(14-(4'-methylaminoacylcyclohexyl)-6-(hydroxymethyl)-1,4,8,11-tetraoxa-12-oxo-13-aza-tetradecane)-co-(7-(4'-methylaminoacylcyclohexyl)-1,4-dioxa-5-oxo-6-aza-heptane)], Poly[(14-(4'-aminoacylbutyl)-6-(hydroxymethyl)-1,4,8,11-tetraoxa-12-oxo-13-aza-tetradecane)-co-(7-(4'-aminoacylbutyl)-1,4-dioxa-5-oxo-6-aza-heptane)], both being esterified on the hydroxy group at position 6 of the copolymer chain by groups of type: -oxycarbonyl-3-[3'-(2"-(methyacrylate)ethyl))-3"methyltriazene]phenyl or of type -oxycarbonyl-ethyloxy-(1-methoxy-3-(methacrylatemethyl)-4-nitro)phenyl.

These four preferred associations will respectively be referred to as: PU1AT1, PU1NT1, PU2AT1 and PU2NT1.

B—According to a second aspect of the variant in which the bifunctional monomer is of oligomer of prepolymer size, the bifunctional monomer is a hyperbranched polymer whose structure derives from step polymerization of a type AB$_n$ monomer, and is preferably derived from step polymerization of a monomer of type AB$_3$ or AB$_2$, where A and B are respectively two different chemical functions capable of reacting together under condensation or addition reaction to give a polymer chain having branch point where every B function disappears.

In a first alternative, the hyperbranched polymer so designated has a "core" consisting in particular of monomer units having one or more photocleavable units in their skeletons and a "shell" around the core whose branches are formed of essentially inert monomer units from a photochemical viewpoint, the ends of the branches ending in at least one polymerizable unit, preferably only one.

In a second alternative, the hyperbranched polymer so designated has a "core" formed in particular of essentially inert monomer units from a photochemical viewpoint and a peripheral "shell" around the core whose branches consist of monomer units having one or more photocleavable units in their skeleton and whose branch ends terminate in at least one polymerizable unit, preferably only one.

The preferred general structure of a type AB$_2$ monomer able to polymerize following a step polymerization mode to give a hyperbranched polymer such as designated is as follows:

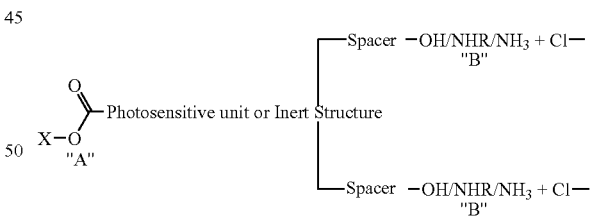

The functions A and B meet the criterion of antagonist functions and, in this respect, may be chosen from among all those previously described. In preferred manner, A is a function derived from carboxylic acid, preferably a carboxylic acid, carboxylic ester, carboxylate, trimethylsilylated carboxylic acid, acyl chloride function, and B is an alcohol function, optionally trimethylsilylated, esterified, a NH$_2$ amino group or a primary amine or primary ammonium salt. The preferred combinations are those in which A is a carboxylic acid function or ester and in which B is an alcohol or amino function.

Typical examples of AB$_2$ monomers are for example 2,2-bis(hydroxymethyl)propionic acid (inert monomer) and 1-(3'-carboxyphenyl)-3-,3-di(2"-hydroxyethyl)triazene (photosensi-tive monomer).

The privileged preparation modes for these hyperbranched structures are based on the use of dehydrating agents, in particular if A is a carboxylic acid function, such as in particular 1-methyl-2-chloropyridinium chloride, dicyclohexylcarbodiimide, N,N'-diisopropylcarbodiimide, N,N'-carbonyldiimidazole, 1,1-carbonylbis(3-methyl-imidazolium) triflate, di-2-pyridyl carbonate, 1-hydroxybenzotriazole, an acylation agent of Pyridine/Tosyl Chloride type or SOCl$_2$/DMF, preferably 1-methyl-2-chloropyridinium chloride, 2-pyridinethiol, dicyclo-hexylcarbodiimide, N,N'-diisopropyl-carbodiimide. If A is an ester function, the reaction is a transesterification preferably conducted in the presence of catalysts such as titanates, organic tin oxides and esters (in particular those already cited), using a basic catalysis mode in the presence of non-ionic bases providing soft operating conditions such as amines (for example triethylamine, 1,2,2,6,6-pentamethylpiperidine, 4-dimethylaminopyridine), amidines (for example 1,8-diazabicyclo[5.4.0]undec-7-ene), guanidines (for example 1,5,7-triazabicyclo[4.4.0]dec-5-ene, 1,1,3,3-tetra-methylguanidine, 1,3-diphenylguanidine), triamino(imino) phosphoranes; in preferred manner, in the presence of the guanidine derivatives, bisguanidines in particular such as described in *Tetrahedron Letters* 39 (1998), 2743-2746, and polyguanidines either soluble or supported on a silica or polystyrene support as described in *Reactive & Functional Polymers* 48 (2001), 65-74.

Particular mention is made of the case in which the photocleavable units used are exclusively benzyl derivatives and more specifically 2-nitrobenzyl derivatives. In this case, the step polymerization reactions, in particular the polyesterification reactions, are advantageously conducted under conditions of acid catalysis (in the presence of sulfonic para-toluene acid or sulfuric acid for example), in addition to the preceding conditions which also apply.

As indicated at the beginning of this part concerning the privileged variant of bifunctional monomers, the structures are preferably controlled which means that for this second aspect a distinction is made between the preparation of the core and of the peripheral shell. In particular when the "core" is a photocleavable core, the preparation methods are based on step polymerization methods by slow addition of the AB$_2$ monomers to a system of "core molecules" present in strong concentration in the reaction medium at all times relative to the concentration of reactive AB$_2$ monomers. These preparation methods, or derivative methods, are described in particular in *Macromolecules*, 1998, 31, 3790-3801; *Macromolecules*, 2001, 34, 7692-7698; *Macromolecules*, 2002, 33, 3212-3218; *Macromolecules*, 2000, 33, 3099-3104; *Polymers for Advanced Technologies*, 2001, 12, 346-354. Advantageously the core is typically a photocleavable molecule of B$_n$ type and includes functions such as aryltriazenes or 2-nitrobenzyls, or is a hyperbranched polymer chain such as the one obtained by polycondensation of 1-(4'-carboxyphenyl)-3,3-di(2"-hydroxy-ethyl)triazene, of 1-(3'-carboxyphenyl)-3,3-di(2"-hydroxyethyl)triazene, or of 1-(3'-carboxy-6'-methylphenyl)-3,3-di-(2"-hydroxyethyl)triazene in the presence of N,N-diisopropylcarbodiimide and APTS.

The preferred preparation methods use the attachment of polymerizable units to branch ends to give the bifunctional monomer of the invention, according to a final step in which the polymerizable unit is created or it is grafted by attachment of a final photosensitive or inert layer of type AB$_n$ monomers, which already carry polymerizable units. This final step is performed using all the possibilities indicated previously for the synthesis process according to the compatibilities offered by the chemical structure of the synthesized polymers, in which preference is given to:

for vinyl units: possibilities 1°)1) to 1°)4) for creation, all of 2°) for grafting;

for oxirane units: the first three manners for creation and the first and third manner for grafting.

For the first alternative of bifunctional structures of hyperbranched polymer type, namely with photosensitive core and inert shell, the following particular examples are chosen:

Poly(1-(3'-carboxyphenyl)-3-,3-di(2"-hydroxyethyl)triazene),

Poly(1-(3'-carboxy-6'-methylphenyl)-3-,3-di(2"-hydroxyethyl)triazene),

Poly(1-(4'-carboxyphenyl)-3-,3-di(2"-hydroxyethyl)triazene),

Poly(1-(3',5'dicarboxypheny)-3-(2"-hydroxyethyl)-3-methyl-triazene),

ω-functionalized by methacrylate ends with methacrylic acid and its derivatives, such as 2-hydroxyethylmethacrylate, glycidyl methacrylate or 2-isocyanatoethyl methacrylate for example, or by oxirane ends of glycidyl type by reaction with an epihalohydrine, for example.

Poly(1-(3'carboxyphenyl)-3-,3-di(2"-hydroxyethyl)triazene), ω-functionalized by the derivatives of methacrylic acid and which will be denoted PH1AT1.

Poly(1-(3'-carboxy-6'-methylphenyl)-3-,3-di(2"-hydroxyethyl)triazene), ω-functionalized by the derivatives of methacrylic acid which shall be denoted PH1AT2.

The above examples of hyperbranched structures are among the most simple which may be considered, the inert shell consisting of polymerizable units.

Other examples of hyperbranched structures with photosensitive core and inert shell are in particular:

Poly(1-(3'carboxyphenyl)-3-,3-di(2"-hydroxyethyl)triazene-co-2,2-bis(hydroxymethyl)propionic acid), Poly(1-(3'-carboxy-6'-methylphenyl)-3-,3-di(2"-hydroxyethyl)triazene-co-2,2-bis(hydroxymethyl)propionic acid), Poly(1-(4'-carboxyphenyl)-3-,3-di(2"-hydroxyethyl)triazene-co-2,2-bis(hydroxymethyl)propionic acid), ω-functionalized by methacrylate ends with methacrylic acid and its derivatives, such as 2-hydroxyethylmethacrylate, glycidyl methacrylate or 2-isocyanatoethyl methacrylate for example, or by oxirane ends of glycidyl type by reaction with an epihalohydrine, for example Poly(1-(3'-carboxyphenyl)-3-,3-di(2"-hydroxyethyl)triazene-co-2,2-bis(hydroxymethyl) propionic acid, ω-functionalized by the derivatives of methacrylic acid and denoted PH2AT1;

Poly(2,5-Bis-chloromethyl-1,3-dinitro-benzene-co-2,2-bis(hydroxymethyl)propionic acid) ω-functionalized by the derivatives of methacrylic acid and denoted PH2NT3.

Poly((2-Nitro-4,5-bis-oxiranylmethoxy-phenyl)-methanol-co-2,2-bis(hydroxymethyl)propionic acid) ω-functionalized by the derivatives of methacrylic acid, and denoted PH2NT1.

For the second alternative of bifunctional structures of hyperbranched polymer type, namely with inert core and photosensitive shell, particular choice is made of:

Poly(2,2-bis(hydroxymethyl)propionic acid -co-1-(3'-carboxyphenyl)-3-, 3-di(2"-hydroxyethyl)triazene), Poly(2,2-bis(hydroxymethyl)propionic acid -co-1-(3'-carboxy-6'-methyhenyl)-3-,3-di(2"-hydroxyethyl)triazene), ω-functionalized by methacrylate ends with methacrylic acid and its derivatives, such as 2-hydroxyethylmethacrylate, glycidyl methacrylate or 2-isocyanatoethyl methacrylate for example, or by oxirane ends of glycidyl type by reaction with an epihalohydrine, for example.

Poly(2,2-bis(hydroxymethyl)propionic acid), ω-functionalized by an oxycarbonyl-3-[3'-(2"-(methacrylate)ethyl)) triazene]phenyl group or an -oxycarbonyl-ethyloxy-(1-methoxy-3-(methacrylatemethyl)-4-nitro)phenyl group.

DETAILED EXAMPLES OF BIFUNCTIONAL COMPOUND SYNTHESIS

Below is a detailed description of four examples implementing the method of fabricating bifunctional monomers of the invention, such as described previously in more general manner. On the basis of these examples of synthesis and proposed techniques, those skilled in the art will be able to obtain any photocleavable, polymerizable bifunctional monomer meeting the minimum required structural criteria for producing the photosensitive adhesive composition of the invention.

1. Synthesis of the NT5 Bifunctional Monomer

Step 1:

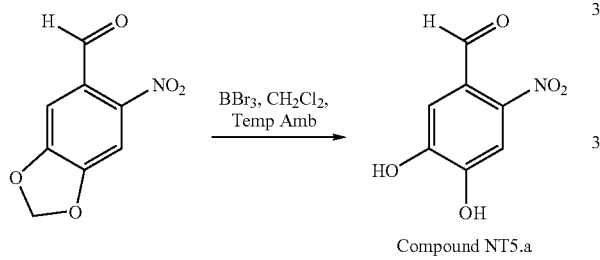

Compound NT5.a

To a single neck, oven-dried, 100 mL round-bottomed flask, are added 2 g 6-nitropiperonal, then under inert atmosphere at 0° C., 30 mL BBr$_3$ (1.0M in CH$_2$Cl$_2$). The medium is then stirred at ambient temperature. 10 mL BBr$_3$ (1.0M) are further added after 12 h and 5 mL after 24 h. After 48 h, the reaction medium is decanted into a 1 litre bottle placed over an ice bath and 100 mL water are added very slowly. The mixture is concentrated. The residue is then collected with minimum volume THF and again cold precipitated by adding 35% hydrochloric acid. The precipitate is filtered through a glass sinter filter and the operation is repeated at least 3 times. The precipitated product is finally purified by flash chromatography on silica gel with an eluant (70 mL/30 mL/5 mL petroleum ether/ethyl acetate/ethanol). 1.28 g of compound NT5.a are obtained.

Step 2:

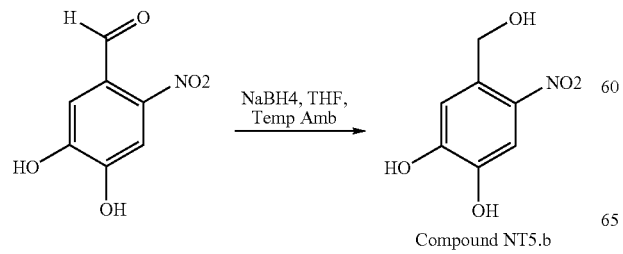

Compound NT5.b

To a three neck, oven-dried round-bottomed flask, 1 g of NT5.a compound are added and 516 mg NaBH$_4$. The flask is surmounted by a refrigerant and the assembly closed and placed in an inert atmosphere. Using a syringe, 100 mL anhydrous THF are added. The reaction medium is stirred for 30 h at ambient temperature. At the end of the reaction, 20 mL ethanol are added and left under stirring for 30 minutes. The reaction medium is concentrated, collected several times in THF and filtered. The grouped filtrates are concentrated and the residue is purified by flash chromatography on silica gel with eluant (70 mL/30 mL/10 mL petroleum ether/ethyl acetate/ethanol). 960 mg of compound NT5.b are obtained.

Step 3:

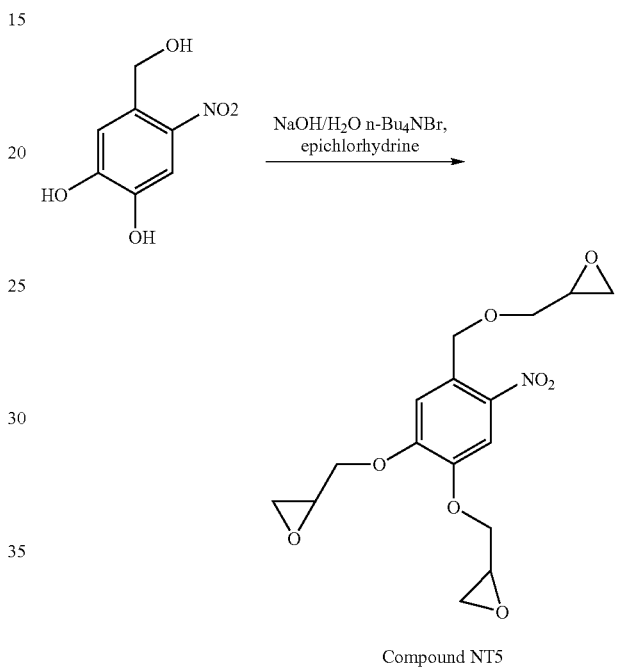

Compound NT5

To a 200 mL three neck round-bottomed flask, 16 mL aqueous solution containing 50% potassium hydroxide and 11 ml epichlorhydrine are added together with 380 mg tetrabutyl-ammonium bromide. The mixture is stirred at 0° C. and followed by cold, progressive addition of 1.5 g NT5.b so that the temperature does not exceed 25° C. After a reaction time of 15 h, the medium is poured into 30 mL of a water/ice mixture. The aqueous phase is extracted with ethyl ether (3*60 mL). The organic phases are grouped together and washed with an aqueous solution of NaCl (5*60 mL), dried on sodium sulfate and concentrated. The residue is distilled under reduced pressure and purified by flash chromatography on silica gel with an eluant (90 mL/10 mL petroleum ether/ ethyl acetate) to yield 1.26 g of compound NT5.

II. Synthesis of the AT1 Bifunctional Monomer

Step 1:
  a) The diazonium tetrafluoroborate salt of 4-ethyl-aminobenzoate was prepared (hereafter denoted AT1.a):

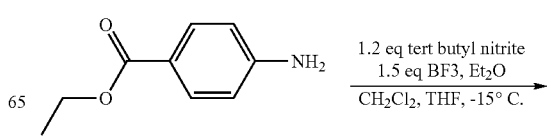

-continued

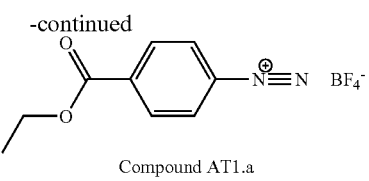

Compound AT1.a

To a three neck, oven-dried round-bottomed flask, 15 g ethyl 4-aminobenzoate are added in 300 mL dry $CH_2Cl_2$ and 50 mL dry THF. The medium is placed in an inert atmosphere and the flask is immersed in a bath cooled to –15° C. 19.35 g $BF_3,Et_2O$ are then slowly added in 40 mL dry $CH_2Cl_2$. When thermal equilibrium is reached 12.5 g tert-butyl nitrite is added over 1 h 30 in 80 mL dry $CH_2Cl_2$ and the medium is maintained under vigorous stirring. When addition is completed, the medium temperature rises to 0° C. Approximately 150 mL pentane are then added to the reaction medium. The formed precipitate is filtered, then washed with 300 mL ethyl ether, filtered again and finally dried at 25° C. in a drying oven in the presence of $P_2O_5$. 23.1 g of compound AT1.a are obtained.

b) Diazoic coupling was performed and a compound hereafter designated AT1.b is obtained:

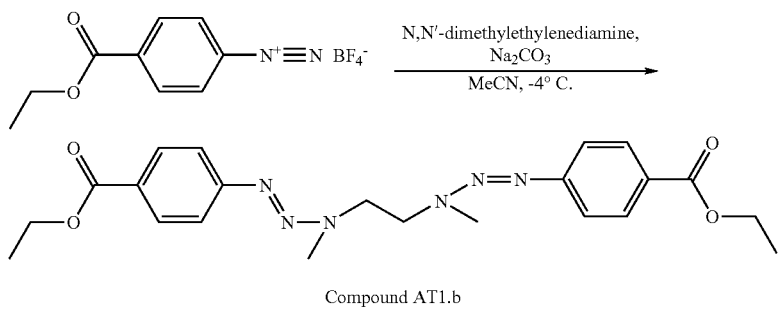

Compound AT1.b

In 250 mL dry MeCN, 15.4 g AT1.a is dissolved and 12.82 g sodium carbonate is added. The medium is cooled in an inert atmosphere over a bath at –4° C. 4.4 g N,N'-dimethylethylene-diamine are added to an addition funnel in 160 mL dry MeCN in the presence of sodium carbonate. The addition to the reaction medium is conducted over 6 h under vigorous stirring. When addition is completed, stirring is maintained for 1 h 30. The reaction medium is then filtered and the salt is washed in ethyl acetate. The product is isolated by successive dissolutions of the crude residue in a minimum volume of ethyl ether, cold crystallization and filtration of the precipitate. The product is dried in a drying oven in the presence of $P_2O_5$ and 12.03 g of the compound AT1.b are obtained.

Step 2:

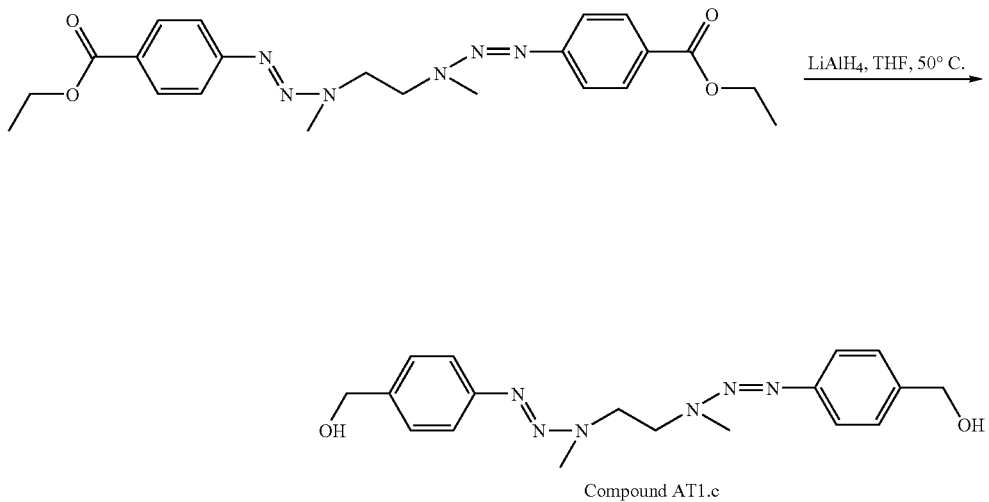

Compound AT1.c

One half-spoon LiAlH$_4$ is placed in a three neck round-bottomed flask, previously oven-dried and fitted with a refrigerant and an addition funnel. The assembly is placed in an inert atmosphere and immersed in an oil bath at 55° C. 4 g AT1.b compound dried on P$_2$O$_5$ are previously placed in the addition funnel. 40 mL dry THF are then added to the flask and 100 mL to the addition funnel. The AT1.b compound is then added drop by drop to the flask under vigorous stirring, and gradually, 120 mL dry THF and 1.8 g LiAlH$_4$ divided into several fractions are directly added to the reaction medium. The medium is stirred at 50° C. for 3 h. At the end of the reaction, a mixture of 50 mL THF and 50 mL ethyl acetate is added slowly, the crude is passed through the glass sinter and the collected solid is washed in methanol until it becomes white. The filtrates are concentrated, washed in a mixture of methanol and THF, and the recrystallized solid is filtered through a sinter. These operations are repeated until practically all the aluminates have been drawn from the AT1.c compound of which 3.23 g is obtained.

Step 3:

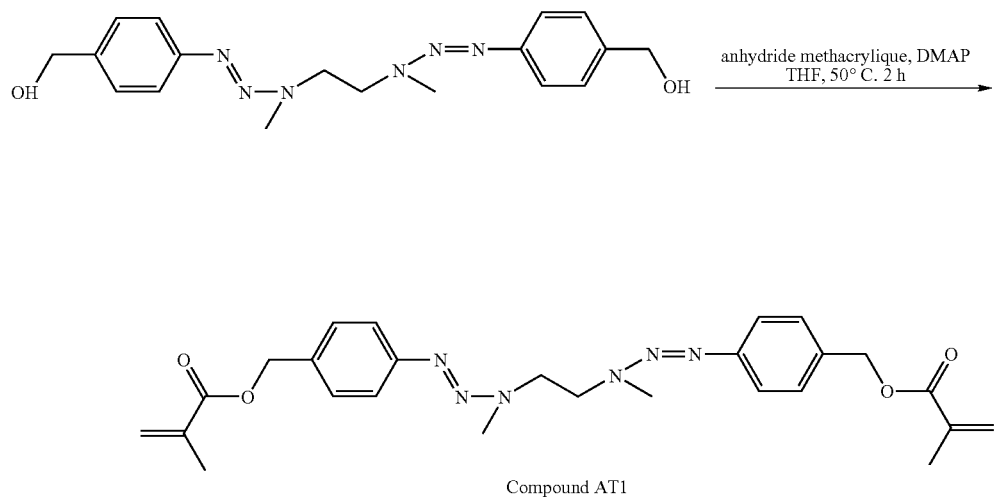

Compound AT1

To an oven-dried three neck round-bottomed flask surmounted by a refrigerant, are added 1.219 g AT1.c compound dried on P$_2$O$_5$ and 2.5 g 4-dimethylaminopyridine (DMAP). The medium is placed in an inert atmosphere and brought to 50° C. Using a dropping funnel, 150 mL dry THF are added to the reaction medium under stirring. After 5 minutes, a syringe is used firstly to add 1.55 mL methacrylic anhydride with +0.3 weight % hydroquinone, then 50 mL dry THF in the dropping funnel. The additions are made slowly to the mixture for one hour and the temperature is then maintained at 50° C. for a further hour, then stirring is continued for 12 h at 20° C.

The reaction medium is then extracted with THF and is cold concentrated. The residue is then extracted by a succession of biphase separations. The crude is first dissolved in 125 mL CH$_2$Cl$_2$. This first phase is extracted with 150 mL iced water, which is in turn extracted with 50 mL CH$_2$Cl$_2$.

The operation is repeated three times. After grouping the organic phases together and drying on sodium sulfate, they are evaporated and the residue is purified by flash chromatography on silica column with an eluant (85 mL/4 mL/13 mL petroelum ether/ethyl ether/ethyl acetate). 1.53 g of compound AT1 are obtained.

III. Synthesis of the PU1AT1 Bifunctional Monomer

Step 1:

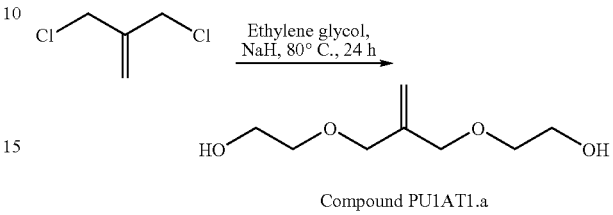

Compound PU1AT1.a

To an oven-dried, three-neck round-bottomed flask fitted with a magnetic stirrer and surmounted by a refrigerant, 450 mL distilled anhydrous glycol ethylene are added under an inert atmosphere. 14 mL 3-chloro-2-chloromethyl-1-propene are added using a syringe. The flask is immersed in an oil bath at 60° C., under vigorous stirring. 12 g 95% NAH are prepared in several portions and the entire quantity of NaH is carefully added in small successive portions to the reaction medium. When addition is completed, the bath temperature is set at 80° C. and it is left under stirring for 24 h.

At the end of the reaction, the mixture is distilled under reduced pressure of 4 mm Hg at a temperature of 80° C. to 140° C. so as to remove a maximum amount of ethylene glycol. The residue is purified by flash chromatography on silica gel with eluant (85 mL/15 mL/2-10 mL petroleum ether/ethyl acetate/ethanol). The product is again concentrated by distillation under reduced pressure and 16.8 g of compound PU1AT1 is obtained with 57.8 weight percentage in a mixture with residual ethylene glycol.

Step 2:

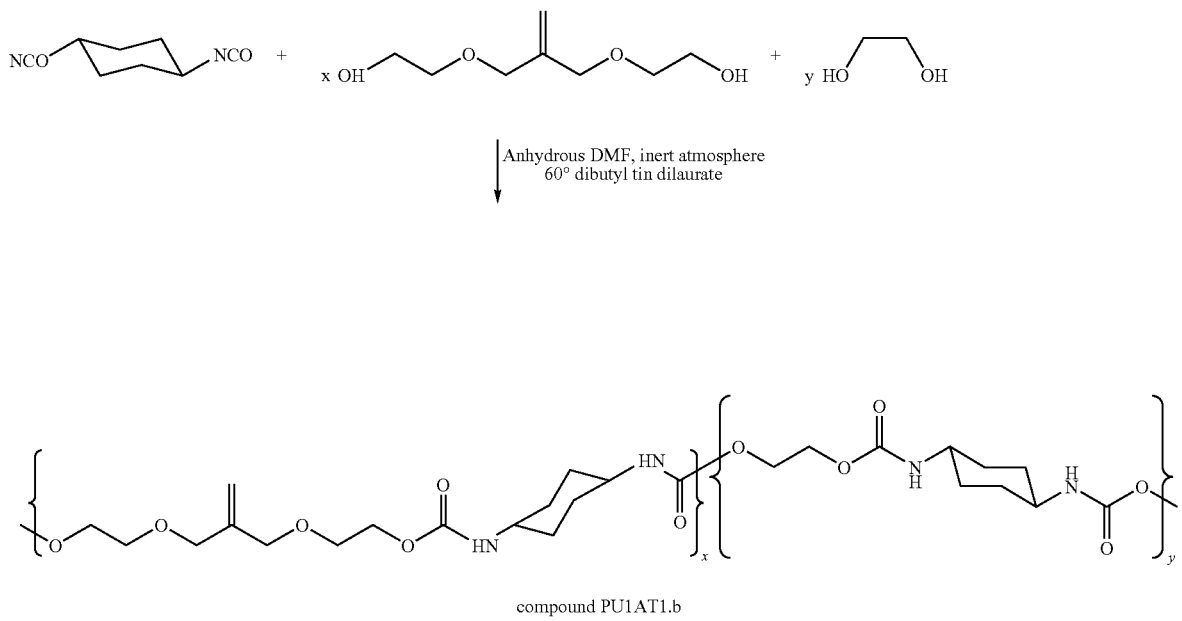

compound PU1AT1.b

In an oven-dried, single neck round-bottomed flask, a magnetic stirrer is placed with 3.555 g of a previously obtained and freshly distilled PU1AT1.a/ethylene glycol mixture. After desolvation under reduced pressure of 4 mmHg for 15 h, the medium is placed in an inert atmosphere. Using a syringe, 5.397 g 1,3-bis(isocyanatomethyl)-cyclohexane are added thereto. 2 mL anhydrous DMF and 8 drops of dibutyl tin dilaurate are then added. The flask is immersed in an oil bath at 65° C. and left under stirring for 72 h. At the end of the reaction, all the DMF is vacuum distilled at 40° C. and a weight of approximately 8.9 g of compound PU1AT1.b is recovered.

Step 3:

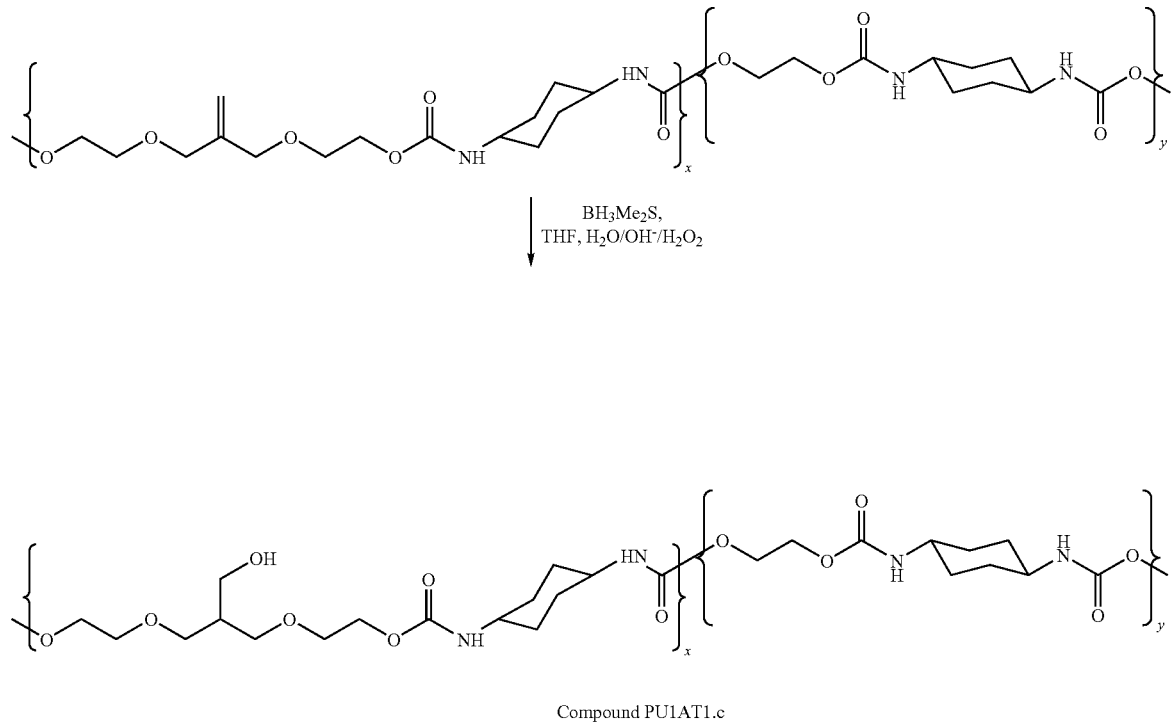

Compound PU1AT1.c

To a twin neck oven-dried round-bottomed flask, 0.516 g PU1AT1.b polymer are placed with a magnetic stirrer. The flask is placed in a vacuum overnight. The flask is then placed under a stream of nitrogen and 20 mL anhydrous THF are added. The flask is immersed in an ice bath and 0.2 mL BH$_3$.Me$_2$3 are added. Stirring is maintained for 2 h 30, then successive cold additions are made of 0.1 mL distilled water, 0.1 mL 3M NaOH, 0.5 mL THF, 0.17 mL absolute ethanol and 0.18 mL 30% H$_2$O$_2$. The mixture is brought to 40° C. for 3 hours under vigorous stirring. At the end of the reaction, it is concentrated then 70 mL CH$_2$Cl$_2$ are added to the residue and the precipitate is filtered. The collected filtrate is concentrated, washed and extracted with CH$_2$Cl$_2$ several times. Further concentration is performed and 5 mL methanol with 40 mL ethyl ether are added, followed by filtration and concentration. 415 mg of the compound PU1AT1.c are obtained.

Step 4:

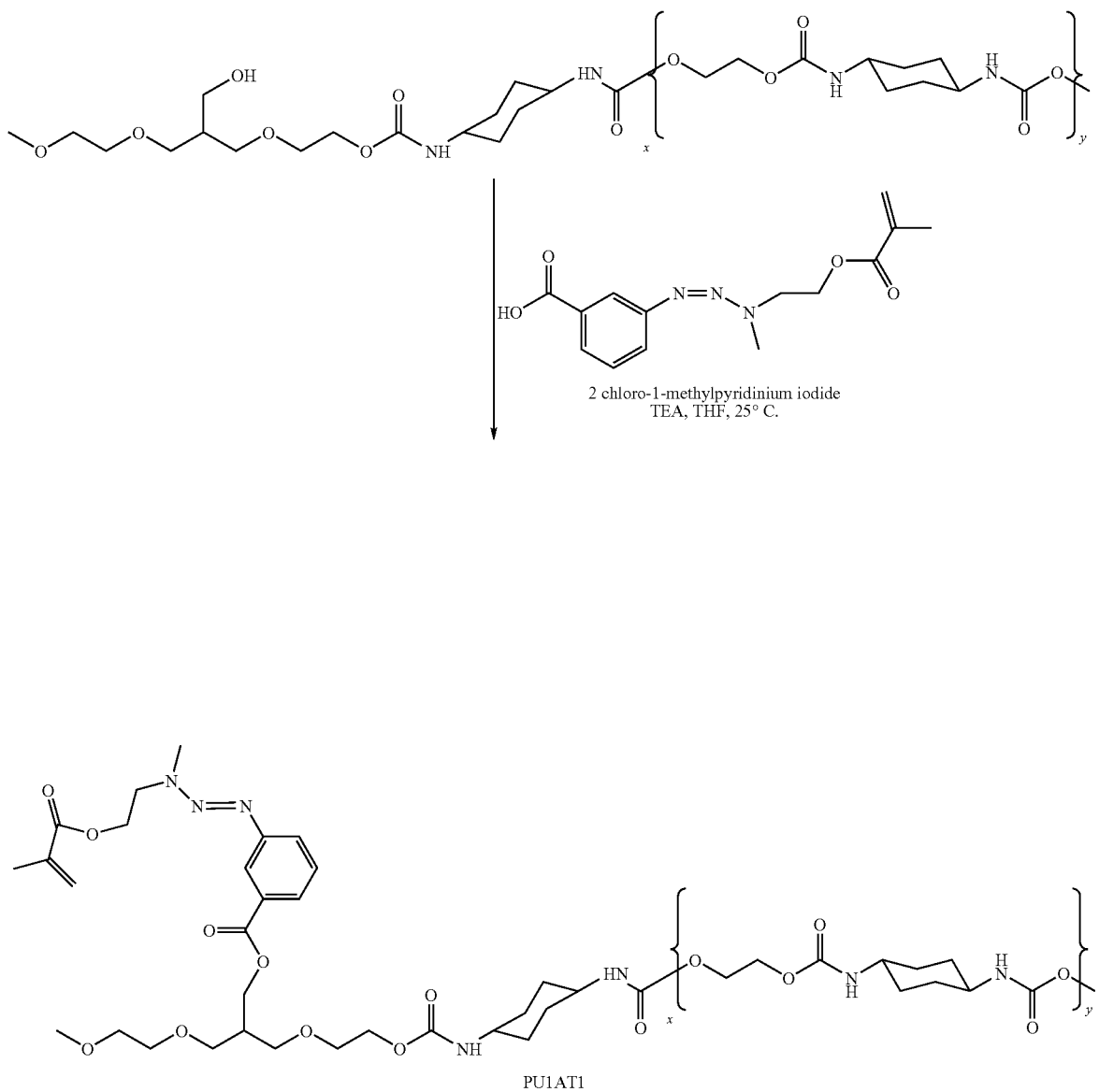

To a dried, three neck round-bottomed flask, 0.980 g of 2-chloro-1-methylpyridinium iodide are added. The flask is fitted with a dropping funnel containing 500 mg dried PU1AT1.C, and with a second dried single neck round-bottomed flask containing 350 mg 1-(3'carboxyphenyl)-3-(2"-hydroxyethyl)-3-methyltriaz(1)ene and connected via tubing to the three-neck flask. The assembly is placed under nitrogen, 60 ml anhydrous THF are added to the reaction medium with 134 mg methacrylic acid and 165 mg distilled triethylamine. Stirring is carried out for 15 minutes then the content of the second flask is added by pouring. Stirring is conducted for 3 hours and then 5 g triethylamine and 20 mL anhydrous THF are again added to the addition funnel. The dissolved PU1AT1.c polymer is then added to the reaction medium and it is left under stirring for 24 h at ambient temperature. At the end of the reaction, the reaction medium is concentrated and filtered. The precipitate is washed in ethyl ether and the filtrate is concentrated. The obtained crude is dissolved in 40 mL dichloromethane and the organic phase is washed with 10 times 50 mL water at pH 5-6. The organic phases are dried on sodium sulfate and concentrated. The residue is washed several times in pentane and 415 mg PU1AT1 is obtained.

IV. Synthesis of the PH2AT1 Bifunctional Monomer

Step 1: Synthesis of the Precursor 1-(3'-carboxyphenyl)-3,3-di(2"-hydroxyethyl)triazene PH2AT1.a.

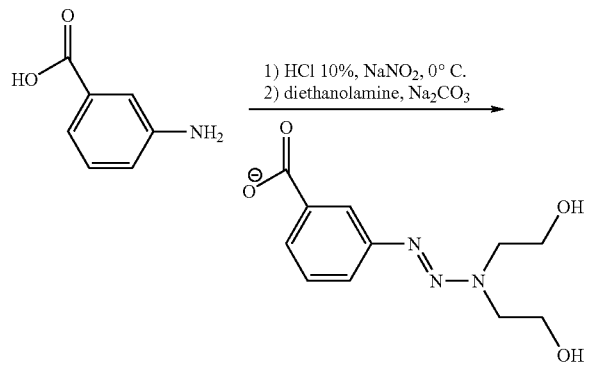

6.857 g 3-aminobenzoic acid are dissolved in a mixture of 16 mL concentrated hydrochloric acid (35%) and 35 mL water cooled by an ice bath in a twin neck round-bottomed flask. The flask is fitted with an addition funnel in which an aqueous solution of sodium nitrite has been placed (3.45 g in 40 mL) to which is added drop by drop the solution of aminobenzoic acid while controlling the temperature of the solution which must remain below +2° C. After addition, stirring is maintained for 30 minutes. The solution obtained is collected and stored at 0° C. In another twin neck round-bottomed flask, another aqueous solution of diethanolamine (10.5 g) is prepared saturated with sodium carbonate. This solution is cooled by an ice bath. Under vigorous stirring, the diazonium salt solution, to which crushed ice is regularly added, is added drop by drop for 45 minutes and stirring is maintained for a further 1 h 30. After coupling, concentration is conducted in a rotary evaporator to recover the carboxylate.

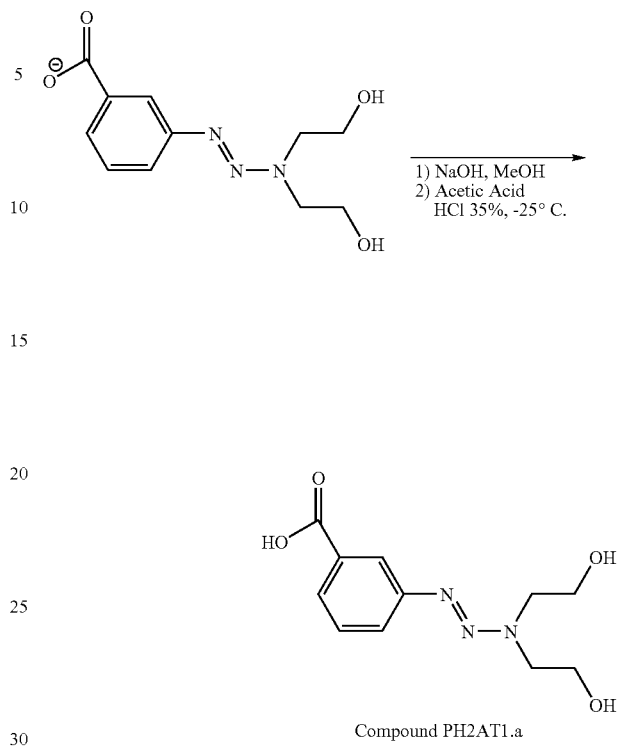

Compound PH2AT1.a

The excess sodium carbonate is removed by distillation of the solid in a minimum volume of acetonitrile and filtration. The filtered solution is concentrated. The sodium carboxylate salt is washed through the addition of 75 mL methanol and 3 mL 35% NaOH aqueous solution. The solution obtained is stirred for one hour at ambient temperature and then concentrated. Finally 45 mL water are added then, under thermal equilibrium with an ethanol bath at −30° C. and stirring, 6.8 mL of a solution containing 3 mL acetic acid and 17 mL water is added. Under constant stirring a sufficient number of drops of 35% concentrated hydrochloric acid are added gradually until a true precipitate is obtained in a solution whose pH must be reduced to 4-5. Under these conditions, 150 mL of very cold water are added and filtration is immediately performed through a glass sinter. After washing in cold water until filtrates are neutral and removing a maximum amount of water, the precipitate is placed in a vacuum oven at 30° C. for a whole day and 8.92 g of PH2AT1.a product are obtained.

Step 2: Polycondensation of 1-(3'carboxyphenyl)-3,3-di(2"-hydroxyethyl)triazene to Obtain PH2AT1.b To an oven-dried, three-neck round-bottomed flask, passed in a Bunsen burner flame alternately under a vacuum and a stream of nitrogen, are added 0.5 g dry PH2AT1.a and 0.124 g dry DPTS (4-(N,N-dimethyl-aminopyridinium)tosylate).

Using a syringe, 3 mL anydrous DMF are then added. Under stirring, 0.45 mL N,N-diisopropylcarbodiimide are added with a syringe over a total time of 4 and a half days.

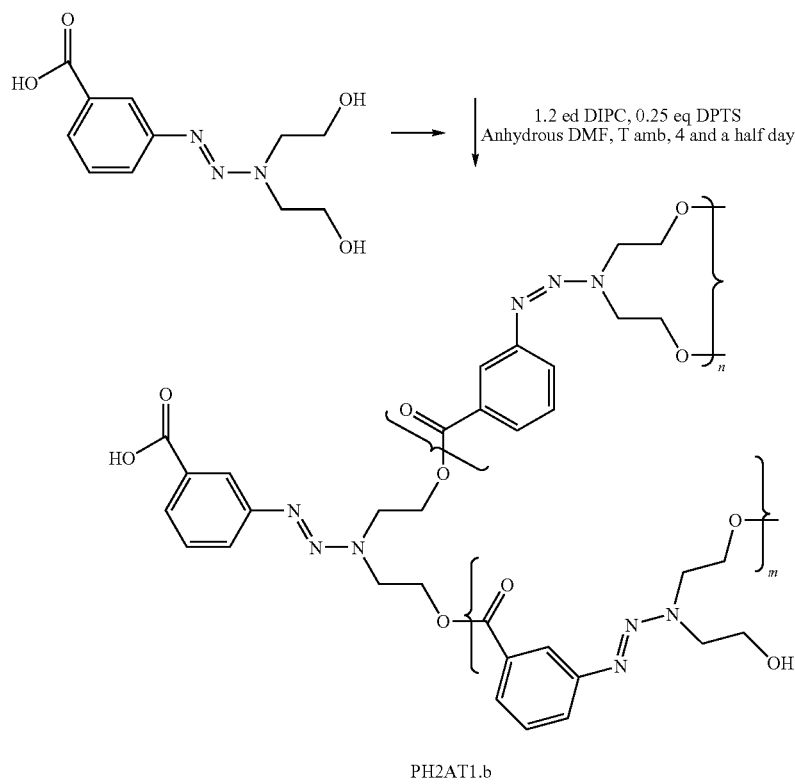

PH2AT1.b

At the end of the reaction, the urea precipitate is filtered through a glass sinter, then repeated precipitation of the polymer is caused by pouring the solution obtained in minimum volumes of a very cold (10% methanol/90% water) mixture and at least an equivalent volume of crushed ice. The filtrate obtained after filtering through a glass sinter is systematically extracted following an identical protocol after concentration in a rotary evaporator. On completion, 0.164 g of a dark brown solid of the PH2AT1.B polymer were recovered after a 2-day residence time in a vacuum oven at a temperature of 35° C.

Step 3: Synthesis of an inert shell of poly(2,2'bis-hydroxymethylpropionic acid): Obtaining the PH2AT1.c polymer.

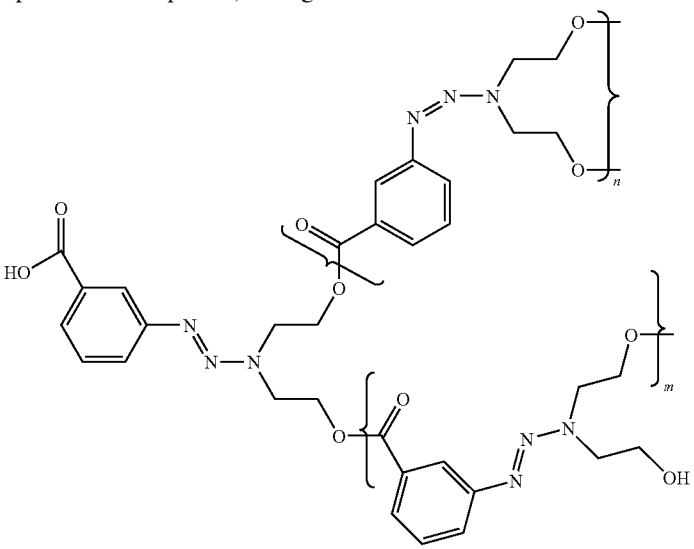

PH2AT1.b 2-chloro-1-methylpyridinium iodide
2,2-bis(hydroxymethyl) propionic acid
Triethylamine, amb temp 48

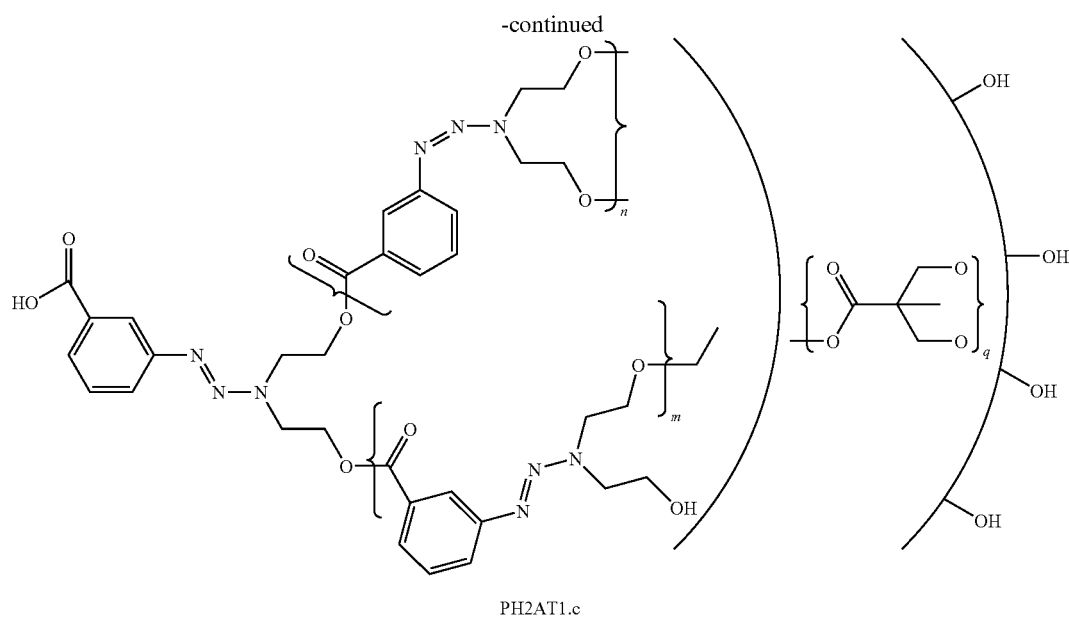

PH2AT1.c

To a three neck round-bottomed flask dried as in the preceding step, 0.3 g PH2AT1.b are added together with 12.5 g 2-chloro-1-methylpyridinium iodide. The flask is connected to a second, dried, single neck round-bottomed flask containing 5.5 g oven-dried 2,2-bis (hydroxymethyl)propionic acid. The medium is placed in an inert atmosphere and immersed in a temperature-controlled bath at 30° C. Using a syringe, 100 mL distilled triethylamine are added and 5 ml anhydrous DMF. Under constant stirring, in successive solid portions, the 2,2-bis(hydroxymethyl)propionic acid is added over a period of 48 h. At the end of the reaction, the mixture is vacuum concentrated at 4 mmHg and extracted several times with dichloromethane. A solid is collected through glass sinter and washed several times with aqueous solutions of pH 6-7 then again with dichloromethane and finally collected and placed in a vacuum oven for 2 days at 35° C. 3.4 g PH2AR1.c are obtained.

Step 4: Methacrylic Functionalization of PH2AT1.c to Obtain PH2AT1:

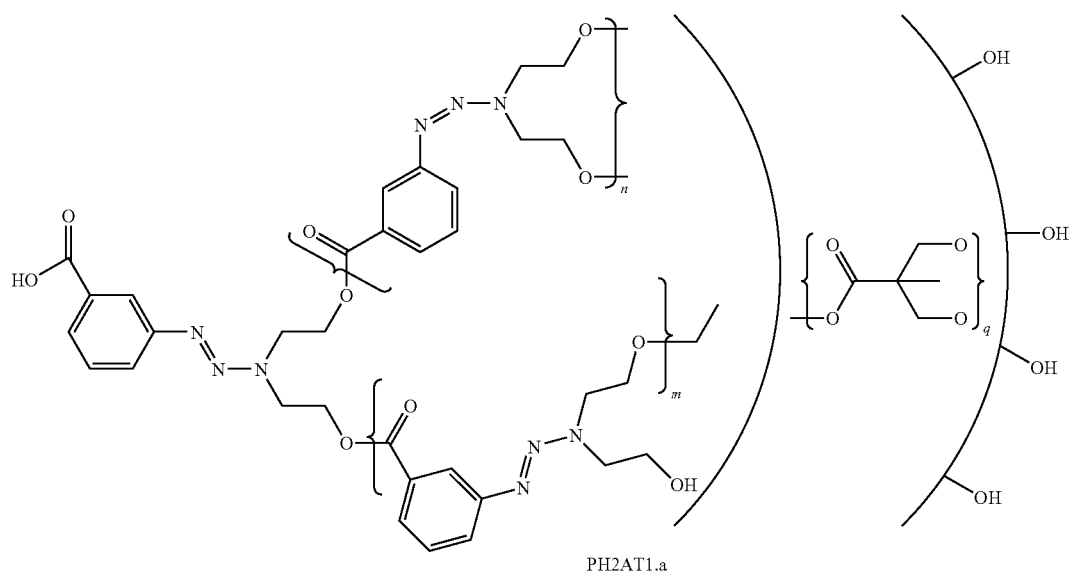

PH2AT1.a

Methacrylic anhydride, DMAP, THF, 50° C.

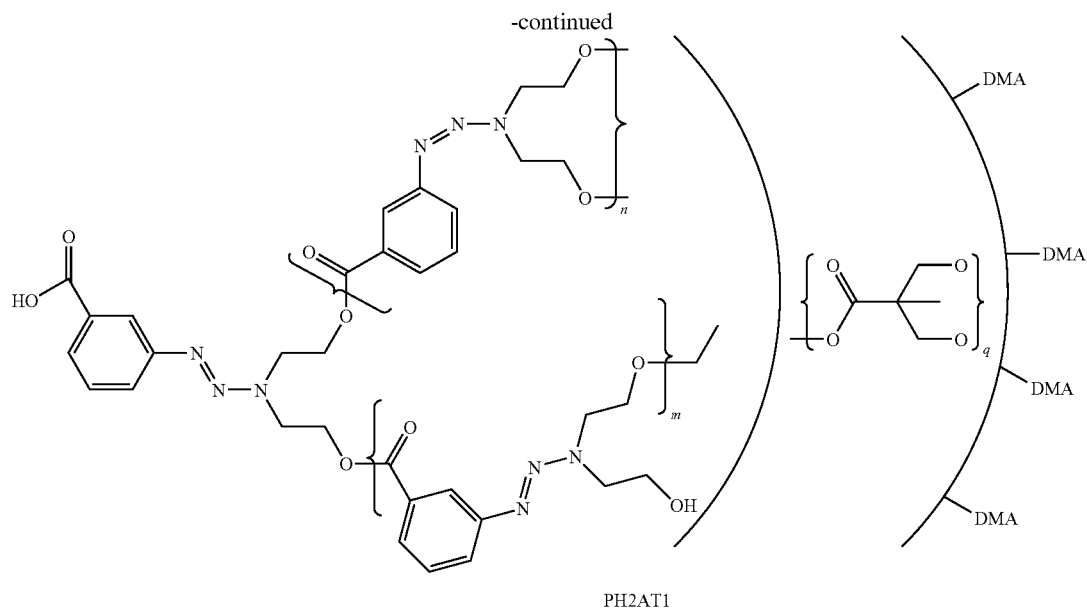

PH2AT1

To an oven-dried three neck round-bottomed flask surmounted by a refrigerant and fitted with an addition funnel, 3.4 g PH2AT1.c are added with 15.37 g DMAP. The medium is brought to 50° C., placed under nitrogen and 500 mL anhydrous THF are added using a syringe. To the addition funnel 13.75 g (0.2 weight % hydroquinone) of methacrylic anhydride are added using a syringe. Finally, 100 mL anhydrous THF are added to the addition funnel and the addition of methacrylic anhydride is started drop by drop for 4 hours under vigorous stirring. When addition is completed, the temperature is left to return to 25° C. overnight. The reaction crude is concentrated in a rotary evaporator and dissolved in 300 mL ethyl acetate. This phase is extracted several times with volumes of 300 mL water at pH 5. The organic phases are grouped together, dried, concentrated and passed through R545 celite with dichloromethane. The organic phases are concentrated, re-dissolved in 300 mL ethyl acetate and extracted with volumes of 300 mL water at pH 5. After drying on magnesium sulfate, the organic phases are concentrated and 3.55 g PH2AT1 are obtained.

According to an essential characteristic of the invention, the photosensitive adhesive composition contains initiation means whose constitutents may be most varied in relation to applications and desired properties. Several variants of the initiation means can be considered, each one suited to the polymerization process (radical, cationic or anionic) chosen by the formulator. In particular, the initiation means may be multiple and in this case the initiation system is a multicomponent initiation system which may give rise to hybrid or dual chain polymerization or crosslinking.

The examples given below do not limit the invention in any way and are intended to enable the formulator to make the best choice among available compounds, in particular in relation to desired use of the adhesive composition of the invention.

In a first variant of initiator means, these are of chemical type.

For radical chain polymerization, examples are limited to the description of particular use in the area of dentistry or medical prostheses. Therefore said initiator means may consist of at least two compounds reacting together under a redox mechanism to generate free radicals. A more particular example, routinely used in dental art, consists of mixing an electron aceptor such as benzoyl peroxide or dibenzoyl peroxide with an electron donor such as tertiary arylamine. Another possible example is the oxide of tri-n-butyl borane.

For cationic chain polymerization, the initiator of chemical type may be chosen from among:

a) Brönsted acids such as perchloric acid, trifluoromethylsulfonic acid, trifluoroacetic acid, iodohydric acid, b) Lewis acids, of which the most common are $BF_3$, $AlCl_3$, $TiCl_4$, $SnCl_4$, $SbCl_5$, the Lewis acid optionally being associated with a weak acid or a cationising agent such as water, a carboxylic ester, a sulfonic ester, an ether or alkyl halide.

Finally, anionic initiation for an adhesive composition of the invention may be used in accordance with the type of polymerizable units chosen, with:

Lewis bases such as benzylsodium, for example, phenylisopropylpotassium or the (n-, sec-, tert-) isomers of butyllithium.

bases such as KOH or amines.

However, for the implementation of this polymerization process, persons skilled in the art may be led to taking some precautions, such as the addition of complexing agents, for example $Et_2Zn$ to protect sensitive functional groups.

Also, anionic initiation of chemical type, for an adhesive composition of the invention, requires special conditions (highly anhydrous conditions, controlled atmosphere for example) which may limit their use to specific applications of the adhesive composition or require the preparation of a polymerized adhesive of the invention that is applied to the surfaces of the items to be bonded after polymerization time.

In addition, the adhesive composition of the invention, coming within the scope of the first variant of the initiator means, is most often in the form of "adhesive sub-compositions" optionally comprising additive solvents, which the formulator must mix before use and before coating the surfaces to be bonded to obtain a complete photosensitive adhesive composition of the invention able to provide required adhesiveness between the parts to be bonded and so as to avoid any premature polymerization of the adhesive composition or any long-term storage problem.

According to a second variant of the initiator means, these may consist of at least one photoinitiator able to initiate the polymerization mechanism under the action of crosslinking radiation whose wavelength λ1 is preferably fairly different to that of uncrosslinking radiation λ2. In this disclosure, λ1 and λ2 designate both single wavelength radiation and ranges of wavelengths centered on the given values. Also, the expression "crosslinking radiation" denotes electromagnetic radiation capable of stimulating the generation of free radicals, cations or anions. The expression "uncrosslinking radiation" denotes electromagnetic radiation capable of causing the hardened adhesive to lose at least part of its integrity.

1—According to a first aspect of this variant of initiation means, these are photoinitiation means at wavelength λ1.

For the mechanism of radical chain polymerization, this first aspect has three versions:

a) In a first version of this aspect, the photoinitiator is of the type able to generate free radicals via a mechanism of homolytic photocleavage. The photoinitiators giving rise to such processes belong to various families and the photoinitiators of the invention may be chosen from the categories derived from the following known examples: benzyl dialkylcetal, benzoin ether, α-hydroxy, α-alkyl phenylketone, cyclohexanol benzoyl, oxides of trimethylbenzoyl phosphine and more generally bis-acyl-oxides of phosphine, α-amino thioalkylphenylketone, α-amino morpholino-phenylketone, sulfonic esters of α-hydroxy methylbenzoin. There also exist numerous other photocleavable initiators in which radical generation occurs subsequent to a series of consecutive homolytic cleaving processes. The chief examples known to persons skilled in the art are the esters of benzoyl oxime, arylarylslsulfides, peroxides, peroxides containing a chromophor such as benzophenone or any alkylphenone, disulfides, ketosulfides and azoic compounds such as AIBN (azobisisobutyronitrile) or azobenzoines.

b) In a second version, the photoinitiator is of the type able to create free radicals through a mechanism of atom snatching. The most frequent class of these photoinitiators is in the one in which a proton is snatched from a substrate during photoreduction of a triplet nπ* state of the photoinitiator, the main examples being the derivatives of benzophenone, of thioxanthones, of benzyl, of 1,2-diketones such as camphorquinone, and ketocoumarins. Formulators have at their disposal other photosensitive compounds, onium salts such as the salts of triarylsulfonium in particular, the salts of alkylarylsulfonium and diarylhalonium salts, largely described in particular by J. V. Crivello. These compounds are generally given wide used as photoinitiators for cationic polymerization (cf. appropriate paragraph below); however, the interaction of the triplet state with a proton donor produces free radicals also enabling initiation of a radical process.

c) The third version concerns the use of photoreducible photoinitiators. The creation of free radicals is consecutive to electron transfer. The families of compounds behaving in this way are chromophors of diarylketone, camphorquinone, ketocoumarin type or aromatic dyes of xanthene, fluorone, thioxanthone, thiazine, acridine, anthraquinone, cyanine, merocyanine, benzopyrane type. The family of photoreducible aromatic dyes is likely to be of especial interest to formulators of dental resins insofar as these photoreducible aromatic compounds are excitable in wavelengths of the visible range.

Regarding cationic chain polymerization, this first aspect also comes in three versions:

a) the photoinitiator is of the type capable of generating a cationic species, more particularly a HX Brönsted acid under λ1 radiation, by direct photodecomposition optionally in the presence of a proton donor, optionally by interacting with polymerizable functions such as epoxide functions for example. The photoinitiators of the invention may be chosen from among the onium salts of diarylhalogenium, triarylsylfonium, dialkylarylsulfonium or dialkyl-phenacylsulfonium type. For example one of the following compounds may be chosen: bis[4-(diphenylsulfonio)-phenyl)sulfide bishexafluorophosphate, triphenylsulfonium tetrafluoroborate, hexafluoroantimonate of (S-methyl-S-dodecyl-S-phenacyl) sulfonium, hexafluoroantimonate of (4-n-decyloxyphenyl) phenyl-iodonium, hexafluorophosphate and tetrakis(pentafluorophenyl)borate of 4-methylphenyl-4-(1-methylethyl-) phenyliodonium.

Conventionally, the counter-anions are chosen from among: $BF_4^-$, $PF_6^-$, $AsF6-$, $SbF_6^-$, $RSO_3^-$. With a view to increasing the sensitivity in the near UV or even the visible, structures may preferably be chosen such as 4-thiophenoxy triarylsulfonium or the alkylaryl derivatives (9-phenylthioanthracenyl)-10 sulfonium, the bisiodonium salts having for example covalent oxy, carbonyl, sulfonyl bridges between the diaryliodonium groups.

b) the photoinitiator is of the type capable of generating a Brönsted acid or Lewis acid under □1 radiation. The photoinitiators of the invention may be chosen from among the diazonium salts in the absence or presence of hydrogen donors.

c) the photoinitiator is of the type capable of generating a cationic species, more particularly a Brönsted acid, under the action of cleavage of a photoinduced covalent bond as is the case for example for derivatives of N-(trifluoromethoxysulfonoxy)phtalimide or of 6,7-(trifluorosulfonoxy)coumarin, the sulfonic esters of 2-nitrobenzyl derivatives, all generating $CF_3SO_3H$.

Finally for this first aspect of the photoinduced initiation variant, formulators may have recourse for anionic chain polymerization to the following compounds given as examples:

halides of trimethylfluorenylammonium and trimethylbenzydrylammonium;

base photogenerating o-nitrobenzyl derivatives, for example dimethyl 4-(o-nitrophenyl)-2,6-dimethyl-1,4-dihydro-3,5-pyridinedicarboxylate, derivatives of 2-nitrobenzyl-carbamates, bis(benzophenone oxime) N,N'-hexamethylene diurethane, N-alkylated nifedepine;

O-acyloxime derivatives such as O-phenylacetyl-2-acetonaphthone;

quaternary ammonium dithiocarbamates.

2—According to a second aspect of the photoinitiation variant, the initiation system may be a bi-component system (photoinitiator+co-initiator). Within the present invention, the description of this aspect is limited to radical chain polymerization in which the two components together produce electron transfer under radiation at wavelength λ1. This is only a particular case of the concept of bi-component photoinitiation.

One possibility is the combination of an electron acceptor photosensitive species and an electron donor species. This combination is generally the one that is most described it enables numerous associations to be considered. Hence, the electron acceptor photosensitive species include all the families previously set forth in respect of photoreducible photoinitiators. Within this strategy, the electron donor species accelerates radical polymerization over a two-step process, namely electron transfer followed by proton transfer. Numerous species exist that are able to interact with photoreducible species and compounds may be chiefly cited which include an activated nitrogen atom such as triethanolamine, a tertiary amine or a tertiary arylamine (N,N-dimethyl-p-toluidine, N,N-diethanol-p-toluidine, N,N-dimethyl-sym(m)xylidine, 3,5-di-tert-butylaniline, N,N-dimethyl-p-ethyl aminobenzoate), the compounds comprising an activated nitrogen and sulfur atom such as the thiazole derivatives (mercaptobenzothiazole), boron salts (borate) such as tetraphenylborates or butyltriphenylborates and other salts of tetraalkylammonium tetraorganylborate type.

Onium salts also hold an important place among bi-component systems when associated with boron salts, such as the derivatives of tetraphenylborate and, more preferably, derivatives of butyltriphenylborate. On account of strong absorption below a wavelength of 300 nm and a "tail" of the absorption spectrum in the visible beyond a wavelength of 400 nm, even 430 nm in some cases, these compounds are photosensitive both in the UV and in the visible range.

3—According to a third aspect of the photoinitiation variant, the initiation system is a a photoinitiation system comprising, in addition to the photoinitiator proper, at least one species able to photosensitize the initiator means creating the active centres (free radicals, cations or anions); this species is called photosensitizer. In this case, the interaction between the photosensitizer in one of its excited states with the photoinitiator may principally, this description not being exhaustive, be of two types. Photosensitization operates either by singlet state-singlet state or triplet state-triplet state energy transfer, or by electron transfer photoinduced with the photosensitizer, or else by both at the same time.

If at least one of the photoinitiators is of the type able to generate free radicals by homolytic photocleavage mechanism, then a certain number of systems exist in the literature which enable this process to be accelerated. For example an important class of initiators is the peroxides, but the photosensitization mechanisms are most varied. For example, benzoyl peroxide, decanoyl peroxide may be photosensitized by energy transfer from the triplet state of compounds such as anthracene, acetophenone, methoxy- and cyanobenzophenones, associated with the formation of a charge transfer complex. In other cases, electron transfer is involved as between a thioxanthene for example with 3,3',4,4'-tetra-(t-butylperoxycarbonyl)-1-benzophone. These examples are only given by way of indication, having regard to the variability of sensitization mechanisms in relation to operating conditions and the chemical species involved.

Other examples of importance concern the interaction which exists bewteen an α-amino acetophenone (e.g. □-morpholino thiomethylphenylketone) and a photosensitizer of thioxanthone type. This system has the particular feature of being able to function both by energy transfer from the triplet state of thioxanthone and by electron transfer.

It is also possible to photosensitize some bi-component systems which associate an electron donor and acceptor. In particular, the onium salt, "intermediate" photoreducible sensitizer and electron donor trio is very efficient in initiating acrylic formulations. In particular the following combinations may be made between:

an onium salt chosen from among the diaryliodonium salts and triarylsulfonium salts, an intermediate photosensitive and photoreducible species chosen from among the categories designated by the following examples: di(aminoarylketone), ketocoumarin, thioxanthone, xanthene, fluorone, thiazine, acridine, anthraquinone, cyanine, merocyanine and benzopyrane, and an electron donor such as the compounds containing an activated nitrogen atom, for example a tertiary amine and a tertiary arylamine (N,N-dimethyl-p-toluidine, N,N-diethanol p-toluidine, N,N-dimethylsym(m)xylidine, 3,5-di-tert-butyl-aniline, N,N-dimethyl-p-ethyl aminobenzoate), the compounds containing an activated nitrogen and sulfur atom such as the derivatives of thiazole (mercaptobenzothiazole), boron salts (borate) such as tetraphenylborates or butyltriphenylborates, and other salts of tetraalkylammonium tetraorganylborate type.

The system may be considered differently depending upon whether the "intermediate" species or the onium salt is considered as photosensitizer.

Also, another series of examples applicable to the scope of the invention relates to the photosensitization of an onium salt, of triarylsulfonium or diarylhalogenium salt type used, without association, with an electron donor of tertiary amine or borate salt type (but optionally associated with a suitable proton donor). Formulators may then optionally choose to photosensitize through addition of a photosensitive compound enablng triplet-state triplet-state energy transfer chosen from the following list: acetone, 1-indone, acetophenone, 3-trifluoromethyl-acetophenone, xanthone, or by incorporating a photosensitive compound enabling electron transfer with an onium salt chosen from among: anthracene, pyrene, perylene, aromatic ketones such as benzophenone, Michler ketones, xanthones, thioxanthones, derivatives of dimethyl aminobenzylidine, phenanthraquinones, eosine, ketocoumarins, acridines, benzofuranes.

For cationic polymerization reaction, the photoinitiating system in addition to the photoinitiator chosen from among the onium salts, also comprises at least one photosensitizer of this photoinitiator. The advantage of this combination is to accelerate photopolymerization and to extend the spectral response of the photoinitiation system.

The photosensitization mechanisms of onium salts are complex and the composition of the invention may, as examples, comprise the following combinations (examples have already been given for photosensitization under radical initiation):

onium salts and aromatic polycycles such as derivatives of anthracene, fluorene, pyrene;

onium salts and dyes such as xanthene, thioxanthene, merocyanine, acridone, tetrabenzoporphyrine, flavine, acridine;

onium salts and carbazole derivatives;

onium salts and metal salts able to achieve electron transfer towards the iodonium salt;

onium salts and ketones such as thioxanthones for example, derivatives of benzophenone, ketocoumarins, 1,2-diketones such as camphorquinone, derivatives of anthraquinone;

onium salts and generators of radicals such as benzoin ether for example, dialkoxyacetophenone or phosphine oxide benzoyl.

4—According to a final particularly privileged aspect of this variant of initiation means for the polymerization reaction, the latter are initiation means of photochemical type, whose composition may include at least one photoinitiator, at least one co-initiator, at least one photosensitizer or, more generally, any adequate combination between the different potential components of a photoinitiation system, such as described under 1-, 2- and 3- above, with a view to increasing its efficacy and/or to modify its absorption range of electromagnetic radiation.

According to a third variant of the initiation means for the polymerization reaction of the adhesive composition of the invention, the initiation means are of thermal type. This variant can be given more particular consideration for radical polymerization. A great number of thermal radical initiators exist in the literature. Non-limitative examples are: AIBN, benzoyl peroxide, tert-butyl hydroperoxide, tert-butyl peracetate, tert-butyl peroxide, dicumyl peroxide and others.

Finally, a last variant of polymerization initiation means is a global variant integrating all possible, compatible combinations of initiation means such as described previously in the first, second and third variants. This choice may prove to be a shrewd choice since it can provide improved crosslinking of the adhesive and improved physicochemical properties. For example, in dental use, a post-polymerization or post-crosslinking agent may be added to a camphorquinone/tertiary arylamine system, the agent possibly being a peroxide such as dibenzoyl peroxide.

To conclude, it will be noted that in the case of a radical polymerization mechanism, the vinyl units forming a donor/acceptor pair presented above are also radical initiation means.

It will be easily understood that formulators may evidently combine several types of bifunctional monomers within one same adhesive composition of the invention. Particular attention must be given to the wavelength ranges used. Preference is given to the combination of bifunctional compounds for which wavelength □2 is identical or overlapping, and whose photoinitiation wavelengths λ1 are fairly different. However, if the photoinitiator used is very efficient and if the concentration of photocleavable units is reasonable, consideration may be given to the overlapping of absorption ranges λ1 and λ2 if the kinetics of active centre generation by the photoinitiator are much greater than the kinetics of bifunctional monomer cleavage, which may translate as exposure of the material to lower radiation powers, longer lamp distances etc.

Also, monomers may advantageously be combined which polymerize by different processes, taking care that initiation means for the polymerization reactions are adequated, so as to form interpenetrating networks whose advantages are well known: mechanical synergy, improved resistance over time and increased snatch resistance.

According to an essential characteristic of the invention, the bifunctional monomers must be present in sufficient quantity in the adhesive composition to obtain loss of integrity and adhesiveness of the hardened composition when it is subjected to uncrosslinking radiation. The minimum quantity is 0.5 weight % of the adhesive composition. The optimum quantity of bifunctional monomers to obtain the desired loss of integrity of the adhesive is related to several parameters, in particular the photoreactivity of the photocleavable units, the structure of the bifunctional monomers, the presence and type of co-monomers or reactive diluents of the adhesive composition. Generally, the quantities are low if the glass transition temperature of the polymerized adhesive is less than −30° C. for example, and greater if the adhesive compositions are highly charged and/or crosslinked.

Evidently, the adhesive composition of the invention may, in addition to the bifunctional monomers and initiation means, comprise other constituents in particular:

co-monomers polymerizable by a chain polymerization mechanism, which may act as reactive diluent, and which may be of same type as the polymerizable units described previously or they may be any polymerizable unit conventionally used in adhesive resins;

a component carrying at least one thiol function, such as those cited in U.S. Pat. Nos. 4,663,416 and 4,780,486;

a polyalkenoic acid such as a copolymer of itaconic and polyacrylic acid, for example, various fillers which may be organic and/or inorganic, in particular of silica type (optionally silanized) or of ionomer glass type such as $CaF_2$, $YF_3$, $AlF_3$, more generally suitably formulated fluoroaluminosilicate glasses;

additives such as those usually used in adhesive compositions and intended to improve some of their physicochemical properties, such as solvents (water and organic), pigments, stabilizers, surfactants, plastifiers, etc.

The multiple possible combinations enable best adjustment of viscosity or fluidity of the adhesive composition, in relation to needs connected with end use.

Also, it will be understood that the photosensitive adhesive composition of the invention is applicable to numerous areas having regard to the multiplicity of possible variants. Special consideration is given to dental use for cementing elements to the surface of teeth and/or to fill dental cavities.

In respect of the positioning of bands for orthodontic correction, the enamel surface of the teeth is prepared by cleaning and optional mordant preparation using appropriate products. Then, the adhesive composition of the invention is applied to the prepared area, the bands are placed in position on the adhesive layer which is then hardened by photopolymerization for example.

Once correction has been completed, the bands are removed by subjecting the hardened adhesive to uncrosslinking radiation which disrupts the integrity of the adhesive and makes it possible to separate the bands from the enamel surface of the teeth without causing any mechanical damage to this surface.

The adhesive composition may also be used to ensure temporary closing of a tooth root canal. For this purpose, after conventional root dressing and preparation, the root canal is filled as far as the apex of the tooth with the adhesive of the invention, then a master-cone is inserted inside the root canal of similar length to the root canal. This master-cone is made of material able to convey crosslinking/uncrosslinking radiation on its outer end towards the inside of the tooth and to diffuse the same towards the canal wall so that the root sealing adhesive of the invention can be easily removed without causing any damage to the integrity of the root canal.

Several examples of photosensitive adhesive compositions in the UV/visible ranges especially intended for dental application are given below.

Evidently, these examples can be transposed to any other industrial sector in which there is a need for temporary adhesiveness, which can be controllably released and without the use of complex or hazardous equipment by operators. Special consideration is given to all systems intended to be subsequently recycled, in which the use of an adhesive of the invention enables very easy separation of various bonded elements.

Attention must be given however to the efficacy of the cleavage generated by uncrosslinking actinic radiation. In this respect it is possible to increase the proportion of bifunctional monomers. It is also possible to contemplate inserting an optic fibre guide inside the bonded joint with an external access point which may be used to transmit actinic radiation for polymerization and then cleavage to the entire bonded joint. The other alternative consists of using the photosensitive adhesive of the invention to bond parts whose material or form are advantageously designed so that they can allow the passing of at least the uncrosslinking wavelength λ2, initiation of polymerization possibly being chemical.

Finally, the photosensitive adhesive composition of the invention may evidently comprise bifunctional compounds that are polymerizable and cleavable in wavelength ranges other than those described, and the examples of composition given below are evidently only particular illustrations which do not in any way restrict the areas of application of the photosensitive adhesive composition of the invention.

EXAMPLES OF PHOTOPOLYMERIZABLE FORMULATIONS OF THE PHOTOSENSITIVE ADHESIVE COMPOSITION OF THE INVENTION FOR USE IN DENTISTRY

In the following examples, the mechanical properties of adhesive compositions were tested whose formulation comprises one or more bifunctional monomers.

The different constituents are dispersed in a minimum volume of ethyl ether. The mixtures are homogenized by ultrasound under magnetic stirring and are then concentrated and placed in a vacuum of 4 mmHg for one hour.

The formulations are arranged in a Teflon mould whose base is a glass slide to give bars of size (14 mm×4 mm×1 mm) after polymerization. Polymerizations (λ1) are conducted using an Efos Lite Mercury-Xenon 50 W lamp positioned at a distance of 0.5 cm from the surface of the sample and, unless otherwise indicated, using an interference filter allowing radiation of between 426 and 480 nm to pass. The sample is irradiated 150 s on each side, unless otherwise specified. Successive irradiations (λ2) are performed using the same lamp positioned at 0.2 cm from the sample with an interference filter allowing radiation of between 320 and 480 nm to pass. The sample is irradiated 600 s on each side.

The mechanical properties were evaluated with DMA (Dynamic Mechanical Analysis) following a 3 bend-point mode after polymerization at λ1 and after degradation at λ2.

For all tested compositions, fissuring was observed in the structure of the sample after degradation.

The weight percentages of the constituents marked with an asterisk (*) are given in relation to the total weight of the monomers (all polymerizable organic compounds).

Example 1

Cationically Polymerizable Composition

The composition given below may be used in particular for cementing applications, but can be used for other dentistry operations.

The sample is polymerized by 300 s radiation on each side.

| Component | weight % |
| --- | --- |
| 3,4-epoxycyclohexylmethyl 3,4-epoxycyclohexanecarboxylate | 22 |
| Cyclohexene oxide | 4 |
| NTS | 14 |
| Bis-(4-dodecylphenyl)iodinium hexafluoroantimonate* | 1.5 |
| Camphorquinone* | 0.75 |
| Ethyl 4-dimethylaminobenzoate* | 0.4 |
| Cem-bridge type filler (Pierre Rolland dental products) | 60 |

The elastic modulus measured at 25° C. after photopolymerization is 2.20 GPa and 0.95 GPa after degradation.

Example 2

Anionically Polymerizable Composition

The composition given below may be given particular application for cementing but can be used for other operations in the area of dentistry.

In this particular case, wavelength λ1 lies between 400 and 480 nm and polymerization times are 300 s on each side.

| Component | weight % |
| --- | --- |
| 3,4-epoxycyclohexylmethyl-3,4-epoxycyclohexanecarboxylate | 4 |
| Bis-(3,4-epoxycyclohexylmethyl)adipate | 20 |
| AT9 | 16 |
| N-methylnifedipine* | 1.5 |
| Cem-bridge type filler (Pierre Rolland dental products) | 60 |

The elastic modulus measured at 25° C. after photopolymerization is 2.40 GPa and 1.15 GPa after degradation.

Example 3

Radically Polymerizable Composition

The composition given below preferably has clinical applications for cavity filling and cementing, in particular for root canal work, fissures and anchoring.

| Component | weight % |
| --- | --- |
| Bisphenol A dimethacrylate | 9.2 |
| Hydroxyethyl methacrylate | 6.2 |
| Butyl methacrylate | 3.6 |
| Triethyleneglycol dimethacrylate | 12.1 |
| PU1AT1 | 30.7 |
| (4-n-decyloxyphenyl)phenyl-iodinium SbF$_6^-$* | 1 |
| Camphorquinone/4-ethyl dimethylaminobenzoate* | 0.5 |
| Benzoyl peroxide* | 0.3 |
| Revolution Formula 2 filler (Kerr) | 38.2 |
| Hydroquinone methyl ether* | 0.2 |

The modulus of elasticity measured at 25° C. after photopolymerization is 2.90 GPa and 0.70 GPa after degradation.

Example 4

Radically Polymerizable Composition

The composition given below has preferable clinical application for restorative dental operations using composites.

| Component | weight % |
| --- | --- |
| Urethane Dimethylacrylate | 3.4 |
| Butyl Methacrylate | 2.3 |
| Polyethylene glycol dimethacrylate Mn~875 | 2.3 |
| Triethyleneglycol dimethacrylate | 4.5 |
| PH2AT1 | 7.15 |
| AT3 | 3.6 |

-continued

| Component | weight % |
| --- | --- |
| (4-n-decyloxyphenyl)phenyl-iodinium SbF$_6^-$ | 1 |
| Camphorquinone/4-ethyl dimethylaminobenzoate* | 0.5 |
| Benzoyl Peroxide* | 0.3 |
| Kappalux M filler (Pierre Rolland dental products) | 76.75 |
| Hydroquinone methyl ether* | 0.2 |

The elastic modulus measured at 25° C. after photo-polymerization is 8.20 GPa and 1.30 GPa after degradation.

Example 5

Radically Polymerizable Composition

The composition given below has preferable clinical application for orthodontic cementing, in particular the cementing of metallic and/or ceramic parts to a tooth

| Component | weight % |
| --- | --- |
| Urethane dimethacrylate | 5.8 |
| Hydroxyethyl methacrylate | 7.26 |
| Triethyleneglycol dimethacrylate | 5.8 |
| NT4 | 10.20 |
| Irg 819* | 1 |
| Glycerol Phosphate Dimethacrylate | 1 |
| Cem-bridge filler (Pierre Rolland dental products) | 69.94 |
| Hydroquinone methyl ether* | 0.2 |

The elastic modulus measured at 25° C. after photo-polymerization is 4.65 GPa and 0.80 GPa after degradation.

The invention claimed is:

1. A photosensitive adhesive composition of polymerizable resin type whose hardening is obtained by polymerization and/or cross-linking characterized in that said composition contains:
at least one chain polymerization reaction initiator that ensures hardening of said composition, and
a sufficient quantity of at least one bifunctional monomer including firstly a photocleavable centre comprising at least one photocleavable unit selected from the group consisting of:
(i) aryl-diazos units defined by formula I:

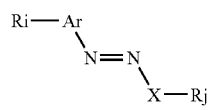

in which:
Ar designates an aromatic system, monocylic or polycylic, carbocyclic or heterocyclic,
X designates an atom chosen from among: C,O,P,S;
Ri is one or more of the following groups: hydrogeno, halogeno, alkyl linear or branched, saturated or unsaturated, optionally substituted, aryl aromatic or heteoaromatic, substituted or unsubstituted, alcoxy comprising at least one selected from the group consisting of methoxy, ethoxy, aryloxy, alkylthio, arylthio, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group, —OCO$_2$R', —OSO$_2$R', —OPOOR'OR", -R'NHCOOR", —R'OCO$_2$R", —NR'R" (in which R' and R" represent an alkyl group, carbocyclic or heterocyclic group, aliphatic, unsaturated, (hetero-)aromatic group, all substituted or unsubstituted, imine whether substituted or not, nitro, —N=N—R', -Rp-Si—(ORq)$_3$ group (in which Rp is a hydrocarbon chain or a linear alkyl chain comprising at least 3 C atoms, and Rq denotes a hydrogen atom, a hydroxy group, C$_1$-C$_6$ alcoxy chain or —(Si(ORq) group), vinyl group, acrylic group, alcoxycarbonyl group, and an aryltriazene group,
Rj designates one or more substituents depending upon the valency of the atom designated by X, the same or different and chosen from among: an alkyl chain linear or branched, saturated or unsaturated, acyclic or cyclic, optionally substituted; an aromatic or heteroaromatic group including, at least one nitrogen or sulfur atom, monocyclic or polycyclic; an alcoxy, aryloxy chain or benzyl group;
(ii) aryl-triazene units defined by formula II:

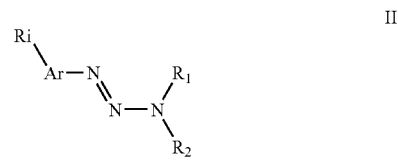

in which:
Ar designates an aromatic system monocyclic or polycyclic, carbocyclic or heterocyclic,
Ri is chosen from among the following groups: alkyl linear or branched, saturated or unsaturated, optionally substituted, aryl aromatic or heteoaromatic, substituted or unsubstituted, alcoxy comprising one selected from the group consisting of methoxy, ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group or —OCO$_2$R', —OSO$_2$R', —OPOOR'OR", —R'NHCOOR", —R'OCO$_2$R", —NR'R" (in which R' and R" represent an alkyl group, a carbocyclic or heterocyclic group, aliphatic, unsaturated, a (hetero-)aromatic group, all substituted or unsubstituted, imine substituted or unsubstituted, nitro, —N=N—R', -Rp-Si—(ORq)$_3$ group (Rp and Rq as previously defined above), a vinyl group, acrylic group, alcoxycarbonyl group, and an aryltriazene group,
R$_1$ and R$_2$ are chosen independently from one another, a —N=N—R' group, —NR'—N=N—R" group, OH group, NR'R" group, (R' and R" have the previously given denotations), an alkyl group comprising at least one selected from the group consisting of methyl, ethyl, propyl, isopropyl, butyl, tert-butyl, an alcoxy group substituted or not, a benzyl group, a (hetero)-aromatic group, all substituted or not by substituents of Ri type, a hydroxyethyl, cyanoethyl, aminoethyl, acryloxyethyl, and halogenoethyl group (iii) 2-nitrobenzyl units having the formula 1:

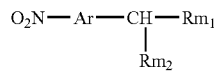

in which:
- Ar designates an aromatic or heteroaromatic radical monocyclic or polycyclic and carrying at least one Rk substituent,
- Rk designates an auxochromic or bathochromic substituent which may be chosen from the following examples: hydrogen, halogen, alkyl chain, aliphatic acyclic saturated or unsaturated, linear or branched, a cyclic, aliphatic, unsaturated, aromatic or heteroaromatic radical, these chains and radicals possibly being substituted, interrupted or terminated by a heteroatom comprising at least one selected from the group consisting of B, N, O, Si, P, S and a halogen, a nitro group, cyano group, an alcoxy, aryloxy, alkylthio, arylthio, benzyl, aylalkyl, hydroxy, thiol, alkyloxycarbonyl, aryloxycarbonyl, carbonyl, formyl, amino radical, carboxylic ester, amide, sulfonic ester, sulfonic amide, carboxylic acid, sulfonic acid, sulfonate, phosphonate, a —OCONR'R" group, —OCO$_2$R', —OSO$_2$R', —OPOOR'OR", —R'NHCOOR", R'OCO$_2$R", NR'R" (R' and R" are an alkyl, aryl group, a carbocyclic or heterocyclic group), imine substituted or unsubstituted, diazo —N=N—R', -Rp-Si(ORq)$_3$ group, alkylglycidyl ether, alkylvinyl ether, cyclohexyl epoxy,
- $R_{m1}/R_{m2}$ are independently chosen from among: a hydrogen, an alkyl, alcenyl, alcynyl, alkylaryl chain, all substituted or unsubstituted, a carbocyclic or heterocyclic chain saturated or unsaturated, aromatic or heteroaromatic, substituted or unsubstituted, an alcoxy, aryloxy, alkylthio, arylthio chain, an alkyloxocarbonyl group, —NR'COR" group, —OCOR' group, —OCOOR' group, —OCONR'R" group, NR'COOR" group, —OPOR'R"R'" group, —OSO$_2$R' group, —OPOOR'OR" group, —NR'R", —COOR' group, —CONR'R", SOOR', —COR' group (R', R" and R'" have the previously indicated denotations for R' and R" an imine group substituted or unsubstituted, a hydroxy, thiol group, a carboxylic acid or derivative of carboxylic acid, a halogen, a nitrile, an alkyl(C1-C6)glycidyl ether group, alkyl(C1-C6)vinyl ether group, cyclohexyl epoxy, -Rp-Si—(ORq)$_3$ group (Rp and Rq as previously defined above)

(iv) 2-nitrobenzyl units defined by formula 2:

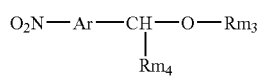

in which:
- Ar is an aromatic system, monocyclic or polycyclic, carbocyclic or heterocyclic,
- $R_{m4}$ is defined as Rm1/Rm2,
- $R_{m3}$ is chosen from among a hydrogen, an alkyl, alcenyl, alcynyl, alkylaryl chain, all substituted or unsubstituted, interrupted by a heteroatom, a carbocyclic or heterocyclic chain, saturated or unsaturated, aromatic or heteroaromatic, substituted or unsubstituted, an alkyloxocarbonyl group, NCOOR' group, —POR'R"R'" group, —SO$_2$R' group, —POOR'OR" group, —COOR' group, —CONR'R", COR' group (R', R" and R'" having the previously indicated denotations for R' and R"), an alkyl (C$_1$-C$_6$)glycidyl ether group, alkyl(C1-C6)vinyl ether group, cyclohexyl epoxy, -Rp-Si(ORq)$_3$ group (Rp and Rq as previously defined above), (v) 2-nitrobenzyl units defined by formula 3:

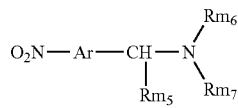

in which:
- Ar is defined as previously,
- $R_{m5}$ is defined as $R_{11}/R_{12}/R_{13}$,
- $R_{m6}/R_{m7}$ are defined as a hydrogen, an alkyl, alcenyl, alcynyl, alkylaryl chain, substituted or not, interrupted by a heteroatom, a carbocyclic or heterocyclic chain, (un)saturated, (hetero)-aromatic, substituted or not, an alkyloxycarbonyl group, —R'COR" group, R'COOR" group, R'R", —COOR' group, —CONR'R", a COR' group (R' and R" having the denotations previously given), a hydroxy group, alkyl(C1-C6)glycidyl ether or alkyl(C1-C6)vinyl ether, cyclohexyl epoxy, -Rp-Si (ORq)$_3$ group (Rp and Rq as defined previously above), and (vi) 2-nitrobenzyl units defined by formula 4:

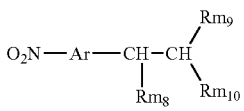

in which:
- Ar is defined as previously,
- $R_{m8}/R_{m9}/R_{m10}$ are defined as $R_{11}/R_{12}/R_{13}$ as defined above; and secondly at least two polymerizable units linked by covalent skeletons to said photocleavable centre and positioned either side of the cleavage site or sites of said photocleavable centre so that said hardened composition loses its integrity and adhesiveness under the action of uncrosslinking radiation which causes cleavage of the photocleavable units.

2. The adhesive composition as in claim 1, wherein the initiation means for chain polymerization reaction(s) are photoinitiating means consisting of at least one photoinitiator able to initiate the polymerization reaction mechanism under the action of crosslinking radiation whose wavelength λ1 is different to wavelength λ2 for uncrosslinking radiation.

3. The adhesive composition as in claim 1, wherein X designates P and in that the photocleavable unit(s) of the photocleavable centre are arylazophosphonate units Ar—N=N—PO(OR') (OR"), in which R' and R" are independently chosen from among: an alkyl chain linear or branched, substituted or unsubstituted, (un)saturated, (a)cyclic, carbocyclic or heterocyclic, a (hetero)-aromatic radical, a hydroxyethyl chain, 1,4- or 1,3-dimethyl cyclohexyl, 1,4dimethylparaphenyl, a methyl, ethy, propyl, isopropyl, hydroxyethyl, cyanoethyl, acryloxyethyl group, ether of alkyl (C$_1$-C$_6$)glycidyl or alkyl(C$_1$-C$_6$)vinyl, cyclochexyl epoxy.

4. The adhesive composition as in claim 1, wherein X designates S and in that the photocleavable unit(s) of the photocleavable centre are arylazosulfonates Ar—N═N—So(OR') (OR"), R' and R" being independently chosen from among: an alkyl chain linear or branched, substituted or unsubstituted, (un)saturated, (a)cyclic, carbocyclic or heterocyclic, a (hetero)-aromatic radical, a hydroxyethyl chain, 1,4- or 1,3-dimethyl cyclohexyl, 1,4-dimethylparaphenyl, a methyl, ethy, propyl, isopropyl, hydroxyethyl, cyanoethyl, acryloxyethyl group, ether of alkyl($C_1$-$C_6$)glycidyl or alkyl ($C_1$-$C_6$)vinyl, cyclochexyl epoxy.

5. The adhesive composition as in claim 1, wherein X designates S and in that the photocleavable unit(s) of the photocleavable centre are arylazosulfone units Ar—N═N—$SO_2$R', R' being independently chosen from among: an alkyl chain linear or branched, substituted or unsubstituted, (un)saturated, (a)cyclic, carbocyclic or heterocyclic, a (hetero)-aromatic radical, a hydroxyethyl chain, 1,4- or 1,3-dimethyl cyclohexyl, 1,4-dimethylparaphenyl, a methyl, ethy, propyl, isopropyl, hydroxyethyl, cyanoethyl, acryloxyethyl group, ether of alkyl($C_1$-$C_6$)glycidyl or alkyl($C_1$-$C_6$)vinyl, cyclochexyl epoxy.

6. The adhesive composition as in claim 1, wherein X designates S and in that the photocleavable unit(s) of the photocleavable centre are arylazosulfide units AR—N═N—S—R', R' being independently chosen from among: an alkyl chain linear or branched, substituted or unsubstituted, (un)saturated, (a)cyclic, carbocyclic or heterocyclic, a (hetero)-aromatic radical, a hydroxyethyl chain, 1,4- or 1,3-dimethyl cyclohexyl, 1,4-dimethylparaphenyl, a methyl, ethy, propyl, isopropyl, hydroxyethyl, cyanoethyl, acryloxyethyl group, ether of alkyl($C_1$-$C_6$)glycidyl or alkyl($C_1$-$C_6$)vinyl, cyclochexyl epoxy.

7. The adhesive composition as in claim 1, wherein the polymerizable units to linked to the photocleavable units to form the bifunctional monomer are radically polymerizable and are vinyl groups defined by formula IV:

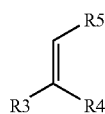

in which R3, R4, R5 are substituents able to activate together the double vinyl bond vis-à-vis radical addition chain reactions, at least one of said substituents being a hydrocarbon chain advantageously a C1-C6 alkyl chain.

8. The adhesive composition as in claim 7, wherein at least one of the substituents R3, R4 and R5 is chosen from among the groups: aryl, carbonyloxyalkyl, carbonyloxyaryl, carboxy (—COOH), alcoxy-carbonyl (—$O_2$CR), carbamoyl (—$CONR_2$) and cyano.

9. The adhesive as in claim 2, wherein said composition comprises at least two types of complementary vinyl units, capable of creating a charge transfer complex (electron donor/acceptor pair) itself able to initiate a radical reaction under the action of crosslinking radiation of wavelength λ1, or at least one type of acceptor vinyl unit able to create a charge transfer with another complementary species.

10. The adhesive composition as in claim 9, wherein the donor vinyl unit is chosen from among the elements: styrene, vinyl acetate, vinyl ether, exomethylene dioxolane, 4-methylene-2-phenyl-1,3-dioxolane, alkyl methacrylate, vinyl pyrrolidone, vinyl carbazole, vinyl naphthalene, while the vinyl unit of acceptor type is chosen from among the elements: maleic anhydride, acrylonitrile, diethyl fumarate, fumaronitrile, maleimides.

11. The adhesive composition as in claim 1, wherein the polymerizable units to be linked to the photocleavable units to form the bifunctional monomer are radically polymerizable and are oxirane groups defined by formula V:

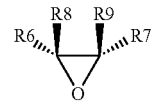

in which at least one of the substituents R6, R7, R8, R9 is a hydrocarbon chain and are chosen from among a hydrogen atom, halogen atom, an alkyl, alcoxy, alkylthio chain linear or branched, saturated or unsaturated, acyclic or cyclic, optionally substituted, optionally interrupted by a heteroatom, an aromatic or heteroaromatic aryl group, an aryloxy or arylthio group, a benzyl group, imine group, amino NR'R", SiR'R"R''', alkyl(C1-C6)oxycarbonyl, aryl(C1-C6)oxycarbonyl, amide, carboxylic and sulfonic ester, sulfonate, phosphonate, a carbonyl group, cyano, —OCONR'R" group, —$OCO_2$R' group, —$OSO_2$R' group, —OPOOR'OR" group, —R'NHCOOR", R'O$CO_2$R" in which R, R', R" represent an alkyl group substituted or unsubstituted, aryl carbocyclic or heterocyclic group, aliphatic, unsaturated or aromatic, substituted or unsubstituted.

12. The adhesive composition as in claim 11, wherein for reasons of steric hindrance, two of the substituents R6, R7, R8, R9 are a hydrogen atom.

13. The adhesive composition as in claim 1, wherein the polymerizable units to be linked to the photocleavable units to form the bifunctional monomer are radically polymerizable and are vinyl ethers defined by formula VI:

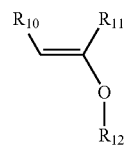

in which:
R10 and R11 are the same or different and designate a hydrogen atom or advantageously a linear or branched $C_1$-$C_6$ alkyl chain, substituted or not, saturated or unsaturated, acyclic or cyclic, optionally interrupted by a heteroatom, an aromatic or heteroaromatic aryl group, an alcoxy chain, alkylthio chain, arylthio,
R12 advantageously designates a linear or branched $C_1$-$C_6$ alkyl chain, substituted or not, saturated or unsaturated, acyclic or cyclic, optionally interrupted by a heteroatom, an aromatic or heteroaromatic aryl group.

14. The adhesive composition as in claim 1, wherein the bifunctional monomer is of oligomer or prepolymer size and has a comb branch structure, consisting of a principal linear polymer chain of which each of the comb branches contains at least one photocleavable unit positioned on the side of the principal chain and at least one polymerizable unit positioned at the free end of the branch.

15. The adhesive composition as in claim 14, wherein the comb branches contain a photocleavable unit and a polymerizable unit.

16. The adhesive composition as in claim 1, wherein the bifunctional monomer is of oligomer or prepolymer size and has a hyperbranched structure.

17. The composition as in claim 16, wherein the bifunctional monomer with hyperbranched structure is synthesized from a precursor monomer of $AB_2$ or $AB_3$ type, under a polycondensation or polyaddition mechanism.

18. The adhesive composition as in claim 16, wherein the hyperbranched structure has a core comprising photocleavable units, and a peripheral shell consisting of inert units from a photochemical viewpoint.

19. The adhesive composition as in claim 16, wherein the hyperbranched structure has a core consisting of photochemically inert units, and a peripheral shell containing photocleavable units.

20. The adhesive composition as in claim 7, wherein the bifunctional monomer is 1,5-bis[4'-(methacryloylmethyl) phenylazomethyl-phosphonate]-diethylene glycol.

21. The adhesive composition as in claim 11, wherein the bifunctional monomer is: 1,5-bis [4'-methyl glycidyl ether) phenylazomethylphosphonate]-diethylene glycol.

22. The adhesive composition as in claim 7, wherein the bifunctional monomer is chosen from: 1,2-Bis[1-(4"-(methacryloylmethyl-)phenyl-3-methyl]triaz(1)ene-ethane; 1,2-Bis[1-(4'-(methacryloylethyl)aminocarbonyloxymethyl) phenyl-3-methyl-]triaz(1)ene-ethane; 1-(4'-methacryloylmethyl-)phenyl-3-(2"-methacryloylethyl-)-3-methyl-triaz(1)ene; 1-(4'-(methacryloylethyl)aminocarbonyl oxymethyl)phenyl-3-((methacryloylethyl)aminocarbonyloxyethyl)-3-methyl-triaz(1)ene; 1(4'-methacryloylmethyl-)phenyl-3,3-di(2"-methacryloylethyl)-triaz(1)ene; 1-(4'-(methacryloylethyl)aminocarbonyl oxymethyl)phenyl-3,3-di(((methacryloylethyl)aminocarbonyl oxyethyl)-triaz(1)ene; 1-(3'-methacryloyethyl carboxphenyl)-3-di(2"-methacryloylethyl)triaz(1)ene; or 1,2-Bis[1-(3"-methacryloylethylcarboxyphenyl)-3-methyl]triaz(1)ene-ethane; 2-methacryloylmethyl-5-(3'-(2"methacryloylethyl)-3'-methyl)triaz(1)ene-thiophene.

23. The adhesive composition as in claim 11, wherein the bifunctional monomer is chosen from among: 1-(3'-ethyl glycidyl ether carboxyphenyl)-3-(ethyl glycidyl ether)-3-methyl-triaz(1)ene, 1-(3'-ethyl glycidyl ether carboxy-6'-methylphenyl)-3-(ethyl glycidyl ether)-3-methyl-triaz(1)ene; or 1-(4'methyl glycidyl ether)-3-(ethyl glycidyl ether)-3-methyl-triaz(1)ene.

24. The adhesive composition as in claim 7, wherein the bifunctional monomer is chosen from: 2-Methyl-acrylic acid 5-methoxy-4-[2-(2-methyl-acryloyloxy)-ethoxyl]-2-nitrobenzyl ester; 2-Methyl-acrylic acid 1-(5-methoxy-4-[2-methyl-acryloyloxy)-ethoxyl]-2-nitro-phenyl)-ethyl ester; 2-Methyl-acrylic acid 4,5-bis-[2-(2-methylacryloyloxy)-ethoxy]-2-nitro-benzyl ester; or 2-Methyl-acrylic acid 2-(5-methoxy-4-(2[2-(2-methyl-acryloyloxy)-ethoxycarbonyloxy]-ethoxy)-2-nitro-benzloxycarbonyloxy)-ethyl ester.

25. The adhesive composition as in claim 11, wherein the bifunctional monomer is chosen from among: 2-[2'nitro-4', 5'-di(oxymethyloxirane)]benzyloxymethyl oxirane; or (2-Methoxy-5-nitro-4-oxiranylmethoxymethyl-phenoxy)-acetic acid oxiranylmethyl ester.

26. The adhesive composition as in claim 12, wherein the bifunctional monomer is chosen from:
Poly[(14-(2'-aminoacylethyl)-6-(hydroxymethyl)-1,4,8,11-tetraoxa-12-oxo-13-aza-tetradecane)-co(7-(2'-4'-aminoacylethyl)-1,4-dioxa-5-oxo-6-aza-heptane)],
Poly[(14-(4'-aminoacylhexyl)-6-(hydroxymethyl)-1,4,8,11-tetraoxa-12-oxo-13-aza-tetradecane)-co-(7-(4'-aminoacylhexyl)-1,4-dioxa-5-oxo-6-aza-heptane)],
Poly[(14-(4'(4"-aminoacylphenyl)methylphenyl)-6-(hydroxymethyl)-1,4,8,11-tetraoxa-12-oxo-13-aza-tetradecane)-co-(7-(4'-(4"-amminoacylphenyl)methylphenyl)-1,4-dioxa-5-oxo-6-aza-heptane)],
Poly[(14-(4'-(4"-aminoacylcyclohexyl)methylcyclohexyl)-6-(hydroxymethyl)-1,4,8,11-tetraoxa-12-oxo-13-aza-tetradecane)-co-(7-(4'-(4"-aminoacylcyclohexyl)methylcyclohexyl)-1,4-dioxa5-oxo-6-aza-heptane)],
Poly((14-(4'-methylaminoacylcyclohexyl)-6-(hydroxymethyl)-1,4,8,11-tetraoxa-12-oxo-13-aza-tetradecane)-co-(7-(4'-methylaminoacylcyclohexyl)-1,4-dioxa-5-oxo-aza-heptane)], or
Poly[(14-(4'-aminoacylbutyl-6-(hydroxymethyl)-1,4,8,11-tetraoxa-12-oxo-13-aza-tetradecane)-co-(7-(4'-aminoacylbutyl)-1,4-dioxa-5-oxo-6-aza-heptane)]
in which all these polymers are esterified on the hydroxy group at position 6 of the copolymer chain by groups of type:
-oxycarbonyl-3-[3'-(2"-(methacrylate)ethyl))-3'-methyltriazene]phenyl, and/or
oxycarbonyl-ethyloxy-(1-methoxy-3-(methacrylatemethyl)-4-nitro)phenyl.

27. The adhesive composition as in claim 18, wherein the bifunctional monomer is chosen from among:
Poly(1-(3'-carboxyphenyl)-3-,3-di(2"hydroxyethyl)triazene),
Poly(1-(3'-carboxy-6'-methylphenyl)-3-,3-di(2"-hydroxyethyl)triazene)
Poly(1-(4'-carboxyphenyl)-3-,3-di(2"-hydroxyethyl)triazene),
Poly(1-(3',5'-dicarboxyphenyl)-3-(2"-hydroxyethyl)-3-methyl-triazene),
Poly(1(3'-carboxyphenyl)-3-,3-di(2"-hydroxyethyl)triazene-co-2,2-bis(hydroxymethyl)propionic acid),
Poly(1(3'-carboxy-6'-methylphenyl)-3-,3-di(2"-hydroxy ethyl)triazene-co-2,2-bis(hydroxymethyl)propionic acid), or
Poly(1-(4'carboxyphenyl)-3-,3-di(2"hydroxyethyl)triazene-co-2,2-bis(hydroxymethyl)propionic acid),
ω-functionalized by methacrylate ends with methacrylic acid and its derivatives, comprising one chosen from hydroxyethylmethacrylate, glycidyl methacrylate or 2-isocyanatoethyl methacrylate, or oxirane ends of glycidyl type by reaction with an epihalohydrine.

28. The adhesive composition as in claim 19, wherein the bifunctional monomer is chosen from among:
Poly(2,2-bis(hydroxymethyl)propionic acid-co-1-(3'-carboxy phenyl)-3-,3-di(2"-hydroxyethyl)triazene),
Poly(2,2-bis(hydroxymethyl)propionic acid-co-(3'-carboxy-6'-methyhenyl)-3-,3-di(2"-hydroxyethyl)triazene),
ω-functionalized by methacrylate ends with methacrylic acid and its derivatives, comprising one chosen from 2-hydroxyethylmethacrylate, glycidyl methacrylate or 2-isocyanatoethyl methacrylate, or by oxirane ends of glycidyl type by reaction with an epihalohydrine, or
Poly(2,2-bis(hydroxymethyl)propionic acid),
ω-functionalized by an oxycarbonyl-3-[3'-(2"(meth acrylate)ethyl))triazene]phenyl group or an -oxycarbonylethyl oxy-(1-methoxy-3-(methacrylatemethyl)-4-nitro) phenyl group.

29. The adhesive composition as in claim 2, wherein the photoinitiation means for radical or cationic polymerization reaction comprise at least one species able to cause their photo-sensitization.

30. The adhesive composition as in claim 2, wherein the photoinitiation means for radical polymerization reaction also comprise a co-initiator.

31. The adhesive composition as in claim 30, wherein the photoinitiation means for radical polymerization reaction consist of the following photoinitiator/co-initiator pair: camphorquinone/tertiary amine.

32. The adhesive composition as in claim 2, wherein the photoinitiation means for radical polymerization reaction consist of a photoinitiator which is a bis-acyl of phosphine oxide.

33. The adhesive composition as in claim 1, wherein the initiation means of the chain polymerization reaction(s) are of chemical type.

34. A bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, wherein said bifunctional monomer is of oligomer or prepolymer size and has a comb branched structure consisting of a principal linear polymer chain of which each of the comb branches contain at least one photocleavable unit positioned on the side of the principal chain and at least one polymerizable unit positioned on the free end of the branch, the photocleavable units being chosen from the aryldiazos defined by formula I

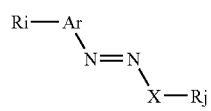

in which:
Ar designates an aromatic system, monocylic or polycylic, carbocyclic or heterocyclic,
X designates an atom chosen from among: C,O,P,S;
Ri is one or more of the following groups: hydrogeno, halogeno, alkyl linear or branched, saturated or unsaturated, optionally substituted, aryl aromatic or heteoaromatic, substituted or unsubstituted, alcoxy comprising at least one selected from the group consisting of methoxy, ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group, —OCO$_2$R', —OSO$_2$R', —OPOOR'OR", —R'NHCOOR", —R'OCO$_2$R", —NR'R" (in which R' and R" represent an alkyl group, carbocyclic or heterocyclic group, aliphatic, unsaturated, (hetero-)aromatic group, all substituted or unsubstituted, imine whether substituted or not, nitro, —N=N—R', -Rp-Si—(ORq)$_3$ group (in which Rp is a hydrocarbon chain or a linear alkyl chain comprising at least 3 C atoms, and Rq denotes a hydrogen atom, a hydroxy group, $C_1$-$C_6$ alcoxy chain or —(Si(ORq) group), vinyl group, acrylic group, alcoxycarbonyl group, and an aryltriazene group,
Rj designates one or more substituents depending upon the valency of the atom designated by X, the same or different and chosen from among: an alkyl chain linear or branched, saturated or unsaturated, acyclic or cyclic, optionally substituted; an aromatic or heteoaromatic group including, at least one nitrogen or sulfur atom, monocyclic or polycyclic; an alcoxy, aryloxy chain or benzyl group.

35. A bifunctional monomer including firstly a photocleavable centre comprising at least one photocleavable unit and secondly at least two polymerizable units linked by covalent skeletons to said photocleavable centre and positioned either side of the cleavage site or sites of said photocleavable centre, wherein said bifunctional monomer is of oligomer or prepolymer size and has a hyperbranched structure obtained by polycondensation or polyaddition of precursor monomers of AB$_2$ or AB$_3$ type.

36. The bifunctional monomer as in claim 35, wherein the hyperbranched structure has a core consisting of photocleavable units and a peripheral shell consisting of inert units from a photochemical viewpoint.

37. The bifunctional monomer as in claim 35, wherein the hyperbranched structure has a core consisting of photochemically inert units, and a peripheral shell comprising photocleavable units.

38. A method for preparing a bifunctional monomer including firstly a photocleavable centre comprising at least one photocleavable unit chosen from among the aryltriazenes defined by formula II, and secondly at least two polymerizable units linked by covalent skeletons to said photocleavable centre and positioned either side of the cleavage site or sites of said photocleavable centre, said method successively comprising a synthesis step of the photocleavable centre, a structural arrangement step of the photocleavable centre, and an association step associating the polymerizable units with the photocleavable centre, wherein the synthesis step of an ayltriazene photocleavable unit consists of:
conducting diazotation in inert organic medium in the presence of a Lewis acid of type BF$_3$ or PF$_5$ or SbF$_5$ and of an organic nitrite,
then conducting diazoic coupling by adding a compound comprising at least one primary or secondary amino group, in a dissociating organic medium in the presence of a mineral compound of sodium carbonate, potassium carbonate or sodium hydrogenocarbonate type, wherein formula II is defined as,

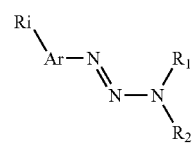

in which:
Ar designates an aromatic system monocylic or polycylic, carbocyclic or heterocyclic,
Ri is chosen from among the following groups: alkyl linear or branched, saturated or unsaturated, optionally substituted, aryl aromatic or heteoaromatic, substituted or unsubstituted, alcoxy comprising one selected from the group consisting of methoxy, ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group or —OCO$_2$R', —OSO$_2$R', —OPOOR'OR", —R'NHCOOR", —R'OCO$_2$R", —NR'R" (in which R' and R" represent an alkyl group, carbocyclic or heterocyclic group, aliphatic, unsaturated, a (hetero-)aromatic group, all substituted or unsubstituted, nitro, —N═N—R', -Rp-Si—(ORq)$_3$ group (Rp and Rq as previously defined above), a vinyl group, acrylic group, alcoxycarbonyl group, and an aryltriazene group, $R_1$ and $R_2$ are chosen independently from one another, a —N═N—R' group, —NR'—N═N—R" group, OH group, NR'R" group, (R' and R" have the previously given denotations), an alkyl group comprising at least one selected from the group consisting of methyl, ethyl, propyl, or unsubstituted, diazo —N═N—R', a -Rp-Si—(ORq)$_3$ group (Rp and Rq as defined in claim 3), alkylglycidyl ether, alkylvinyl ether, cyclohexyl epoxy, $R_{m1}/R_{m2}$ are independently chosen from among: a hydrogen, an alkyl, alcenyl, alcynyl, alkylaryl chain, all substituted or unsubstituted, a carbocyclic or heterocyclic chain saturated or unsaturated, aromatic or heteroaromatic, substituted or unsubstituted, an alcoxy, aryloxy, alkylthio, arylthio chain, an alkyloxocarbonyl group, —NR'COR" group, —OCOR' group, —OCOOR' group, —OCONR'R" group, NR'COOR" group, —OPOR'R"R'" group, —OSO$_2$R' group, —OPOOR'OR" group, —NR'R", —COOR' group, —CONR'R", SOOR', —COR' group (R', R" and R'" have the previously indicated denotations for R' and R"), an imine group substituted or unsubstituted, a hydroxy, thiol group, a carboxylic acid or derivative of carboxylic acid, a halogen, a nitrile, an alkyl(C1-C6)glycidyl ether group, alkyl(C1-C6)vinyl ether group, cyclohexyl epoxy, -Rp-Si—(ORq)$_3$ group (Rp and Rq as previously defined above).

39. A method for preparing a bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, said method successively comprises a synthesis step of the photocleavable centre, a structural arrangement step of the photocleavable centre, and an association step associating the polymerizable units with the photocleavable centre, wherein said method comprises a creation step to create polymerizable units of vinyl type on the photocleavable centre, consisting of the creation of acryloyl functions by nucleophilic substitution on an acryloyl carbon.

40. A method for preparing a bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, said method successively comprises a synthesis step of the photocleavable centre, a structural arrangement step of the photocleavable centre, and an association step associating the polymerizable units with the photocleavable centre, wherein said method comprises a grafting step to graft vinyl type polymerizable units onto the photocleavable centre, consisting of grafting the vinyl function included in a molecule comprising at least one reactive function (F1) onto the chemical skeleton of the photocleavable centre, and also comprising at least one other reactive function (F2), by causing these two functions to react via a nucleophilic substitution mechanism on an acyl type carbon.

41. The method as in claim 40, wherein one of the two reactive functions (F1,F2) is an OR group or an —OOCR group.

42. A method for preparing a bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, said method successively comprises a synthesis step of the photocleavable centre, a structural arrangement step of the photocleavable centre, and an association step associating the polymerizable units with the photocleavable centre, wherein said method comprises a grafting step to graft vinyl type polymerizable units onto the photocleavable centre, consisting of grafting the vinyl function included in a molecule comprising at least one reactive function (F1) onto the chemical skeleton of the photocleavable core, and also comprising at least one other reactive function (F2), by causing these two functions (F1, F2) to react to form a carbamate bond.

43. A method for preparing a bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, said method successively comprises a synthesis step of the photocleavable centre, a structural arrangement step of the photocleavable centre, and an association step associating the polymerizable units with the photocleavable centre, wherein said method comprises a grafting step to graft vinyl type polymerizable units onto the photocleavable centre, consisting of grafting the vinyl function included in a molecule comprising at least one reactive function (F1) onto the chemical skeleton of the photocleavable centre, and also comprising at least one other reactive function (F2), by causing these two functions (F1, F2) to react to form a β-hydroxyester bond through attack by a carboxylate anion on an oxirane under conditions of nucleophilic catalysis, in the presence of catalysts carrying tertiary amino or quaternary ammonium groups.

44. A method for preparing a bifunctional monomer of oligomer or prepolymer size as in claim 35, in which function A being a carboxylic acid function and function B an alcohol or amino function, the polycondensation or polyaddition reaction of the precursor monomers of AB$_2$ or AB$_3$ type is conducted in the presence of dehydrating agents.

45. The method as in claim 44, wherein the dehydrating agents are chosen from among: 1-methyl-2-chloropyridinium iodide, dicyclohexylcarbodiimide, N,N'-diisopropylcarbodiimide, N,N'-carbonyldiimidazole, 1,1'carbonylbis(3-methylimidazolium)triflate, di-2-pyridyl carbonate, 1-hydroxybenzotriazole, an acylation agent of Pyridine/Tosyl Chloride type or SOCl$_2$/DMF.

46. A method for preparing a bifunctional monomer of oligomer or prepolymer size as in claim 35, in which function A being an ester function and function B an alcohol or amino function, the transesterification reaction of the precursor monomers of AB$_2$ or AB$_3$ type is conducted in the presence of catalysts comprising one selected from the group consisting of titanates, organic tin oxides and esters, using basic catalysis in the presence of non-ionic bases providing soft operating conditions optionally comprising amines, amidines, guanidines, triamino(imino)-phosphoranes.

47. A method of using the photosensitive adhesive composition as in claim 1 for various clinical applications in the area of dentistry, to bond elements to the surface of teeth and/or to seal tooth cavities.

48. A bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, wherein said bifunctional monomer is of oligomer or prepolymer size and has a comb branched structure consisting of a principal linear polymer chain of which each of the comb branches contain at least one photocleavable unit positioned on the side of the principal chain and at least one polymerizable unit positioned on the free end of the branch, the photocleavable units being chosen from the 2-nitrobenzyls defined by formula 1

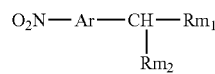
    1 in which:
  Ar designates an aromatic or heteroaromatic radical monocyclic or polycyclic and carrying at least one Rk substituent,
  Rk designates an auxochromic or bathochromic substituent, which may be chosen from the following examples: hydrogen, halogen, alkyl chain, aliphatic acyclic saturated or unsaturated, linear or branched, a cyclic, aliphatic, unsaturated, aromatic or heteroaromatic radical, these chains and radicals possibly being substituted, interrupted or terminated by a heteroatom comprising at least one selected from the group consisting of B, N, O, Si, P, S and a halogen, a nitro group, cyano group, an alcoxy, aryloxy, alkylthio, arylthio, benzyl, arylalkyl, hydroxy, thiol, alkyloxycarbonyl, aryloxycarbonyl, carbonyl, formyl, amino radical, carboxylic ester, amide, sulfonic ester, sulfonic amide, carboxylic acid, sulfonic acid, sulfonate, phosphonate, a —OCONR'R" group, —OCO$_2$R', —OSO$_2$R', —OPOOR'OR", —R'NHCOOR", R'OCO$_2$R", NR'R" (R' and R" are an alkyl, aryl group, a carbocyclic or heterocarbocyclic group), imine substituted or unsubstituted, diazo —N=N—R', a -Rp-Si(ORq)$_3$ group (Rp and Rq as defined in claim 3), alkylglycidyl ether, alkylvinyl ether, cyclohexyl epoxy,
  $R_{m1}/R_{m2}$ are independently chosen from among: a hydrogen, an alkyl, alcenyl, alcynyl, alkylaryl chain, all substituted, a carbocyclic or heterocyclic chain saturated or unsaturated, aromatic or heteroaromatic, substituted or unsubstituted, an alcoxy, aryloxy, alkylthio, arylthio chain, an alkyloxocarbonyl group, —NR'COR" group, —OCOR' group, —OCOOR' group, —OCONR'R" group, NR'COOR" group, —OPOR'R"R'" group, —OSO$_2$R' group, —OPOOR'OR" group, —NR'R", —COOR'group, —CONR'R", SOOR', —COR' group (R', R" and R'" have the previously indicated denotations for R' and R"), an imine group substituted or unsubstituted, a hydroxy, thiol group, a carboxylic acid or derivative of carboxylic acid, a halogen, a nitrile, an alkyl(C1-C6)glycidyl ether group, alkyl(C1-C6)vinyl ether group, cyclohexyl epoxy, -Rp-Si—(ORq)$_3$ group (Rp and Rq as previously defined above).

49. A bifunctional monomer including firstly a photocleavable centre comprising at least one photocleavable unit, and secondly at least two polymerizable units linked by covalent skeletons to said photocleavable centre and positioned either side of the cleavage site or sites of said photocleavable centre, wherein said bifunctional monomer is of oligomer or prepolymer size and has a comb branched structure consisting of a principal linear polymer chain of which each of the comb branches contain at least one photocleavable unit positioned on the side of the principal chain and at least one polymerizable unit positioned on the free end of the branch, the photocleavable units being chosen from the 2-nitrobenzyls defined by formula 2

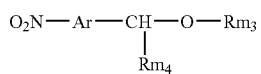
    2 in which:
  Ar is an aromatic system, monocyclic or polycyclic, carbocyclic or heterocyclic,
  $R_{m4}$ is defined as Rm1/Rm2 in claim 9,
  $R_{m3}$ is chosen from among a hydrogen, an alkyl, alcenyl, alcynyl, alkylaryl chain, all substituted or unsubstituted, interrupted by a heteroatom, a carbocyclic or heterocyclic chain, saturated or unsaturated, aromatic or heteroaromatic, substituted or unsubstituted, an alkyloxycarbonyl group, NCOOR' group, —POR'R"R'" group, —SO$_2$R' group, —POOR'OR" group, —COOR' group, —CONR'R", COR' group (R', R" and R'" having the previously indicated denotations for R' and R"'in claim 9), an alkyl($C_1$-$C_6$)glycidyl ether group, alkyl(C1-C6) vinyl ether group, cyclohexyl epoxy, -Rp-Si(ORq)$_3$ group (Rp and Rq as previously defined above).

50. A photosensitive adhesive composition of polymerizable resin type whose hardening is obtained by polymerization and/or cross-linking characterized in that said composition contains:
  at least one chain polymerization reaction initiator that ensures hardening of said composition, and
  a sufficient quantity of at least one bifunctional monomer including firstly a photocleavable centre comprising at least one photocleavable unit selected from the group consisting of:
    (i) aryl-diazos units defined by formula I:

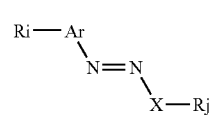
    I in which:
  Ar designates an aromatic system, monocylic or polycylic, carbocyclic or heterocyclic,
  X designates an atom chosen from among: C,O,P,S;
  Ri is one or more of the following groups: hydrogeno, halogeno, alkyl linear or branched, saturated or unsaturated, optionally substituted, aryl aromatic or heteoaromatic, substituted or unsubstituted, alcoxy comprising at least one selected from the group consisting of methoxy, ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group, —OCO$_2$R', —OSO$_2$R', —OPOOR'OR", —R'NHCOOR", —R'OCO$_2$R", —NR'R" (in which R' and R" represent an alkyl group, carbocyclic or heterocyclic group, aliphatic, unsaturated, (hetero-)aromatic group, all substituted or unsubstituted, imine whether substituted or not, nitro, —N=N—R', -Rp-Si—(ORq)$_3$ group (in which Rp is a hydrocarbon chain or a linear alkyl chain comprising at least 3 C atoms, and Rq denotes a hydrogen atom, a hydroxy group, $C_1$-$C_6$ alcoxy chain or —(Si(ORq) group), vinyl group, acrylic group, alcoxycarbonyl group, and an aryltriazene group, Rj designates one or more substituents depending upon the valency of the atom designated by X, the same or different and chosen from among: an alkyl chain linear or branched, saturated or unsaturated, acyclic or cyclic, optionally substituted; an aromatic or heteroaromatic group including, at least one nitrogen or sulfur atom, monocyclic or polycyclic; an alcoxy, aryloxy chain or benzyl group;

(ii) aryl-triazene units defined by formula II:

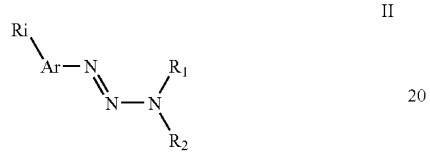

II in which:

Ar designates an aromatic system monocyclic or polycyclic, carbocyclic or heterocyclic, Ri is chosen from among the following groups: alkyl linear or branched, saturated or unsaturated, optionally substituted, aryl aromatic or heteoaromatic, substituted or unsubstituted, alcoxy comprising one selected from the group consisting of methoxy, ethoxy, aryloxy, alkylthio, arylthio, benzyl, halogeno, hydroxy, hydroxyalkyl, thiol, alkyloxycarbonyl, aryloxycarbonyl, cyano, carbonyl, formyl, amino, carboxylic and sulfonic ester, carboxylic sulfonic and phosphoric amide, carboxylic sulfonic and phosphoric acid, sulfonate, phosphonate, —OCONR'R" group or —OCO₂R', —OSO₂R', —OPOOR'OR", —R'NHCOOR", —R'OCO₂R", —NR'R" (in which R' and R" represent an alkyl group, a carbocyclic or heterocyclic group, aliphatic, unsaturated, a (hetero-)aromatic group, all substituted or unsubstituted, imine substituted or unsubstituted, nitro, —N=N—R', -Rp-Si—(ORq)₃ group (Rp and Rq as previously defined above), a vinyl group, acrylic group, alcoxycarbonyl group, and an aryltriazene group, $R_1$ and $R_2$ are chosen independently from one another, a —N=N—R' group, —NR'—N=N—R" group, OH group, NR'R" group, (R' and R" have the previously given denotations), an alkyl group comprising at least one selected from the group consisting of methyl, ethyl, propyl, isopropyl, butyl, tert-butyl, an alcoxy group substituted or not, a benzyl group, a (hetero)-aromatic group, all substituted or not by substituents of Ri type, a hydroxyethyl, cyanoethyl, aminoethyl, acryloxyethyl, and halogenoethyl group (iii) 2-nitrobenzyl units having the formula 1:

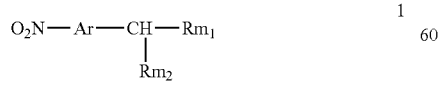

1 in which:

Ar designates an aromatic or heteroaromatic radical monocyclic or polycyclic and carrying at least one Rk substituent, Rk designates an auxochromic or bathochromic substituent which may be chosen from the following examples: hydrogen, halogen, alkyl chain, aliphatic acyclic saturated or unsaturated, linear or branched, a cyclic, aliphatic, unsaturated, aromatic or heteroaromatic radical, these chains and radicals possibly being substituted, interrupted or terminated by a heteroatom comprising at least one selected from the group consisting of B, N, O, Si, P, S and a halogen, a nitro group, cyano group, an alcoxy, aryloxy, alkylthio, arylthio, benzyl, aylalkyl, hydroxy, thiol, alkyloxycarbonyl, aryloxycarbonyl, carbonyl, formyl, amino radical, carboxylic ester, amide, sulfonic ester, sulfonic amide, carboxylic acid, sulfonic acid, sulfonate, phosphonate, a —OCONR'R" group, —OCO₂R', —OSO₂R', —OPOOR'OR", —R'NHCOOR", R'OCO₂R", NR'R" (R' and R" are an alkyl, aryl group, a carbocyclic or heterocyclic group), imine substituted or unsubstituted, diazo —N=N—R', -Rp-Si(ORq)₃ group (Rp and Rq as previously defined), alkylglycidyl ether, alkylvinyl ether, cyclohexyl epoxy, $R_{m1}/R_{m2}$ are independently chosen from among: a hydrogen, an alkyl, alcenyl, alcynyl, alkylaryl chain, all substituted or unsubstituted, a carbocyclic or heterocyclic chain saturated or unsaturated, aromatic or heteroaromatic, substituted or unsubstituted, an alcoxy, aryloxy, alkylthio, arylthio chain, an alkyloxocarbonyl group, —NR'COR" group, —OCOR' group, —OCOOR' group, —OCONR'R" group, NR'COOR" group, —OPOR'R"R'" group, —OSO₂R' group, —OPOOR'OR" group, —NR'R", —COOR' group, —CONR'R", SOOR', —COR' group (R', R" and R'" have the previously indicated denotations for R' and R"), an imine group substituted or unsubstituted, a hydroxy, thiol group, a carboxylic acid or derivative of carboxylic acid, a halogen, a nitrile, an alkyl(C1-C6)glycidyl ether group, alkyl(C1-C6)vinyl ether group, cyclohexyl epoxy, -Rp-Si—(ORq)₃ group (Rp and Rq as previously defined above)

(iv) 2-nitrobenzyl units defined by formula 2:

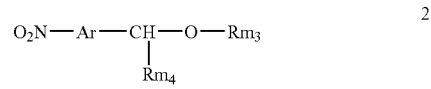

2 in which:

Ar is an aromatic system, monocyclic or polycyclic, carbocyclic or heterocyclic, $R_{m4}$ is defined as Rm1/Rm2, $R_{m3}$ is chosen from among a hydrogen, an alkyl, alcenyl, alcynyl, alkylaryl chain, all substituted or unsubstituted, interrupted by a heteroatom, a carbocyclic or heterocyclic chain, saturated or unsaturated, aromatic or heteroaromatic, substituted or unsubstituted, an alkyloxocarbonyl group, NCOOR' group, —POR'R"R'" group, —SO₂R' group, —POOR'OR" group, —COOR' group, —CONR'R", COR' group (R', R" and R'" having the previously indicated denotations for R' and R" in claim 9), an alkyl($C_1$-$C_6$)glycidyl ether group, alkyl(C1-C6)

vinyl ether group, cyclohexyl epoxy, -Rp-Si(ORq)$_3$ group (Rp and Rq as previously defined above),
(v) 2-nitrobenzyl units defined by formula 3:

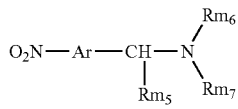

in which:
Ar is defined as previously,
$R_{m5}$ is defined as $R_{11}/R_{12}/R_{13}$,
$R_{m6}/R_{m7}$ are defined as a hydrogen, an alkyl, alcenyl, alcynyl, alkylaryl chain, substituted or not, interrupted by a heteroatom, a carbocyclic or heterocyclic chain, (un)saturated, (hetero)-aromatic, substituted or not, an alkyloxycarbonyl group, —R'COR'' group, R'COOR'' group, R'R'', —COOR' group, —CONR'R'', a COR' group (R' and R''having the denotations previously given), a hydroxy group, alkyl(C1-C6)glycidyl ether or alkyl(C1-C6)vinyl ether, cyclohexyl epoxy, -Rp-Si(ORq)$_3$ group (Rp and Rq as defined previously above), and
(vi) 2-nitrobenzyl units defined by formula 4:

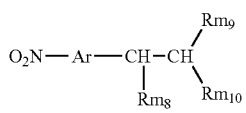

in which:
Ar is defined as previously,
$R_{m8}/R_{m9}/R_{m10}$ are defined as $R_{11}/R_{12}/R_{13}$ as defined above; and
secondly at least two polymerizable units linked by covalent skeletons to said photocleavable centre and positioned either side of the cleavage site or sites of said photocleavable centre so that said hardened composition loses its integrity and adhesiveness under the action of uncrosslinking radiation which causes cleavage of the photocleavable units,
wherein the initiator for chain polymerization reaction(s) are photoinitiating means consisting of at least one photoinitiator able to initiate the polymerization reaction mechanism under the action of crosslinking radiation whose wavelength λ1 is different to wavelength λ2 for uncrosslinking radiation,
said composition further comprises at least two types of complementary vinyl units, capable of creating a charge transfer complex (electron donor/acceptor pair) itself able to initiate a radical reaction under the action of crosslinking radiation of wavelength λ1, or at least one type of acceptor vinyl unit able to create a charge transfer with another complementary species.

51. The adhesive composition as in claim 50, wherein the donor vinyl unit is chosen from among the elements: styrene, vinyl acetate, vinyl ether, exomethylene dioxolane, 4-methylene-2-phenyl-1,3-dioxolane, alkyl methacrylate, vinyl pyrrolidone, vinyl carbazole, vinyl naphthalene, while the vinyl unit of acceptor type is chosen from among the elements: maleic anhydride, acrylonitrile, diethyl fumarate, fumaronitrile, maleimides.

\* \* \* \* \*

UNITED STATES PATENT AND TRADEMARK OFFICE
CERTIFICATE OF CORRECTION

PATENT NO. : 7,544,721 B2
APPLICATION NO. : 10/510112
DATED : June 9, 2009
INVENTOR(S) : Vincent Gaud et al.

It is certified that error appears in the above-identified patent and that said Letters Patent is hereby corrected as shown below:

In claim 38, column 69, line 6, after "group,", insert --and--.

In claim 38, column 69, after "epoxy", delete "," and insert --.--.

In claim 38, column 69, from line 15 to line 32, delete

"$R_{m1}/R_{m2}$ are independently chosen from among: a hydrogen, an alkyl, alcenyl, alcynyl, alkylaryl chain, all substituted or unsubstituted, a carbocyclic or heterocyclic chain saturated or unsaturated, aromatic or heteroaromatic, substituted or unsubstituted, an alcoxy, aryloxy, alkylthio, arylthio chain, an alkyloxocarbonyl group, —NR'COR" group, —OCOR' group, —OCOOR' group, —OCONR'R" group, NR'COOR" group, —OPOR'R"R'" group, —OSO$_2$R' group, —OPOOR'OR" group, —NR'R", —COOR' group, —CONR'R", SOOR', —COR' group (R', R" and R'" have the previously indicated denotations for R' and R"), an imine group substituted or unsubstituted, a hydroxy, thiol group, a carboxylic acid or derivative of carboxylic acid, a halogen, a nitrile, an alkyl(Cl-C6)glycidyl ether group, alkyl(Cl-C6)vinyl ether group, cyclohexyl epoxy, -Rp-Si—(ORq)$_3$ group (Rp and Rq as previously defined above).".

Signed and Sealed this

Twenty-fifth Day of August, 2009

David J. Kappos
*Director of the United States Patent and Trademark Office*